United States Patent

Ashley et al.

(10) Patent No.: US 6,489,314 B1
(45) Date of Patent: *Dec. 3, 2002

(54) EPOTHILONE DERIVATIVES AND METHODS FOR MAKING AND USING THE SAME

(75) Inventors: Gary Ashley, Alameda, CA (US); Brian Metcalf, Moraga, CA (US)

(73) Assignee: Kosan Biosciences, Inc., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/825,856

(22) Filed: Apr. 3, 2001

(51) Int. Cl.⁷ .............. A61K 31/33; C07D 291/00; C07D 225/04; C07D 491/00; C07D 225/02
(52) U.S. Cl. .......... 514/183; 540/451; 540/455; 540/461; 540/462; 540/463
(58) Field of Search ............ 540/455, 461, 540/462, 463; 514/183

(56) References Cited

U.S. PATENT DOCUMENTS 5,886,026 A * 3/1999 Hunter
6,302,838 B1 * 10/2001 O'Reilly et al.
6,365,749 B1   4/2002 Kim et al. .................. 548/204

FOREIGN PATENT DOCUMENTS

| WO | WO 98/24427 A2 | * | 6/1998 |
| WO | WO 99/02514 | | 1/1999 |
| WO | WO 99/076692 A2 | * | 2/1999 |
| WO | WO 99/65913 | | 12/1999 |

OTHER PUBLICATIONS

Hofle et al., Angew. Chem. Int. Ed. Engl. (1996) 35(13/14):1567–1569.
Borzilleri, R. et al. (2000) *J Am Chem Soc* 122:8890–8897.
U.S. patent application Ser. No. 10/115,198, Ashley et al., filed Apr. 2, 2002.

* cited by examiner

*Primary Examiner*—Johann Richter
*Assistant Examiner*—Paul A. Zucker
(74) *Attorney, Agent, or Firm*—David Lentini; Carolyn A. Favorito; Kevin Kaster

(57) ABSTRACT

The present invention relates to 16-membered macrocyclic compounds. In one aspect of the present invention, compounds of the formula

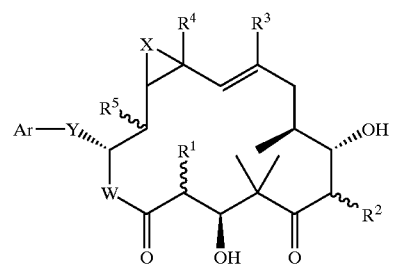

are provided wherein:

$R^1$, $R^2$, $R^3$, and $R^5$ are each independently hydrogen, $C_1$–$C_{10}$ alkyl, $C_2$–$C_{10}$ alkenyl, $C_2$–$C_{10}$ alkynyl, aryl or alkylaryl;

$R^4$ is hydrogen, halogen, $C_1$–$C_{10}$ alkyl, $C_1$–$C_{10}$ hydroxyalkyl, $C_1$–$C_{10}$ haloalkyl, aryl, —C(=O)$R^6$, —C(=O)O$R^6$, —N$R^6R^7$ where $R^6$ and $R^7$ are each independently hydrogen, $C_1$–$C_{10}$ aliphatic, aryl or alkylaryl;

W is O, N$R^8$ where $R^8$ is hydrogen, $C_1$–$C_{10}$ alkyl, $C_2$–$C_{10}$ alkenyl, $C_2$–$C_{10}$ alkynyl, aryl or alkylaryl;

X is O, $CH_2$ or a carbon-carbon double bond;

Y is absent or a $C_1$–$C_{10}$ alkyl, $C_2$–$C_{10}$ alkenyl, or $C_2$–$C_{10}$ alkynyl; and Ar is aryl; provided that 10,11-dehydroepothilone C is excluded.

27 Claims, No Drawings

EPOTHILONE DERIVATIVES AND METHODS FOR MAKING AND USING THE SAME

CROSS REFERENCE TO RELATED APPLICATIONS

The present application is related to U.S. Utility application Ser. No. 09/825,876 filed on Apr. 3, 2001 by inventors Robert Arslanian, John Carney and Brian Metcalf entitled EPOTHILONE COMPOUNDS AND METHODS FOR MAKING AND USING THE SAME, which is incorporated herein by reference.

BACKGROUND

Epothilone A (R=H) and Epothilone B (R=CH$_3$) are produced by *Sorangium cellulosum* strain So ce 90, the structures of which are shown below, and were the first of several epothilones to be isolated and characterized. Hofle et al., 1996, *Angew. Chem. Int. Ed. Engl.* 35(13/14): 1567–1569.

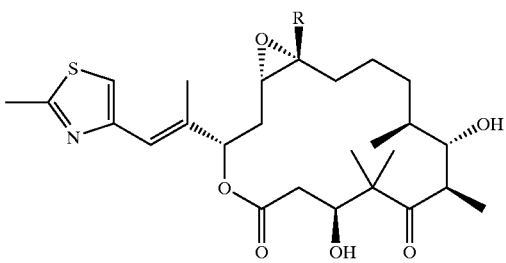

Epothilone A and epothilone B possess many of the advantageous properties of taxol. As a result, there is significant interest in these and structurally related compounds as potential chemotherapeutic agents. The desoxy counterparts of epothilones A and B are known as epothilone C (R=H) and epothilone D (R=CH$_3$), and also exhibit similar anti-tumor activity but with less cytotoxicity. The structures of epothilones C and D are shown below.

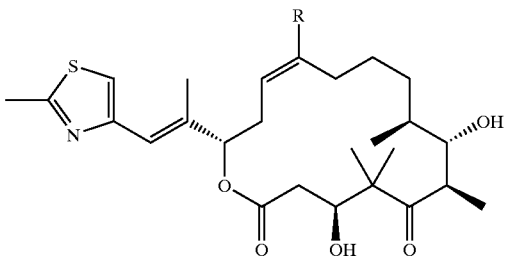

Although other naturally occurring epothilones have been described in the literature, these compounds are produced in exceedingly small amounts. For example, PCT publication WO 99/65913 describes 39 naturally occurring epothilones obtained from *Sorangium cellulosum* So ce 90 of which epothilones A, B, C, and D together account for approximately 98.9% of the total epothilones produced. The 35 other naturally occurring epothilone compounds together account for the remaining 1.1% and include epothilone C$_6$ (which may also be referred to as 10,11-dehydroepothilone C) and whose structure is shown below

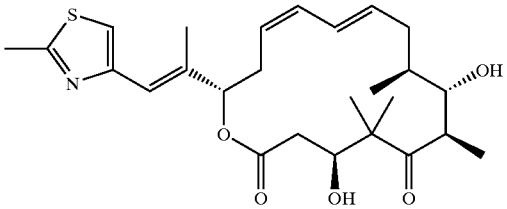

Due to the increasing interest in epothilones as anti-cancer agents, novel derivatives of these compounds are needed and desired to more fully develop their therapeutic potential.

SUMMARY

The present invention relates to 16-membered macrocyclic compounds. In one aspect of the present invention, 16-membered macrocyclic compounds having a conjugated diene are provided. In another aspect of the present invention, compounds of the following formula

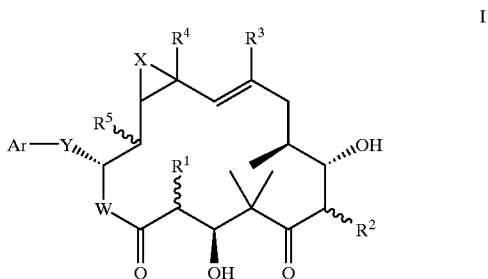

are provided wherein:

R$^1$, R$^2$, R$^3$, and R$^5$ are each independently hydrogen, C$_1$–C$_{10}$ alkyl, C$_2$–C$_{10}$ alkenyl, C$_2$–C$_{10}$ alkynyl, aryl or alkylaryl;

R$^4$ is hydrogen, C$_1$–C$_{10}$ alkyl, C$_1$–C$_{10}$ hydroxyalkyl, C$_1$–C$_{10}$ haloalkyl, aryl, —C(=O)R$^6$, —C(=O)OR$^6$, —NR$^6$R$^7$ where R$^6$ and R$^7$ are each independently hydrogen, C$_1$–C$_{10}$ aliphatic, aryl or alkylaryl;

W is O, NR$^8$ where R$^8$ is hydrogen, C$_1$–C$_{10}$ alkyl, C$_2$–C$_{10}$ alkenyl, C$_2$–C$_{10}$ alkynyl, aryl or alkylaryl;

X is O, CH$_2$ or a carbon-carbon double bond;

Y is absent or a C$_1$–C$_{10}$ alkyl, C$_2$–C$_{10}$ alkenyl, or C$_2$–C$_{10}$ alkynyl; and Ar is aryl; provided that 10,11-dehydroepothilone C is excluded. In another aspect of the present invention, methods for using the inventive compounds are provided.

DETAILED DESCRIPTION OF THE PREFERRED EMBODIMENTS

The present invention relates to novel compounds that are useful for the treatment of cancer and other conditions characterized by abnormal cellular proliferation in a subject in need thereof.

Definitions

Statements regarding the scope of the present invention and definitions of terms used herein are listed below. The definitions apply to the terms as they are used throughout this specification, unless otherwise limited in specific instances, either individually or as part of a larger group.

All stereoisomers of the inventive compounds are included within the scope of the invention, as pure compounds as well as mixtures thereof. Individual enantiomers, diastereomers, geometric isomers, and combinations and mixtures thereof are all encompassed by the present invention. Furthermore, some of the crystalline forms for the compounds may exist as polymorphs and as such are included in the present invention. In addition, some of the compounds may form solvates with water (i.e., hydrates) or common organic solvents, and such solvates are also encompassed within the scope of this invention.

Protected forms of the inventive compounds are included within the scope of the present invention. A variety of protecting groups are disclosed, for example, in T. H. Greene and P. G. M. Wuts, Protective Groups in Organic Synthesis, Third Edition, John Wiley & Sons, New York (1999), which is incorporated herein by reference in its entirety. For example, a hydroxy protected form of the inventive compounds are those where at least one of the hydroxyl groups is protected by a hydroxy protecting group. Illustrative hydroxyl protecting groups include but not limited to tetrahydropyranyl; benzyl; methylthiomethyl; ethylthiomethyl; pivaloyl; phenylsulfonyl; triphenylmethyl; trisubstituted silyl such as trimethyl silyl, triethylsilyl, tributylsilyl, triisopropylsilyl, t-butyldimethylsilyl, tri-t-butylsilyl, methyldiphenylsilyl, ethyldiphenylsilyl, t-butyldiphenylsilyl and the like; acyl and aroyl such as acetyl, pivaloylbenzoyl, 4-methoxybenzoyl, 4-nitrobenzoyl and aliphatic acylaryl and the like. Keto groups in the inventive compounds may similarly be protected.

The present invention includes within its scope prodrugs of the compounds of this invention. In general, such prodrugs are functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to a subject in need thereof. Conventional procedures for the selection and preparation of suitable prodrug derivatives are described, for example, in "Design of Prodrugs", H. Bundgaard ed., Elsevier, 1985.

As used herein, the term "aliphatic" refers to saturated and unsaturated straight chained, branched chain, cyclic, or polycyclic hydrocarbons that may be optionally substituted at one or more positions. Illustrative examples of aliphatic groups include alkyl, alkenyl, alkynyl, cycloalkyl, cycloalkenyl, and cycloalkynyl moieties. The term "alkyl" refers to straight or branched chain saturated hydrocarbon substituent. "Alkenyl" refers to a straight or branched chain hydrocarbon substituent with at least one carbon-carbon double bond. "Alkynyl" refers to a straight or branched chain hydrocarbon substituent with at least one carbon-carbon triple bound.

The term "aryl" refers to monocyclic or polycyclic groups having at least one aromatic ring structure that optionally include one or more heteroatoms and preferably include three to fourteen carbon atoms. Aryl substituents may optionally be substituted at one or more positions. Illustrative examples of aryl groups include but are not limited to: furanyl, imidazolyl, indanyl, indenyl, indolyl, isooxazolyl, isoquinolinyl, naphthyl, oxazolyl, oxadiazolyl, phenyl, pyrazinyl, pyridyl, pyrimidinyl, pyrrolyl, pyrazolyl, quinolyl, quinoxalyl, tetrahydronaphththyl, tetrazolyl, thiazolyl, thienyl, and the like.

The aliphatic (i.e., alkyl, alkenyl, etc.) and aryl moieties may be optionally substituted with one or more substituents, preferably from one to five substituents, more preferably from one to three substituents, and most preferably from one to two substituents. The definition of any substituent or variable at a particular location in a molecule is independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein. Examples of suitable substituents include but are not limited to: alkyl, alkenyl, alkynyl, aryl, halo; trifluoromethyl; trifluoromethoxy; hydroxy; alkoxy; cycloalkoxy; heterocyclooxy; oxo; alkanoyl (—C(=O)-alkyl which is also referred to as "acyl")); aryloxy; alkanoyloxy; amino; alkylamino; arylamino; aralkylamino; cycloalkylamino; heterocycloamino; disubstituted amines in which the two amino substituents are selected from alkyl, aryl, or aralkyl; alkanoylamino; aroylamino; aralkanoylamino; substituted alkanoylamino; substituted arylamino; substituted aralkanoylamino; thiol; alkylthio; arylthio; aralkylthio; cycloalkylthio; heterocyclothio; alkylthiono; arylthiono; aralkylthiono; alkylsulfonyl; arylsulfonyl; aralkylsulfonyl; sulfonamido (e.g., $SO_2NH_2$); substituted sulfonamido; nitro; cyano; carboxy; carbamyl (e.g., $CONH_2$); substituted carbamyl (e.g., —C(=O)NRR' where R and R' are each independently hydrogen, alkyl, aryl, aralkyl and the like); alkoxycarbonyl, aryl, substituted aryl, guanidino, and heterocyclo such as indoyl, imidazolyl, furyl, thienyl, thiazolyl, pyrrolidyl, pyridyl, pyrimidyl and the like. Where applicable, the substituent may be further substituted such as with, alkyl, alkoxy, aryl, aralkyl, halogen, hydroxy and the like.

The terms "alkylaryl" or "arylalkyl" refer to an aryl group with an aliphatic substituent that is bonded to the compound through the aliphatic group. An illustrative example of an alkylaryl or arylalkyl group is benzyl, a phenyl with a methyl group that is bonded to the compound through the methyl group (—$CH_2$Ph where Ph is phenyl).

The term "acyl" refers to —C(=O)R where R is an aliphatic group, preferably a $C_1$–$C_6$ moiety.

The term "alkoxy" refers to —OR wherein O is oxygen and R is an aliphatic group.

The term "aminoalkyl" refers to —$RNH_2$ where R is an aliphatic moiety.

The terms "halogen," "halo", or "halide" refer to fluorine, chlorine, bromine and iodine.

The term "haloalkyl" refers to —RX where R is an aliphatic moiety and X is one or more halogens.

The term "hydroxyalkyl" refers to —ROH where R is an aliphatic moiety.

The term "oxo" refers to a carbonyl oxygen (=O).

In addition to the explicit substitutions at the above-described groups, the inventive compounds may include other substitutions where applicable. For example, the lactone or lactam backbone or backbone substituents may be additionally substituted (e.g., by replacing one of the hydrogens or by derivatizing a non-hydrogen group) with one or more substituents such as $C_1$–$C_5$ aliphatic, $C_1$–$C_5$ alkoxy, aryl, or a functional group. Illustrative examples of suitable functional groups include but are not limited to: acetal, alcohol, aldehyde, amide, amine, boronate, carbamate, carboalkoxy, carbonate, a carbodiimide, carboxylic acid, cyanohydrin, disulfide, enamine, ester, ether, halogen, hydrazide, hydrazone, imide, imido, imine, isocyanate, ketal, ketone, nitro, oxime, phosphine, phosphonate, phosphonic acid, quaternary ammonium, sulfenyl, sulfide, sulfone, sulfonic acid, thiol, and the like.

The term "purified" as used herein to refer to a compound of the present invention, means that the compound is in a preparation in which the compound forms a major component of the composition, such as constituting about 50%, about 60%, about 70%, about 80%, about 90%, about 95% or more by weight of the components in the composition.

The term "subject" as used herein, refers to an animal, preferably a mammal, who has been the object of treatment, observation or experiment and most preferably a human who has been the object of treatment and/or observation.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

The term "composition" is intended to encompass a product comprising the specified ingredients in the specified amounts, as well as any product that results, directly or indirectly, from combinations of the specified ingredients in the specified amounts.

The term "pharmaceutically acceptable salt" is a salt of one or more of the inventive compounds. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include but are not limited to:

acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like.

The term "pharmaceutically acceptable carrier" is a medium that is used to prepare a desired dosage form of the inventive compound. A pharmaceutically acceptable carrier includes solvents, diluents, or other liquid vehicle; dispersion or suspension aids; surface active agents; isotonic agents; thickening or emulsifying agents, preservatives; solid binders; lubricants and the like. Remington's Pharmaceutical Sciences, Fifteenth Edition, E. W. Martin (Mack Publishing Co., Easton, Pa., 1975) and Handbook of Pharmaceutical Excipients, Third Edition, A. H. Kibbe, ed. (Amer. Pharmaceutical Assoc. 2000), both of which are incorporated herein by reference in their entireties, disclose various carriers used in formulating pharmaceutical compositions and known techniques for the preparation thereof.

The term "pharmaceutically acceptable ester" is an ester that hydrolzyes in vivo into a compound of the present invention or a salt thereof. Illustrative examples of suitable ester groups include, for example, those derived from pharmaceutically acceptable aliphatic carboxylic acids such as formates, acetates, propionates, butyrates, acrylates, and ethylsuccinates.

Compounds of the Present Invention

In one aspect of the present invention, the compounds are a 16 membered macrocycle having a conjugated diene. The macrocycle may be a cyclic ester or lactone, a cyclic amide or lactam, or a cyclic thioester.

In another aspect of the present invention, compounds of the following formula

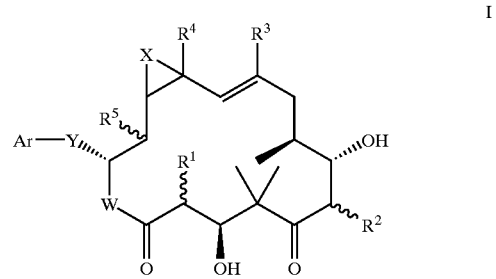

I are provided wherein:

$R^1$, $R^2$, $R^3$, and $R^5$ are each independently hydrogen, $C_1$–$C_{10}$ alkyl, $C_2$–$C_{10}$ alkenyl, $C_2$–$C_{10}$ alkynyl, aryl or alkylaryl;

$R^4$ is hydrogen, halogen, $C_1$–$C_{10}$ alkyl, $C_1$–$C_{10}$ hydroxyalkyl, $C_1$–$C_{10}$ haloalkyl, aryl, —C(=O)$R^6$, —C(=O)O$R^6$, —N$R^6R^7$ where $R^6$ and $R^7$ are each independently hydrogen, $C_1$–$C_{10}$ aliphatic, aryl or alkylaryl;

W is O, N$R^8$ where $R^8$ is hydrogen, $C_1$–$C_{10}$ alkyl, $C_2$–$C_{10}$ alkenyl, $C_2$–$C_{10}$ alkynyl, aryl or alkylaryl;

X is O, $CH_2$ or a carbon-carbon double bond;

Y is absent or a $C_1$–$C_{10}$ alkyl, $C_2$–$C_{10}$ alkenyl, or $C_2$–$C_{10}$ alkynyl; and Ar is aryl; provided that 10,11-dehydroepothilone C is excluded.

In one embodiment, compounds of formula I are provided wherein:

$R^1$, $R^2$, $R^3$, and $R^5$ are each independently hydrogen or $C_1$–$C_5$ alkyl;

$R^4$ is hydrogen, $C_1$–$C_5$ alkyl, $C_1$–$C_5$ hydroxyalkyl, $C_1$–$C_5$ haloalkyl, —C(=O)$R^6$, —C(=O)O$R^6$, —N$R^6R^7$ where $R^6$ and $R^7$ are each independently hydrogen or $C_1$–$C_5$ alkyl;

W is O or N$R^8$ where $R^8$ is hydrogen or $C_1$–$C_5$ alkyl;

X is O, $CH_2$ or a carbon-carbon double bond;

Y is absent or $C_2$–$C_5$ alkenyl; and

Ar is a heteroaryl.

In another embodiment, compound of formula I are provided wherein:

$R^1$, $R^2$, $R^3$, and $R^5$ are each independently hydrogen, methyl or ethyl;
$R^4$ is hydrogen, methyl, ethyl, hydroxymethyl, hydroxyethyl, fluoromethyl or fluoroethyl;
W is O or NH;
X is O, $CH_2$ or a carbon-carbon double bond;
Y is absent or $C_2$–$C_5$ alkenyl; and
Ar is an aryl selected from the group consisting of phenyl, pyridyl, pyridazinyl, pyrimidinyl, pyrazinyl, furyl, thienyl, pyrrolyl, imidazolyl, pyrazolyl, thiazolyl, oxazolyl, quinolyl, isoquinolyl, quinoxalyl, indolyl, benzothiazolyl, benzoxazolyl, benzoimidazolyl, and benzopyrazolyl.

In another embodiment, compound of formula I are provided wherein:

$R^1$, $R^2$, $R^3$, and $R^5$ are each independently hydrogen or methyl;
$R^4$ is hydrogen, methyl, ethyl, or fluoromethyl;
W is O or NH;
X is O, $CH_2$ or a carbon-carbon double bond;
Y is absent or $C_2$–$C_3$ alkenyl; and
Ar is an aryl selected from the group consisting of thiazolyl, oxazolyl, quinolyl, isoquinolyl, quinoxalyl, indolyl, benzothiazolyl, benzoxazolyl, benzoimidazolyl, and benzopyrazolyl.

In another aspect of the present invention, compounds of the following formula

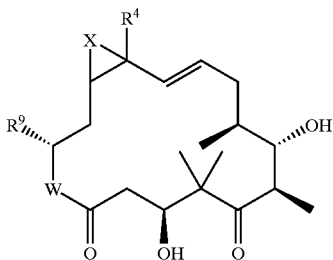

are provided wherein:

W is O or $NR^8$ where $R^8$ is hydrogen or $C_1$–$C_5$ alkyl;
X is O, $CH_2$ or a carbon-carbon double bond;
$R^4$ is hydrogen, $C_1$–$C_5$ alkyl, $C_1$–$C_5$ hydroxyalkyl, $C_1$–$C_5$ haloalkyl, —C(=O)$R^6$, —C(=O)O$R^6$, —$NR^6R^7$ where $R^6$ and $R^7$ are each independently hydrogen or $C_1$–$C_5$ alkyl; and,
$R^9$ is aryl or $R^{11}$CH=C($R^{10}$)— wherein $R^{11}$ is aryl and $R^{10}$ is hydrogen, halide, $C_1$–$C_5$ alkyl, $C_1$–$C_5$ hydroxylalkyl, or $C_1$–$C_5$ haloalkyl.

In another embodiment, compounds of formula II are provided wherein:

W is O or NH; and,
X is $CH_2$ or a carbon-carbon double bond;
$R^4$ is hydrogen, methyl, ethyl, hydroxymethyl, hydroxyethyl, fluoromethyl or fluoroethyl; and,
$R^9$ is a bicyclic heteroaryl or $R^{11}$CH=C($R^{10}$)— wherein $R^{11}$ is 2-methyl-1,3-thiazolinyl, 2-methyl-13, oxazolinyl, 2-hydroxymethyl-1,3-thiazolinyl, or 2-hydroxymethyl-1,3-oxazolinyl and $R^{10}$ is hydrogen or methyl.

In another embodiment, compounds of formula II are provided wherein:

W is O or NH; and,
X is $CH_2$ or a carbon-carbon double bond;
$R^4$ is hydrogen, methyl, ethyl, hydroxymethyl, hydroxyethyl, fluoromethyl or fluoroethyl; and,
$R^9$ is selected from the group consisting of

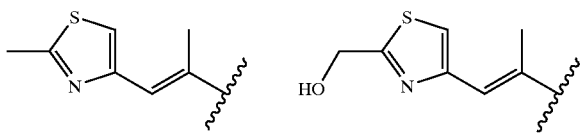

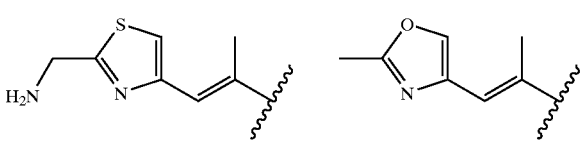

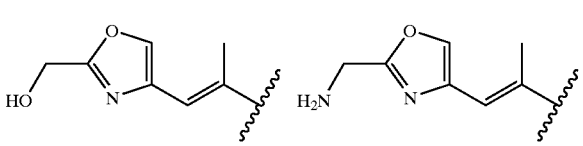

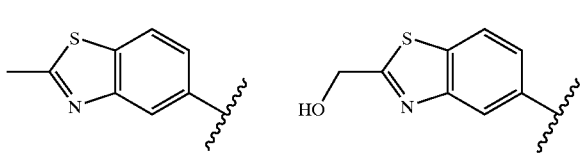

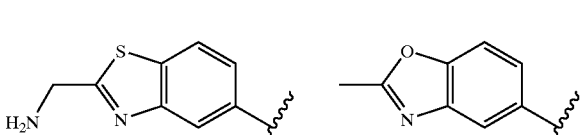

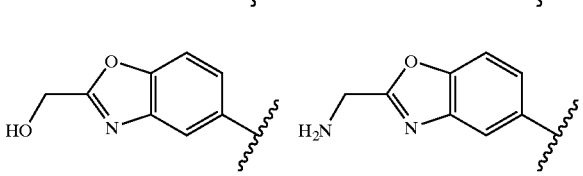

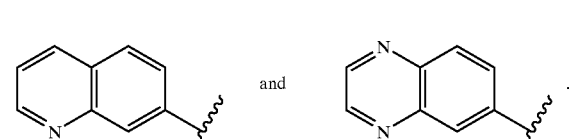

In another aspect of the present invention, compounds of the following formulas

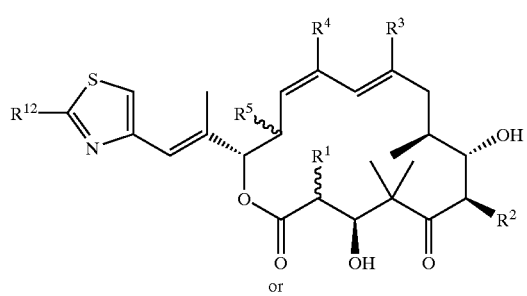

or

-continued

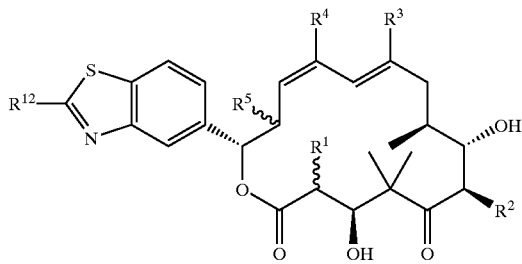

IV

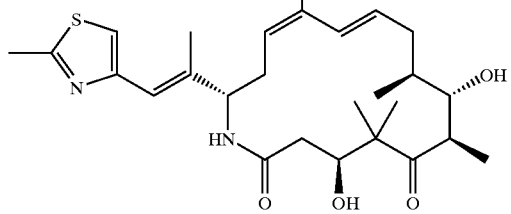

are provided wherein:

R$^1$, R$^2$, R$^3$, and R$^5$ are each independently hydrogen or C$_1$–C$_5$ alkyl; and, R$^4$ is hydrogen, C$_1$–C$_5$ alkyl, C$_1$–C$_5$ hydroxyalkyl, C$_1$–C$_5$ haloalkyl, —C(=O)R$^6$, —C(=O)OR$^6$, —NR$^6$R$^7$ where R$^6$ and R$^7$ are each independently hydrogen or C$_1$–C$_5$ alkyl;

R$^{12}$ is hydrogen, halide, C$_1$–C$_5$ alkyl, C$_1$–C$_5$ hydroxyalkyl, C$_1$–C$_5$ haloalkyl, —(CH$_2$)$_m$C(=O)R$^6$, —(CH$_2$)$_m$C(=O)OR$^6$, —(CH$_2$)$_m$NR$^6$R$^7$ where m is 0, 1 or 2, and R$^6$ and R$^7$ are each independently hydrogen or C$_1$–C$_5$ alkyl; provided that 10,11-dehydroepothilone C is excluded.

In one embodiment, compounds are of formulas III or IV wherein

R$^1$, R$^2$, R$^3$, and R$^5$ are each independently hydrogen, methyl or ethyl;

R$^4$ is methyl, ethyl, hydroxymethyl, fluoromethyl, hydroxyethyl, or fluoroethyl; and, R$^{12}$ is hydrogen, C$_1$–C$_3$ alkyl, C$_1$–C$_3$ hydroxyalkyl, C$_1$–C$_3$ haloalkyl, —(CH$_2$)$_m$C(=O)R$^6$, —(CH$_2$)$_m$C(=O)OR$^6$, —(CH$_2$)$_m$NR$^6$R$^7$ where m is 0 or 1, and R$^6$ and R$^7$ are each independently hydrogen or methyl.

In another embodiment, compounds are of formulas III or IV wherein

R$^1$, R$^3$, and R$^5$ are each hydrogen;

R$^2$ is methyl;

R$^4$ is methyl, ethyl, or fluoromethyl; and,

R$^{12}$ is methyl, hydroxymethyl, fluoromethyl, and aminomethyl.

In another aspect of the present invention, the following compounds are provided:

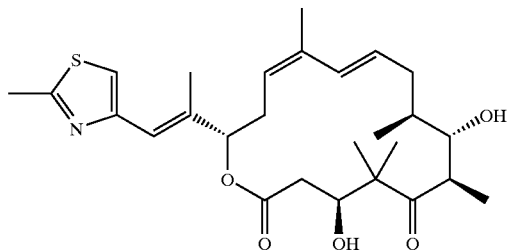

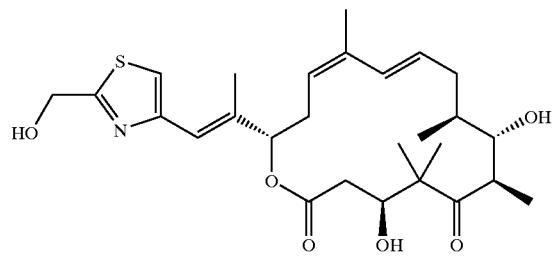

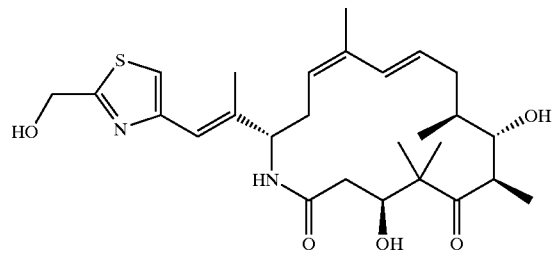

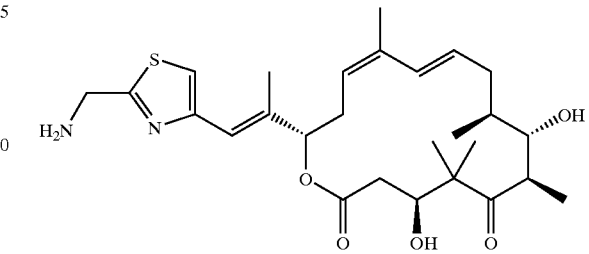

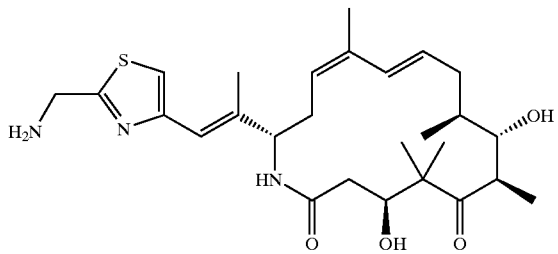

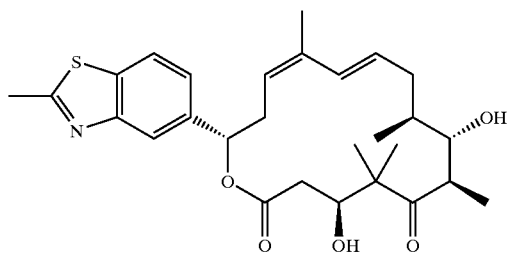

-continued

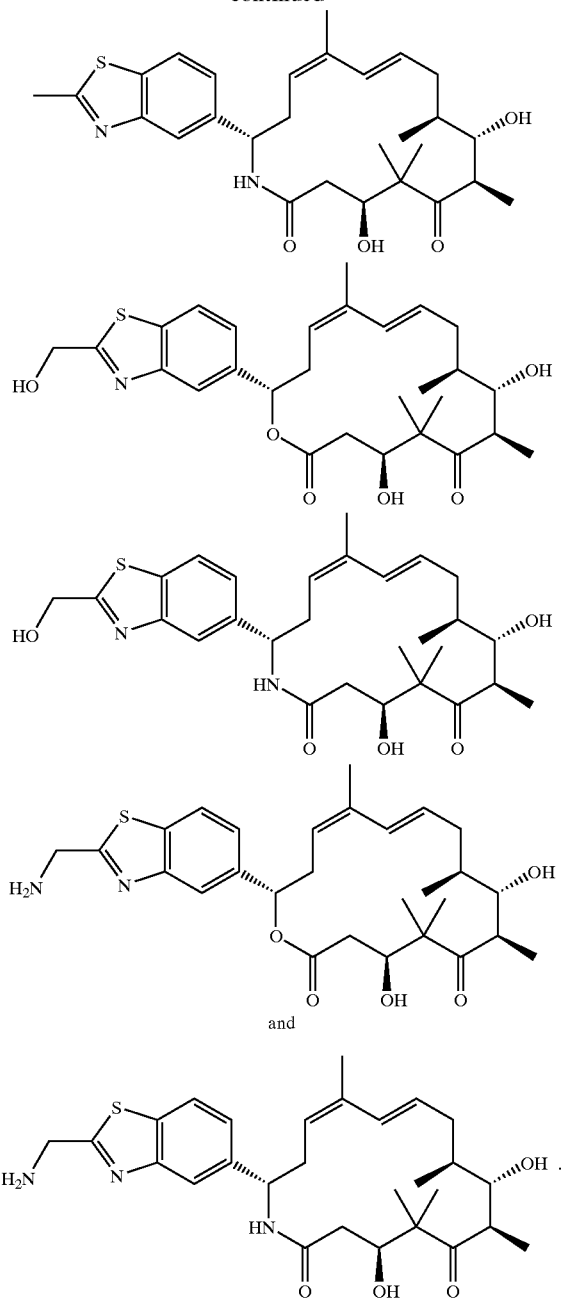

and

The compounds of the present invention are cytotoxic agents and may be used in any suitable manner including but not limited to as anti-cancer agents. An illustrative assay for assessing the degree of cytotoxicy and tubulin polyermization is described in Example 1.

Synthetic Methods

General principles of organic chemistry including functional moieties and reactivity and common protocols are described by for example in Advanced Organic Chemistry 3rd Ed. by Jerry March (1985) which is incorporated herein by reference in its entirety. In addition, it will be appreciated by one of ordinary skill in the art that the synthetic methods described herein may use a variety of protecting groups whether or not they are explicitly described. A "protecting group" as used herein means a moiety used to block functional moiety such as oxygen, sulfur, or nitrogen so that a reaction can be carried out selectively at another reactive site in a multifunctional compound. General principles including specific functional groups and their uses are described for example in T. H. Greene and P. G. M. Wuts, Protective Groups in Organic Synthesis, 3rd edition, John Wiley & Sons, New York (1999).

In one aspect of the present invention, two fragments are coupled together and subsequently cyclized to form 16 membered macrocycles of the present invention. In one embodiment, fragments A and B are joined together under Heck coupling conditions (a palladium catalyst such as (diphenylphosphineferrocenyl)dichloropalladium; a base such as cesium carbonate or 9-borabicyclo[3.3.1]nonane; and triphenylarsine). In another embodiment, fragments A and B' (an alkyne form of fragment B) are joined together under Suzuki coupling reaction conditions. Fragment B' is treated with a borane such as catechol borane or 9-borabicyclo[3.3.1]nonane, and then fragments B' and A, a palladium catalyst such as (diphenylphosphineferrocenyl) dichloropalladium, a base such as cesium carbonate, and triphenylarsine are reacted together. Both methods are illustrated schematically by Scheme 1 where Ar, W, Y, $R^1$, $R^2$, $R^3$, $R^4$, $R^5$ are as described previously and Z is a protected hydroxy group or a protected amino group that is capable of becoming W upon deprotection and cyclization.

SCHEME 1

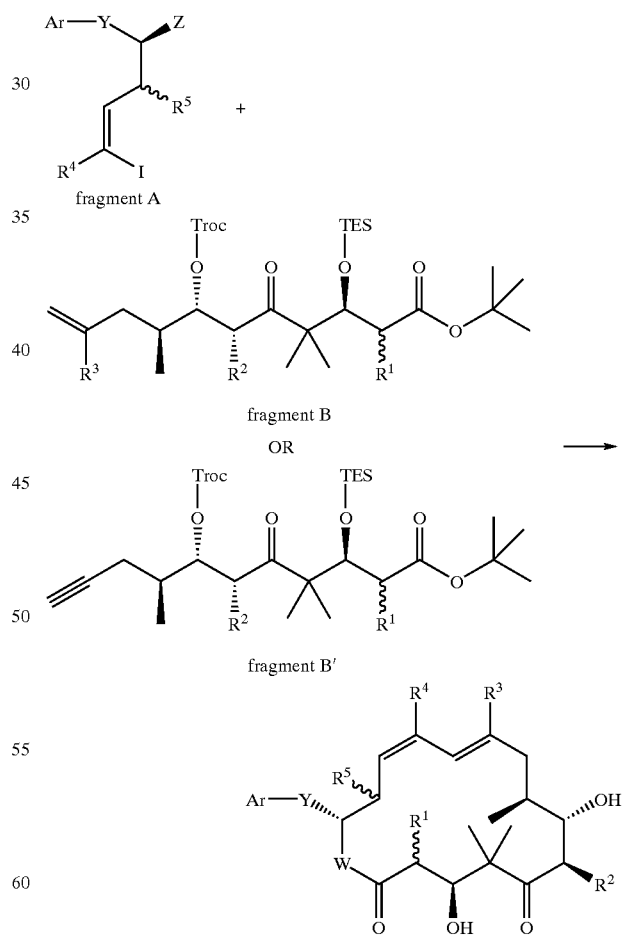

Fragment A is made using a number of methods. Scheme 2A illustrates one embodiment where $R^5$ is hydrogen and Z is a protected hydroxy group and Ar—Y, and $R^4$ are as described previously.

SCHEME 2A

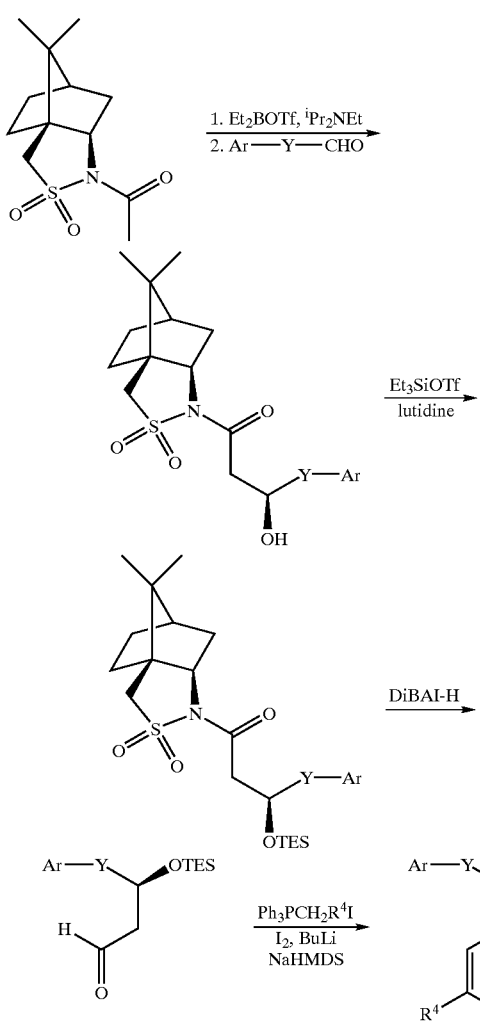

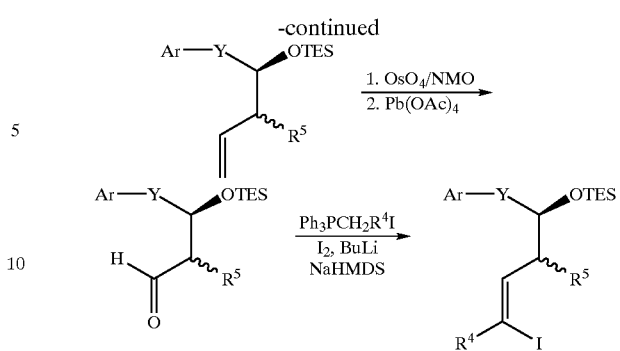

Aldehyde Ar—Y—CHO is treated with diisopinocampheyl-allylborane in a Brown asymmetric allylation. The resulting alcohol is protected with triethylsilyl triflate and lutidine and the alkene is oxidized to an aldehyde. The aldehyde is extended as in Scheme 2A in a Wittig reaction with a phosphonium salt such as iodoethyltriphenylphosphonium iodide prepared in situ from ethyltriphenylphosphonium iodide.

Scheme 3 illustrates another embodiment where Z is a protected amino group and Ar—Y, $R^4$ and $R^5$ are as described previously.

SCHEME 3

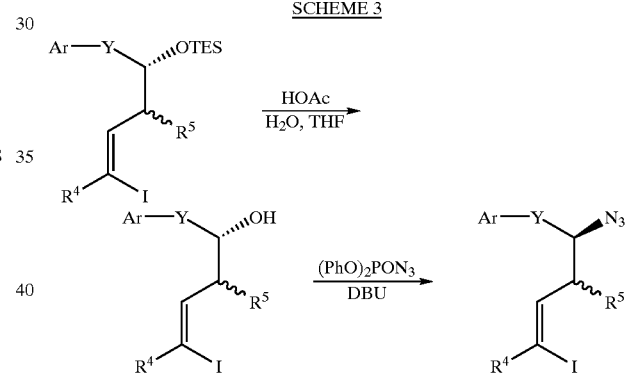

Briefly, the hydroxy protected form of fragment A of the opposite configuration as that described in Schemes 2A and 2B is deprotected and treated with diphenylphosphoryl azide and diazabicycloundecene to form the azido-version of fragment A.

Fragment B where $R^1$ is hydrogen is prepared as described by Scheme 4A.

Briefly, (2R)-N-acetyl-2,10-camphorsultam is treated with a dialkylboron triflate such as diethylborontriflate and a base such as diisopropyl ethylamine and then reacted with Ar—Y—CHO in an Oppolzer aldol condensation. The resulting alcohol is protected by reacting the compound with triethylsilyl triflate and lutidine and reduced to form the aldehyde. Fragment A is formed by extending the aldehyde in a Wittig reaction by treating the aldehyde with a phosphonium salt such as iodoethyltriphenylphosphonium iodide prepared in situ from ethyltriphenylphosphonium iodide.

Scheme 2B illustrates another embodiment where Ar—Y, $R^4$ and $R^5$ are as described previously. This method is preferred where $R^5$ is a non-hydrogen moiety.

SCHEME 2B

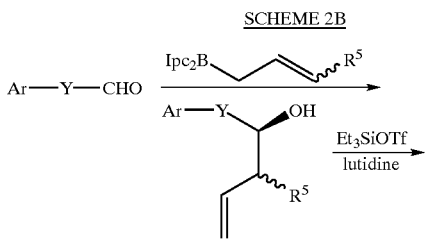

SCHEME 4A

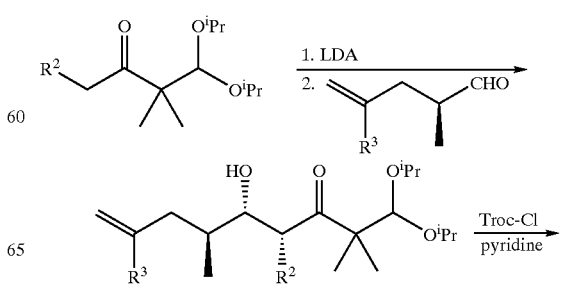

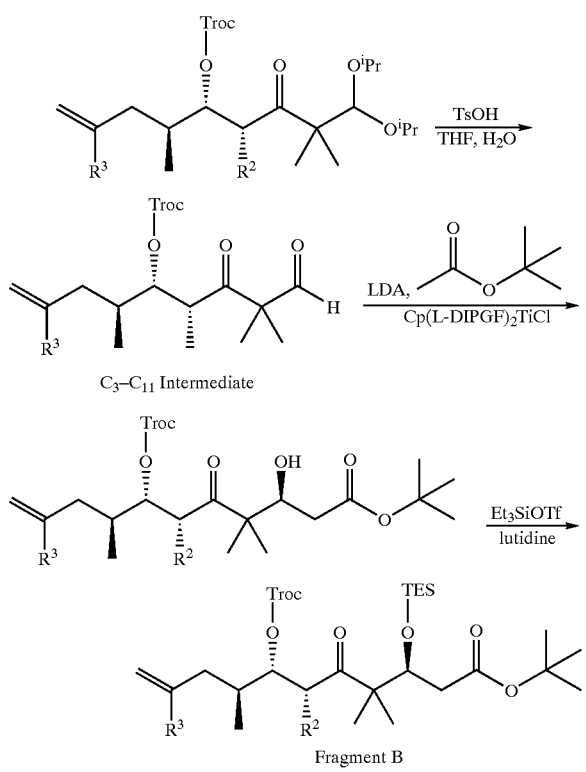

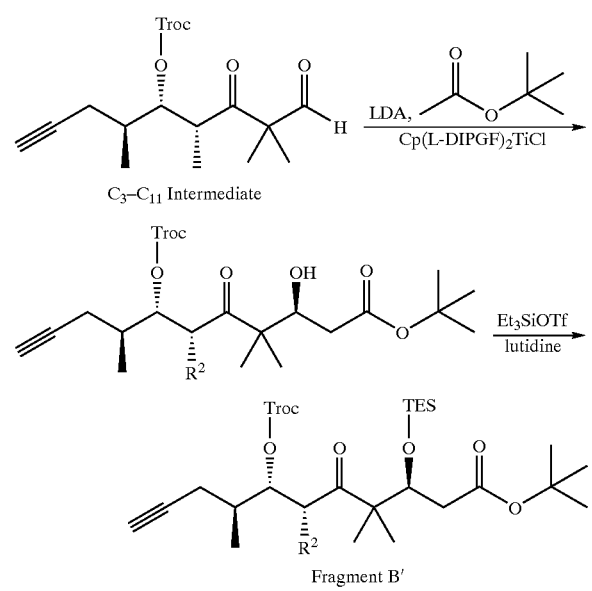

A 1,1-diisopropoxy-2,2-dimethyl-3-alkanone is extended in an aldol condensation reaction. The resulting hydroxyl group is protected with trichloroethoxycarbonyl chloride, and the acetal protecting group is removed to yield a $C_3$–$C_{11}$ Intermediate of fragment B. This intermediate aldehyde is extended in another aldol reaction and protected to yield fragment B.

Fragment B' (where $R^3$ is hydrogen) and where $R^1$ is hydrogen is prepared as described by Scheme 4B.

SCHEME 4B

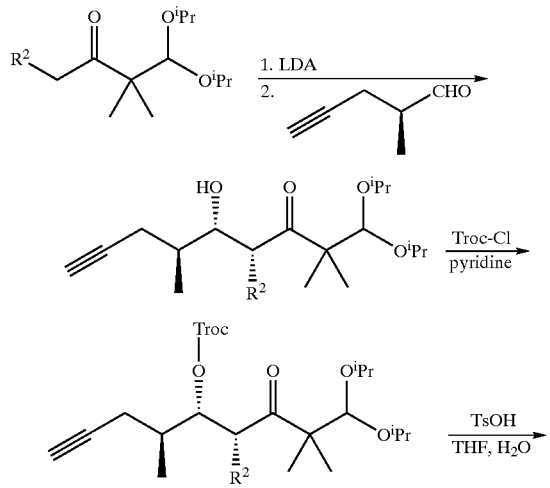

The method is similar to that described by Scheme 4A except that the first aldol reaction is performed using the alkynal

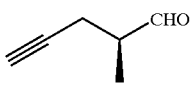

instead of the alkenal

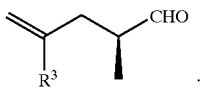

Fragments B and B' where $R^1$ is a non-hydrogen is prepared as described by Scheme 5.

SCHEME 5

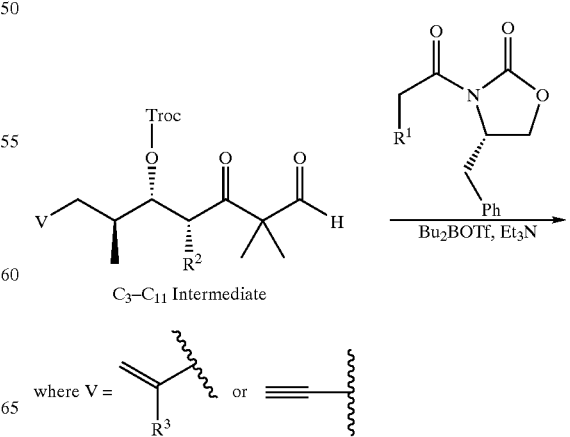

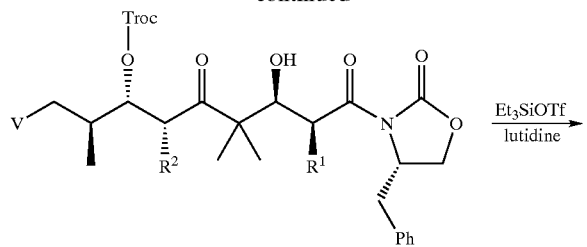

respectively. The $C_3$–$C_{11}$ Intermediate is treated with N-propionyl-benzyloxazolidinone in an Evans aldol reaction. The resulting alcohol is protected with the silyl group and then benzyloxazlidinone is hydrolyzed. Esterification with with tert-butanol yields fragment B.

Fragments A and B can be joined together in a Heck coupling reaction to form a diene as shown by Scheme 6A.

SCHEME 6A

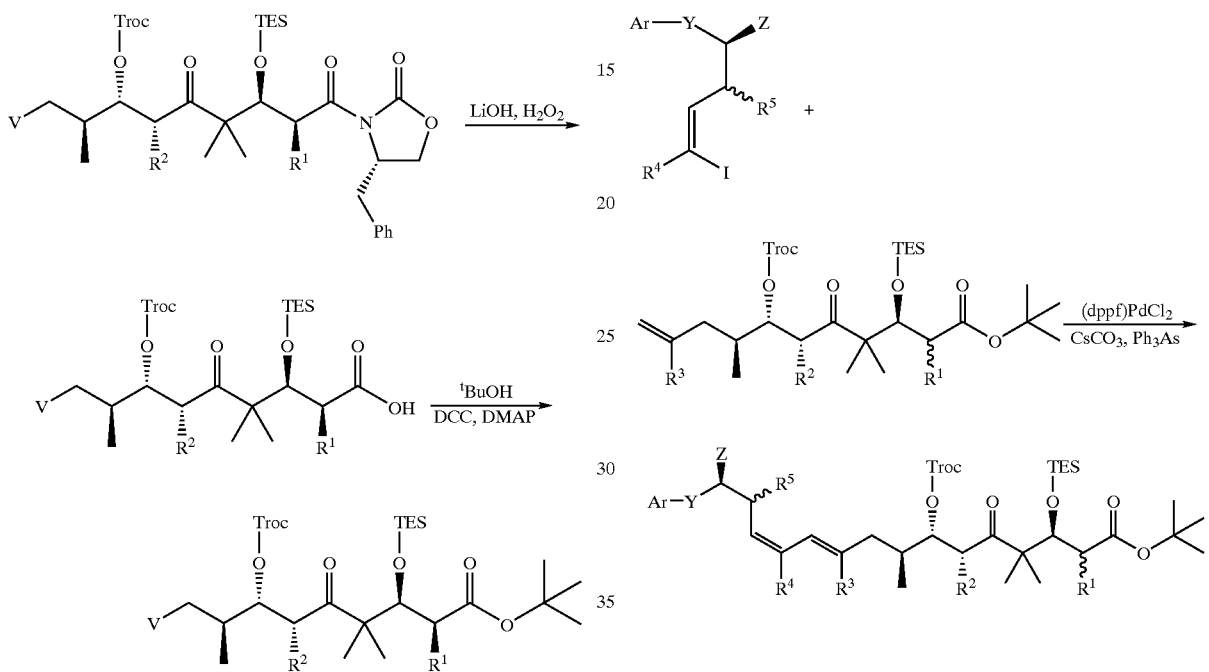

The alkene and alkyne versions of the $C_3$–$C_{11}$ Intermediate are prepared as described by Schemes 4A and 4B Alternatively, Fragments A and B' can be joined together in a Suzuki coupling reaction to form the same diene as shown by Scheme 6B.

SCHEME 6B

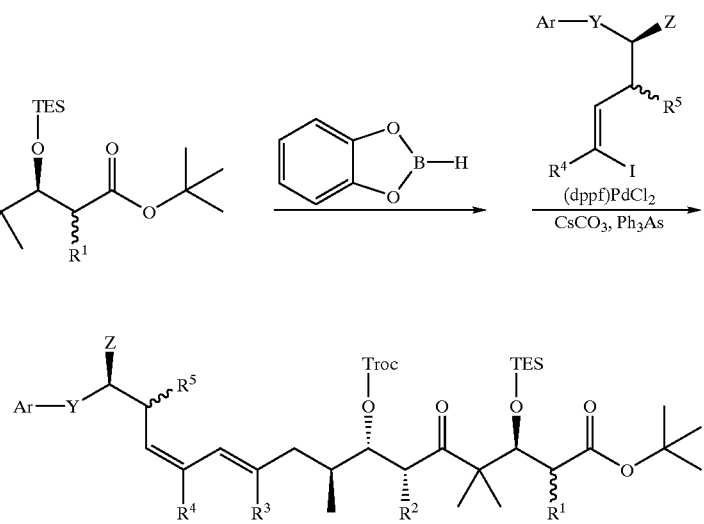

Compounds of the present invention that are cyclic lactones are made from the coupling of fragment A (where Z is a protected hydroxyl group) and fragment B (or B') as illustrated by Scheme 7A.

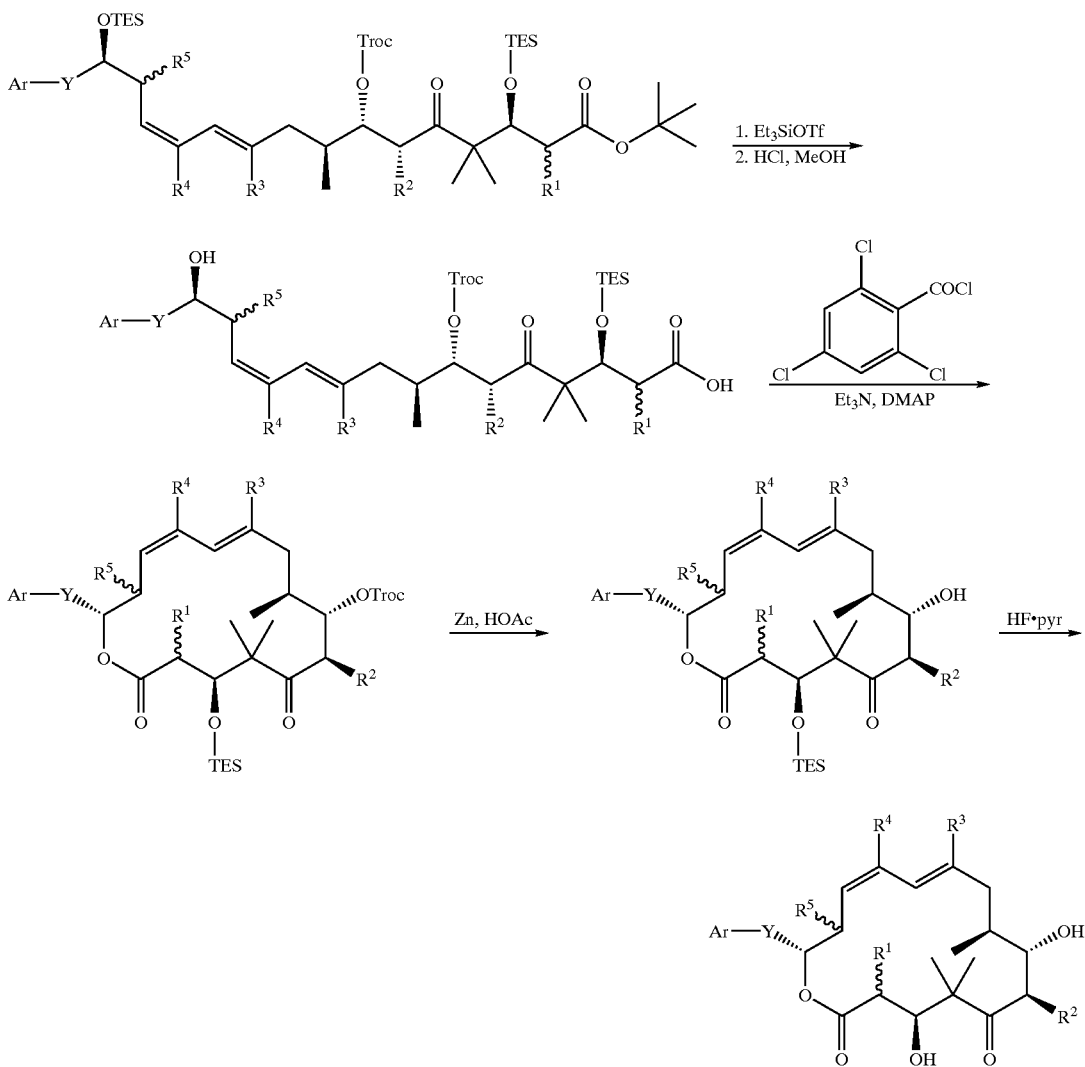

SCHEME 7A

The diene product of either the Heck coupling of fragments A and B or the Suzuki coupling of fragments A and B' is subjected to an ester exchange and then partially deprotected. The resulting product is lactonized and deprotected to yield compounds corresponding to formula I where W is O.

Compounds of the present invention that are cyclic lactams are made from the coupling of fragment A (where Z is a protected amino group such as $N_3$) and fragment B (or B') as illustrated by Schemes 7B and 7C.

SCHEME 7B

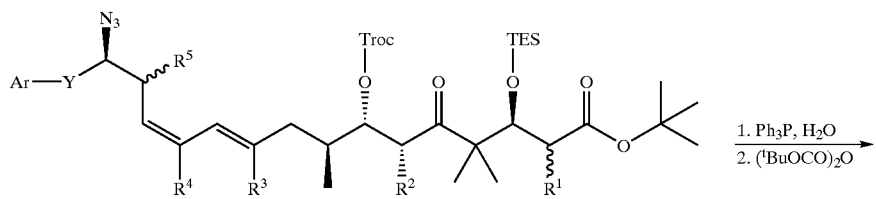

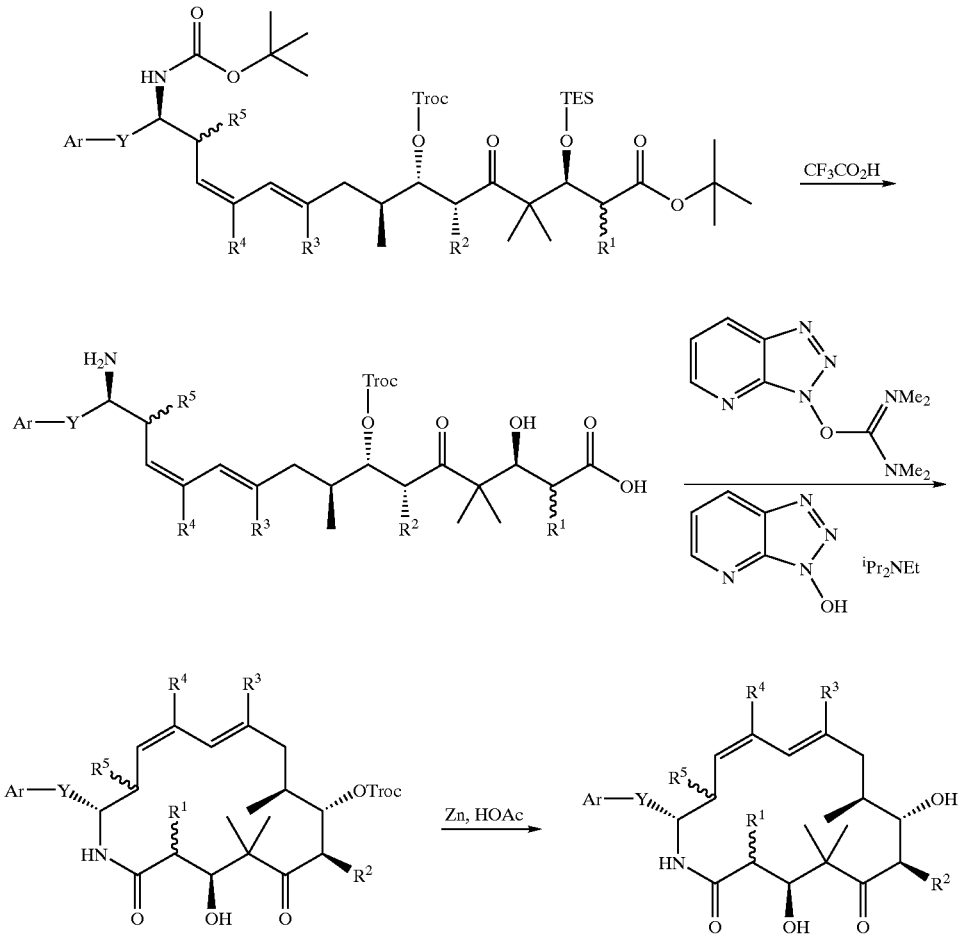

The diene product of either the Heck coupling of fragments A and B or the Suzuki coupling of fragments A and B' is subjected to a Staudinger reduction and the resulting amine is protected. The resulting product is treated with trifluoroacetic acid and then cyclized to form the cyclic lactam. Deprotection of the Troc protecting group yields compounds corresponding to formula I where W is NH.

Methods for making N-alkyl lactam derivatives are described by Scheme 7C.

SCHEME 7C

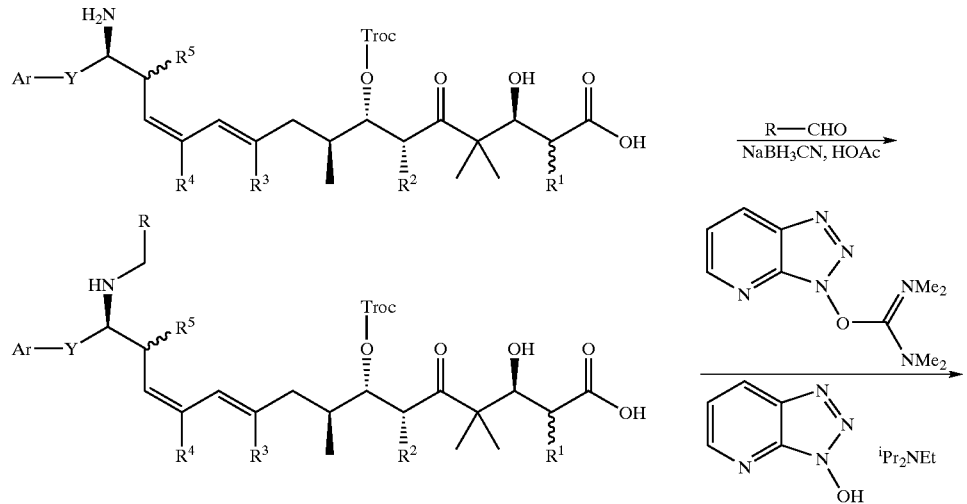

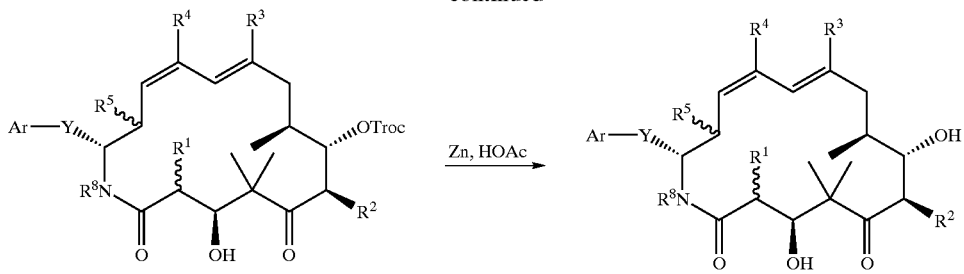

The amino-carboxyacid is made as described by Scheme 7B and then subjected to reductive amination. The resulting product is then cyclized and deprotected to yield compounds corresponding to formula I where W is $NR^8$.

In another aspect of the present invention, the inventive compounds are made from modified versions of fragments A and B (designated as A" and B") using Stille coupling.

SCHEME 8

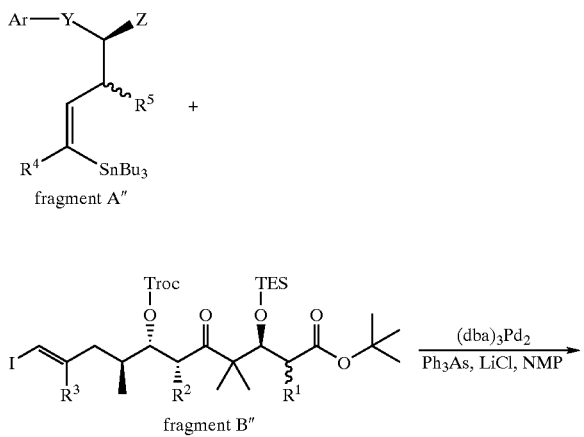

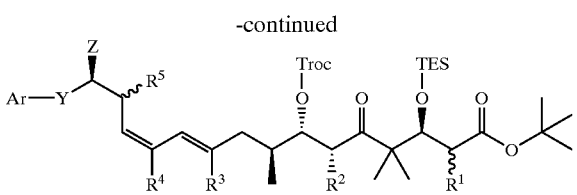

As shown by Scheme 8, the Stille coupling reaction of fragments A" and B" makes the same intermediate as that produced from the previously described Heck coupling or Suzuki coupling reactions. This intermediate can be cyclized under conditions similar to that described by Schemes 7A, 7B, and 7C to make the compounds of the present invention.

Fragment A" can be made as described by Scheme 9 by stannylation of fragment A.

SCHEME 9

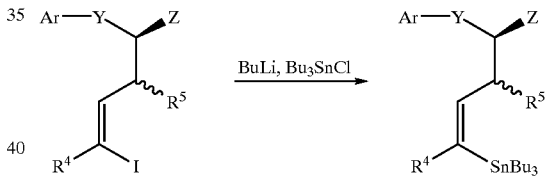

Fragment B" where $R^3$ is hydrogen is made by can be made starting with fragment B'.

SCHEME 10A

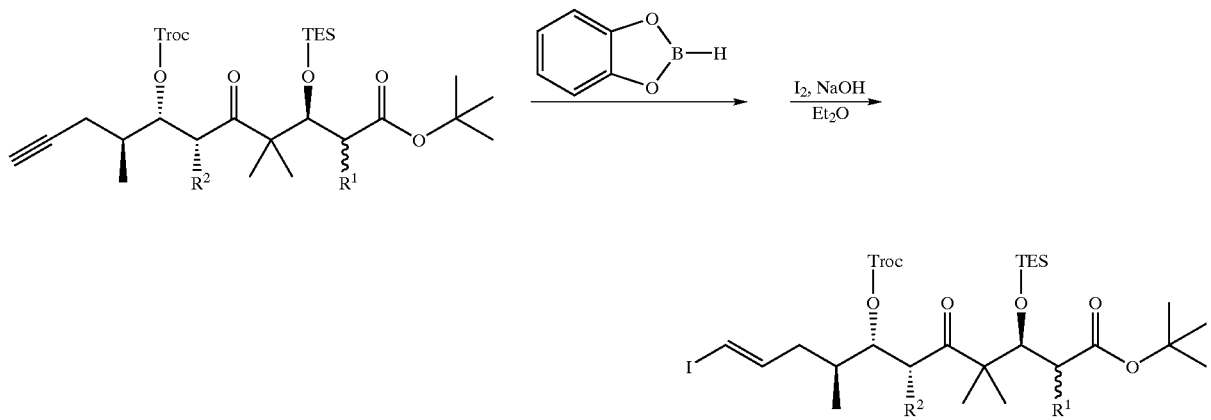

As shown by Scheme 10A, fragment B' is treated with catechol borane in a hydroboration reaction and then iodinated to yield fragment B" where $R^3$ is hydrogen.

Fragment B" where $R^3$ is a non-hydrogen is also made starting from fragment B'

SCHEME 10B

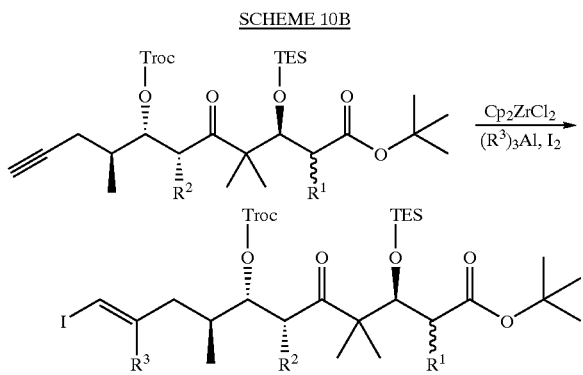

As shown by Scheme 10B, fragment B' is treated wtih zirconocene dichloride and trialkylaluminum in a Schwartz reaction to yield fragment B" where $R^3$ is alkyl.

Biological Methods

In another aspect of the present invention, a subset of the inventive compounds is made using biological methods. In one embodiment, 10,11-dehydroepothilone D, whose structure is shown below,

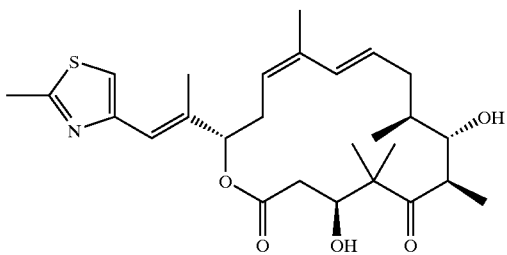

is isolated from a strain of *Myxococcus xanthus*, K111-40-1. This strain expresses the epothilone polyketide synthase but not an active epoK gene product and so produces primarily epothilone D and lesser amounts of epothilone C and 10,11-dehydroepothilone D. Strain K111-40-1 (PTA-2712) was deposited with the American Type Culture Collection ("ATCC"), 10801 University Blvd., Manassas, Va., 20110-2209 USA, on Nov. 21, 2000. In another embodiment, 10,11-dehydroepothilone D may be isolated from *M. xanthus* strain K111-72-4.4 that expresses the epothilone polyketide synthase and contains an epoK gene with an inactivating in frame deletion. Strain K111-72-4.4 (PTA-2713) also was deposited with the ATCC on Nov. 21, 2000. Methods for fermentation of these strains, purification of 10,11-dehydroepothilone D produced by these strains, and recombinant strains that make 10,11-dehydroepothilone D are described in related application U.S. Ser. No. 09/825,876 filed on Apr. 3, 2001, by inventors Robert Arslanian, John Carney and Brian Metcalf entitled EPOTHILONE COMPOUNDS AND METHODS FOR MAKING AND USING THE SAME.

Recombinant techniques can be used to make subset of the compounds of the present invention. These compounds include those with substituents at the C-2 and/or C-6 and/or C-8 and/or C-10 and/or C-14 positions that differ from the naturally occurring epothilones A–D. Procedures for making these kinds of changes in heterologous hosts such as *Myxococcus xanthus, Steptomyces lividans,* and *Pseudomonas fluorescens* are described in U.S. Pat. No. 6,303,342, entitled RECOMBINANT METHODS AND MATERIALS FOR PRODUCING EPOTHILONE AND EPOTHILONE DERIVATIVES, which is incorporated herein by reference. Among other things, the patent provides the nucleotide sequence of the epothilone PKS and modification enzyme genes cloned from *Sorangium cellulosum* SMP44; cosmids containing overlapping fragments of the epothilone PKS and modification enzyme genes; plasmids having the full complement of epoA, epoB, epoC, epoD, epoE, epoF, epoK, and epoL genes; and heterologous host cells for making epothilones and epothilone derivatives. Cosmids, pKOS35-70.1A2 (ATCC 203782), pKOS35-70.4 (ATCC 203781), pKOS35-70.8A3 (ATCC 203783), and pKOS35-79.85 (ATCC 203780); plasmid pair, pKOS039-124R (PTA-926) and pKOS039-126R (PTA-927); and strain K111-32.25 (PTA-1700) derived from *Myxococcus xanthus* containing all the epothilone genes and their promoters, have been deposited with the ATCC on April 14, 2000. Additional procedures for making epothilones in *Myxococcus* are described in: U.S. Ser. No. 09/560,367 filed Apr. 28, 2000; No. 60/232,696, filed Sep. 14, 2000, now lapsed; No. 60/257,517 filed Dec. 21, 2000, now lapsed; and No. 60/269,020, filed Feb. 13, 2001, all of which are entitled PRODUCTION OF POLYKETIDES and are also incorporated herein by reference. Illustrative examples of compounds that may be made using recombinant techniques include: 2-methyl-10,11-dehydroepothilone C or D; 6-desmethyl-10,11-dehydroepothilone C or D; 8-desmethyl-10,11-dehydroepothilone C or D; 10-methyl-10,11-dehydroepothilone C or D; and 14-methyl-10,11-dehydroepothilone C or D.

In another aspect of the present invention, biologically derived strategies are used to modify certain compounds of the present invention regardless of whether the compounds are made biologically or by de novo chemical synthesis. In one embodiment, a microbially-derived hydroxylase is used to hydroxylate a terminal alkane, particularly an alkyl substituent of the thiazole moiety of the inventive compounds. Protocols for effectuating such a transformation are described for example by PCT Publication No. WO 00/39276 which is incorporated herein in its entirety by reference. Example 26 describes in greater detail the hydroxylation of the C-20 methyl of 10,11-dehydroepothilone D to 21-hydroxy-10,11-dehydroepothilone D. This general method can be readily adapted for making corresponding 21-hydroxy derivatives from other compounds of the invention.

In another embodiment, Epo K, a P450 epoxidase that performs the epoxidation reaction in host cells that naturally produce epothilones or another epoxylase may be used to make 12,13-epoxy versions of the compounds of the present invention. A general method for using EpoK for epoxidation is described by Example 5 of PCT publication WO 00/31247 which is incorporated herein by reference. Example 27 describes in greater detail the epoxidation of 10,11-dehydroepothilone D to 10,11-dehydroepothilone B, the general method which can be readily adapted for making corresponding 12,13-epoxide derivatives from other compounds of the invention.

Alternatively, the epoxidation reaction can occur by contacting an epothilone compound containing a double bond at a position that corresponds to the bond between carbon-12 and carbon 13 to a culture of cells that expresses a functional Epo K. Such cells include the myxobacterium *Sorangium*

*cellulosum*. In particularly preferred embodiments, the *Sorangium cellulosum* expresses Epo K but does not contain a functional epothilone polyketide synthase ("PKS") gene. Such strains may be made by mutagenesis where one or more mutations in the epothilone PKS gene render it inoperative. Such mutants can occur naturally (which may be found by screening) or can be directed using either mutagens such as chemicals or irradation or by genetic manipulation. A particularly effective strategy for making strains with an inoperative epothilone PKS is homologous recombination as described by PCT publication WO 00/31247.

Formulation

A composition of the present invention generally comprises an inventive compound and a pharmaceutically acceptable carrier. The inventive compound may be free form or where appropriate as pharmaceutically acceptable derivatives such as prodrugs, and salts and esters of the inventive compound.

The composition may be in any suitable form such as solid, semisolid, or liquid form. See Pharmaceutical Dosage Forms and Drug Delivery Systems, 5$^{th}$ edition, Lippicott Williams & Wilkins (1991) which is incorporated herein by reference. In general, the pharmaceutical preparation will contain one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use. The carriers that can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquified form. In addition, auxiliary stabilizing, thickening, and coloring agents and perfumes may be used.

In one embodiment, the compositions containing an inventive compound are Cremophor®-free. Cremophor® (BASF Aktiengesellschaft) is a polyethoxylated castor oil which is typically used as a surfactant in formulating low soluble drugs. However, because Cremophor® can case allergic reactions in a subject, compositions that minimize or eliminate Cremophor® are preferred. Formulations of epothilone A or B that eliminate Cremophor® are described for example by PCT Publication WO 99/39694 which is incorporated herein by reference and may be adapted for use with the inventive compounds.

Where applicable, the inventive compounds may be formulated as microcapsules and nanoparticles. General protocols are described for example, by Microcapsules and Nanoparticles in Medicine and Pharmacy by Max Donbrow, ed., CRC Press (1992) and by U.S. Pat. Nos. 5,510,118; 5,534,270; and 5,662,883 which are all incorporated herein by reference. By increasing the ratio of surface area to volume, these formulations allow for the oral delivery of compounds that would not otherwise be amenable to oral delivery.

The inventive compounds may also be formulated using other methods that have been previously used for low solubility drugs. For example, the compounds may form emulsions with vitamin E or a PEGylated derivative thereof as described by WO 98/30205 and 00/71163which are incorporated herein by reference. Typically, the inventive compound is dissolved in an aqueous solution containing ethanol (preferably less than 1% w/v). Vitamin E or a PEGylated-vitamin E is added. The ethanol is then removed to form a pre-emulsion that can be formulated for intravenous or oral routes of administration. Another strategy involves encapsulating the inventive compounds in liposomes. Methods for forming liposomes as drug delivery vehicles are well known in the art. Suitable protocols include those described by U.S. Pat. Nos. 5,683,715; 5,415,869, and 5,424,073 which are incorporated herein by reference relating to another relatively low solubility cancer drug taxol and by PCT Publication WO 01/10412 which is incorporated herein by reference relating to epothilone B. Of the various lipids that may be used, particularly preferred lipids for making epothilone-encapsulated liposomes include phosphatidylcholine and polyethyleneglycol-derivitized distearyl phosphatidylethanolamine. Example 28 provides an illustrative protocol for making liposomes containing 10,11-dehydroepothilone D, the general method which can be readily adapted to make liposomes containing other compounds of the present invention.

Yet another method involves formulating the inventive compounds using polymers such as polymers such as biopolymers or biocompatible (synthetic or naturally occurring) polymers. Biocompatible polymers can be categorized as biodegradable and non-biodegradable. Biodegradable polymers degrade in vivo as a function of chemical composition, method of manufacture, and implant structure. Illustrative examples of synthetic polymers include polyanhydrides, polyhydroxyacids such as polylactic acid, polyglycolic acids and copolymers thereof, polyesters polyamides polyorthoesters and some polyphosphazenes. Illustrative examples of naturally occurring polymers include proteins and polysaccharides such as collagen, hyaluronic acid, albumin, and gelatin.

Another method involves conjugating the compounds of the present invention to a polymer that enhances aqueous solubility. Examples of suitable polymers include polyethylene glycol, poly-(d-glutamic acid), poly-(1-glutamic acid), poly-(1-glutamic acid), poly-(d-aspartic acid), poly-(1-aspartic acid), poly-(1-aspartic acid) and copolymers thereof. Polyglutamic acids having molecular weights between about 5,000 to about 100,000 are preferred, with molecular weights between about 20,000 and 80,000 being more preferred and with molecular weights between about 30,000 and 60,000 being most preferred. The polymer is conjugated via an ester linkage to one or more hydroxyls of an inventive epothilone using a protocol as essentially described by U.S. Pat. No. 5,977,163 which is incorporated herein by reference, and by Example 29. Preferred conjugation sites include the hydroxyl off carbon-21 in the case of 21-hydroxy-derivatives of the present invention. Other conjugation sites include the hydroxyl off carbon 3 and the hydroxyl off carbon 7.

In another method, the inventive compounds are conjugated to a monoclonal antibody. This strategy allows the targeting of the inventive compounds to specific targets. General protocols for the design and use of conjugated antibodies are described in Monoclonal Antibody-Based Therapy of Cancer by Michael L. Grossbard, ed. (1998) which is incorporated herein by reference.

The amount of active ingredient that may be combined with the carrier materials to produce a single dosage form will vary depending upon the subject treated and the particular mode of administration. For example, a formulation for intravenous use comprises an amount of the inventive compound ranging from about 1 mg/mL to about 25 mg/mL, preferably from about 5 mg/mL to 15 mg/mL, and more preferably about 10 mg/mL. Intravenous formulations are typically diluted between about 2 fold and about 30 fold with normal saline or 5% dextrose solution prior to use.

Methods to Treat Cancer

In one aspect of the present invention, the inventive compounds are used to treat cancer. In one embodiment, the compounds of the present invention are used to treat cancers of the head and neck which include tumors of the head, neck, nasal cavity, paranasal sinuses, nasopharynx, oral cavity, oropharynx, larynx, hypopharynx, salivary glands, and paragangliomas. In another embodiment, the compounds of the present invention are used to treat cancers of the liver and biliary tree, particularly hepatocellular carcinoma. In another embodiment, the compounds of the present invention are used to treat intestinal cancers, particularly colorectal cancer. In another embodiment, the compounds of the present invention are used to treat ovarian cancer. In another embodiment, the compounds of the present invention are used to treat small cell and non-small cell lung cancer. In another embodiment, the compounds of the present invention are used to treat breast cancer. In another embodiment, the compounds of the present invention are used to treat sarcomas which includes fibrosarcoma, malignant fibrous histiocytoma, embryonal rhabdomysocarcoma, leiomysosarcoma, neurofibrosarcoma, osteosarcoma, synovial sarcoma, liposarcoma, and alveolar soft part sarcoma. In another embodiment, the compounds of the present invention are used to treat neoplasms of the central nervous systems, particularly brain cancer. In another embodiment, the compounds of the present invention are used to treat lymphomas which include Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma.

The method comprises administering a therapeutically effective amount of an inventive compound to a subject suffering from cancer. The method may be repeated as necessary either to contain (i.e. prevent further growth) or to eliminate the cancer. Clinically, practice of the method will result in a reduction in the size or number of the cancerous growth and/or a reduction in associated symptoms (where applicable). Pathologically, practice of the method will produce at least one of the following: inhibition of cancer cell proliferation, reduction in the size of the cancer or tumor, prevention of further metastasis, and inhibition of tumor angiogenesis.

The compounds and compositions of the present invention can be used in combination therapies. In other words, the inventive compounds and compositions can be administered concurrently with, prior to, or subsequent to one or more other desired therapeutic or medical procedures. The particular combination of therapies and procedures in the combination regimen will take into account compatibility of the therapies and/or procedures and the desired therapeutic effect to be achieved.

In one embodiment, the compounds and compositions of the present invention are used in combination with another anti-cancer agent or procedure. Illustrative examples of other anti-cancer agents include but are not limited to: (i) alkylating drugs such as mechlorethamine, chlorambucil, Cyclophosphamide, Melphalan, Ifosfamide; (ii) antimetabolites such as methotrexate; (iii) microtubule stabilizing agents such as vinblastin, paclitaxel, docetaxel, and discodermolide; (iv) angiogenesis inhibitors; (v) and cytotoxic antibiotics such as doxorubicon (adriamycin), bleomycin, and mitomycin. Illustrative examples of other anti-cancer procedures include: (i) surgery; (ii) radiotherapy; and (iii) photodynamic therapy.

In another embodiment, the compounds and compositions of the present invention are used in combination with an agent or procedure to mitigate potential side effects from the inventive compound or composition such as diarrhea, nausea and vomiting. Diarrhea may be treated with antidiarrheal agents such as opioids (e.g. codeine, diphenoxylate, difenoxin, and loeramide), bismuth subsalicylate, and octreotide. Nausea and vomiting may be treated with antiemetic agents such as dexamethasone, metoclopramide, diphenyhydramine, lorazepam, ondansetron, prochlorperazine, thiethylperazine, and dronabinol. For those compositions that includes polyethoxylated castor oil such as Cremophorg®, pretreatment with corticosteroids such as dexamethasone and methylprednisolone and/or $H_1$ antagonists such as diphenylhydramine HCl and/or $H_2$ antagonists may be used to mitigate anaphylaxis. Illustrative formulations for intravenous use and pretreatment regiments are described by Examples 30 and 31 respectively.

Methods of Treating of Non-cancer, Cellular Hyperproliferative Disorders

In another aspect of the present invention, the inventive compounds are used to treat non-cancer disorders that are characterized by cellular hyperproliferation. In one embodiment, the compounds of the present invention are used to treat psoriasis, a condition characterized by the cellular hyperproliferation of keratinocytes which builds up on the skin to form elevated, scaly lesions. The method comprises administering a therapeutically effective amount of an inventive compound to a subject suffering from psoriasis. The method may be repeated as necessary either to decrease the number or severity of lesions or to eliminate the lesions. Clinically, practice of the method will result in a reduction in the size or number of skin lesions, diminution of cutaneous symptoms (pain, burning and bleeding of the affected skin) and/or a reduction in associated symptoms (e.g., joint redness, heat, swelling, diarrhea. abdominal pain, Pathologically, practice of the method will result in at least one of the following: inhibition of keratinocyte proliferation, reduction of skin inflammation (for example, by impacting on: attraction and growth factors, antigen presentation, production of reactive oxygen species and matrix metalloproteinases), and inhibition of dermal angiogenesis.

In another embodiment, the compounds of the present invention are used to treat multiple sclerosis, a condition characterized by progressive demyelination in the brain. Although the exact mechanisms involved in the loss of myelin are not understood, there is an increase in astrocyte proliferation and accumulation in the areas of myelin destruction. At these sites, there is macrophage-like activity and increased protease activity which is at least partially responsible for degradation of the myelin sheath. The method comprises administering a therapeutically effective amount of an inventive compound to a subject suffering from multiple sclerosis. The method may be repeated as necessary to inhibit astrocyte proliferation and/or lessen the severity of the loss of motor function and/or prevent or attenuate chronic progression of the disease. Clinically, practice of the method will result in in improvement in visual symptoms (visual loss, diplopia), gait disorders (weakness, axial instability, sensory loss, spasticity, hyperreflexia, loss of dexterity), upper extremity dysfunction (weakness, spasticity, sensory loss), bladder dysfunction (urgency, incontinence, hesitancy, incomplete emptying), depression, emotional lability, and cognitive impairment. Pathologically, practice of the method will result in the reduction of one or more of the following, such as myelin loss, breakdown of the blood-brain barrier, perivascular infiltration of mononuclear cells, immunologic abnormalities, gliotic scar formation and astrocyte proliferation, metalloproteinase production, and impaired conduction velocity.

In another embodiment, the compounds of the present invention are used to treat rheumatoid arthritis, a multisystem chronic, relapsing, inflammatory disease that sometimes leads to destruction and ankyiosis of affected joints. Rheumatoid arthritis is characterized by a marked thickening of the synovial membrane which forms villous projections that extend into the joint space, multilayering of the synoviocyte lining (synoviocyte proliferation), infiltration of the synovial membrane with white blood cells (macrophages, lymphocytes, plasma cells, and lymphoid follicles; called an "inflammatory synovitis"), and deposition of fibrin with cellular necrosis within the synovium. The tissue formed as a result of this process is called pannus and, eventually the pannus grows to fill the joint space. The pannus develops an extensive network of new blood vessels through the process of angiogenesis that is essential to the evolution of the synovitis. Release of digestive enzymes (matrix metalloproteinases (e.g., collagenase, stromelysin)) and other mediators of the inflammatory process (e.g., hydrogen peroxide, superoxides, lysosomal enzymes, and products of arachadonic acid metabolism) from the cells of the pannus tissue leads to the progressive destruction of the cartilage tissue. The pannus invades the articular cartilage leading to erosions and fragmentation of the cartilage tissue. Eventually there is erosion of the subchondral bone with fibrous ankylosis and ultimately bony ankylosis, of the involved joint.

The method comprises administering a therapeutically effective amount of an inventive compound to a subject suffering from rheumatoid arthritis. The method may be repeated as necessary to accomplish to inhibit synoviocyte proliferation and/or lessen the severity of the loss of movement of the affected joints and/or prevent or attenuate chronic progression of the disease. Clinically, practice of the present invention will result in one or more of the following: (i) decrease in the severity of symptoms (pain, swelling and tenderness of affected joints; morning stiffness, weakness, fatigue, anorexia, weight loss); (ii) decrease in the severity of clinical signs of the disease (thickening of the joint capsule, synovial hypertrophy, joint effusion, soft tissue contractures, decreased range of motion, ankylosis and fixed joint deformity); (iii) decrease in the extra-articular manifestations of the disease (rheumatic nodules, vasculitis, pulmonary nodules, interstitial fibrosis, pericarditis, episcleritis, iritis, Felty's syndrome, osteoporosis); (iv) increase in the frequency and duration of disease remission/symptom-free periods; (v) prevention of fixed impairment and disability; and/or (vi) prevention/attenuation of chronic progression of the disease. Pathologically, practice of the present invention will produce at least one of the following: (i) decrease in the inflammatory response; (ii) disruption of the activity of inflammatory cytokines (such as IL-I, TNFa, FGF, VEGF); (iii) inhibition of synoviocyte proliferation; (iv) inhibition of matrix metalloproteinase activity, and/or (v) inhibition of angiogenesis.

In another embodiment, the compounds of the present invention are used to threat atherosclerosis and/or restenosis, particularly in patients whose blockages may be treated with an endovascular stent. Atheroschlerosis is a chronic vascular injury in which some of the normal vascular smooth muscle cells ("VSMC") in the artery wall, which ordinarily control vascular tone regulating blood flow, change their nature and develop "cancer-like" behavior. These VSMC become abnormally proliferative, secreting substances (growth factors, tissue-degradation enzymes and other proteins) which enable them to invade and spread into the inner vessel lining, blocking blood flow and making that vessel abnormally susceptible to being completely blocked by local blood clotting. Restenosis, the recurrence of stenosis or artery stricture after corrective procedures, is an accelerated form of atherosclerosis.

The method comprises coating a therapeutically effective amount of an inventive compound on a stent and delivering the stent to the diseased artery in a subject suffering from atherosclerosis. Methods for coating a stent with a compound are described for example by U.S. Pat. Nos. 6,156, 373 and 6,120, 847. Clinically, practice of the present invention will result in one or more of the following: (i) increased arterial blood flow; (ii) decrease in the severity of clinical signs of the disease; (iii) decrease in the rate of restenosis; or (iv) prevention/attenuation of the chronic progression of atherosclerosis. Pathologically, practice of the present invention will produce at least one of the following at the site of stent implanataion: (i) decrease in the inflammatory response, (ii) inhibition of VSMC secretion of matrix metalloproteinases; (iii) inhibition of smooth muscle cell accumulation; and (iv) inhibition of VSMC phenotypic dedifferentiation.

Dosage Levels

In one embodiment, dosage levels that are administered to a subject suffering from cancer or a non-cancer disorder characterized by cellular proliferation are of the order from about 1 mg/m$^2$ to about 200 mg/m$^2$ which may be administered as a bolus (in any suitable route of administration) or a continuous infusion (e.g. 1 hour, 3 hours, 6 hours, 24 hours, 48 hours or 72 hours) every week, every two weeks, or every three weeks as needed. It will be understood, however, that the specific dose level for any particular patient depends on a variety of factors. These factors include the activity of the specific compound employed; the age, body weight, general health, sex, and diet of the subject; the time and route of administration and the rate of excretion of the drug; whether a drug combination is employed in the treatment; and the severity of the condition being treated.

In another embodiment, the dosage levels are from about 10 mg/m$^2$ to about 150 mg/m$^2$, preferably from about 10 to about 75 mg/m$^2$ and more preferably from about 15 mg/m$^2$ to about 50 mg/m$^2$ once every three weeks as needed and as tolerated. In another embodiment, the dosage levels are from about 1 mg to about 150 mg/m$^2$, preferably from about 10 mg/m$^2$ to about 75 mg/m$^2$ and more preferably from about 25 mg/m$^2$ to about 50 mg/m$^2$ once every two weeks as needed and as tolerated. In another embodiment, the dosage levels are from about 1 mg/m$^2$ to about 100 mg/m$^2$, preferably from about 5 mg/m$^2$ to about 50 mg/m$^2$ and more preferably from about 10 mg/m$^2$ to about 25 mg/m$^2$ once every week as needed and as tolerated. In another embodiment, the dosage levels are from about 0.1 to about 25 mg/m$^2$, preferably from about 0.5 to about 15 mg/m$^2$ and more preferably from about 1 mg/m$^2$ to about 10 mg/m$^2$ once daily as needed and tolerated.

A detailed description of the invention having been provided above, the following examples are given for the purpose of illustrating the present invention and shall not be construed as being a limitation on the scope of the invention or claims.

EXAMPLE 1

Biological Activity 10,11-Dehydroepothilone D was screened for anticancer activity in four different human tumor cell lines using sulforhodamine B (SRB) assay. 10,11-dehydroepothilone D shows growth inhibitory effect on all four cell lines with $IC_{50}$s ranging from 28 nM to 40 nM. The mechanism of action was determined by a cell-based tubulin polymerization assay which revealed that the compound promotes tubulin polymerization. Human cancer cell lines MCF-7 (breast), NCI/ADR-Res (breast, MDR), SF-268 (glioma), NCI-H460 (lung) were obtained from National Cancer Institute. The cells were maintained in a 5% CO2-humidified atmosphere at 37 degree in RPMI 1640 medium (Life Technology) supplemented with 10% fetal bovine serum (Hyclone) and 2 mM L-glutamine.

Cytotoxicity of 10,11-dehydroepothilone D was determined by SRB assay (Skehan et al., *J. Natl. Cancer Inst.* 82: 1107–1112 (1990) which is incorporated herein by reference). Cultured cells were trypsinized, counted and diluted to the following concentrations per 100 μl with growth medium: MCF-7, 5000; NCI/ADR-Res, 7500; NCI-H460, 5000; and, SF-268, 7500. The cells were seeded at 100 μl/well in 96-well microtiter plates. Twenty hours later, 100 μl of 10,11-dehydroepothilone D (ranging from 1000 nM to 0.001 nM diluted in growth medium) were added to each well. After incubation with the compound for 3 days, the cells were fixed with 100 μl of 10% trichloric acid ("TCA") at 4 degree for 1 hour, and stained with 0.2% SRB/1% acetic acid at room temperature for 20 minutes. The unbound dye was rinsed away with 1% acetic acid, and the bound SRB was then extracted by 200 μl of 10 mM Tris base. The amount of bound dye was determined by OD 515 nm, which correlates with the total cellular protein contents. The data were then analyzed using Kaleida Graph program and the $IC_{50}$'s calculated. Epothione D that was chemically synthesized was tested in parallel for comparison.

For tubulin polymerization assay, MCF-7 cells were grown to confluency in 35 mm-culture dishes and treated with 1 μM of either 10,11-dehydroepothilone D or epothilone D for 0, 1 or 2 hours at 37 degree (Giannakakou et al., *J. Biol. Chem.* 271:17118–17125 (1997); *Int. J. Cancer* 75: 57–63 (1998) which are incorporated herein by reference). After washing the cells twice with 2 ml of PBS without calcium or magnesium, the cells were lysed at room temperature for 5–10 minutes with 300 μl of lysis buffer (20 mM Tris, PH 6.8, 1 mM $MgCl_2$, 2 mM EGTA, 1% Triton X-100, plus protease inhibitors). The cells were scraped and the lysates transferred to 1.5-ml Eppendof tubes. The lysates were then centrifuged at 18000 g for 12 minutes at room temperature. The supernatant containing soluble or unpolymerized (cytosolic) tubulin were separated from pellets containing insoluble or polymerized (cytoskeletal) tubulin and transferred to new tubes. The pellets were then resuspended in 300 μl of lysis buffer. Changes in tubulin polymerization in the cell were determined by analyzing same volume of aliquots of each sample with SDS-PAGE, followed by immunoblotting using an anti-tubulin antibody (Sigma).

The results of several experiments showed that 10,11-dehydroepothilone D (designated as "Epo490") has an $IC_{50}$ in the range of 28 nM to 40 nM against four different human tumor cells lines.

TABLE 1

| Cell lines | EpoD (nM) N = 3 | Epo490 (nM) N = 2 |
| --- | --- | --- |
| MCF-7 | 21 ± 10 | 28 ± 8 |
| NCI/ADR | 40 ± 12 | 35 ± 9 |

TABLE 1-continued

| Cell lines | EpoD (nM) N = 3 | Epo490 (nM) N = 2 |
| --- | --- | --- |
| SF-268 | 34 ± 8 | 40 ± 5 |
| NCI-H460 | 30 ± 2 | 34 ± 1 |

Tubulin polymerization assays reveal that 10,11-dehydroepothilone D has the same mechanism of action as epothilone D. In MCF-7 cells, 10,11-dehydroepothilone D strongly promoted tubulin polymerization at the conditions tested, with similar kinetics and effect as epothilone D. Other compounds of the invention may be tested in a similar manner by replacing the compound of interest for 10,11-dehydroepothilone D.

EXAMPLE 2

(5S)-2-iodo-5-(6-quinolyl)-5-(triethylsilyloxy)-2-pentene

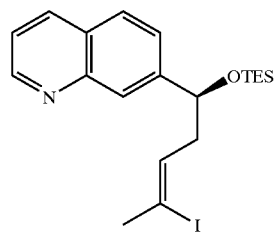

(a) (2R)-N-[(3S)-3-hydroxy-3-(6-quinolyl)propionyl]-2,10-camphorsultam

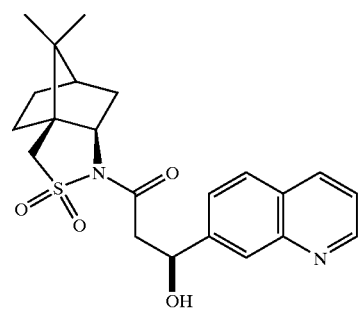

A 1.0 solution of diethylboron triflate in $CH_2Cl_2$ (110 mL) is added slowly to a 0° C. solution of 25.7 g of (2R)-N-acetyl-2,10-camphorsultam (Oppolzer et al. 1992, *Tetrahedron Letters* 33, 2439) in 250 mL of $CH_2Cl_2$. A solution of diisopropylethylamine (15 mL) in 75 mL of $CH_2Cl_2$ is then added dropwise over 20 minutes at 0° C., and the mixture is then cooled to −78° C. A solution of quinoline-6-carboxaldehyde (15.7 g) in 100 mL of $CH_2Cl_2$ is then added at such a rate as to keep the reaction temperature below −70° C. After an additional 2 hours, the mixture is warmed to ambient temperature and quenched by addition of 100 mL of 3:1 tetrahydrofuran/water and 750 mL of sat. aq. $NH_4Cl$. The mixture is concentrated to a slurry, then diluted with water, adjusted to pH 8, and extracted with ethyl acetate. The extract is washed sequentially with water and brine, then dried over $MgSO_4$, filtered, and evaporated to yield the crude adduct. Purification by silica gel chromatography yields pure (2R)-N-[3-hydroxy-3-(6-quinolyl)propionyl] bornane-2,10-camphorsultam.

(b) (2R)-N-[(3S)-3-(triethylsilyloxy)-3-(6-quinolyl)propionyl]-2,10-camphorsultam

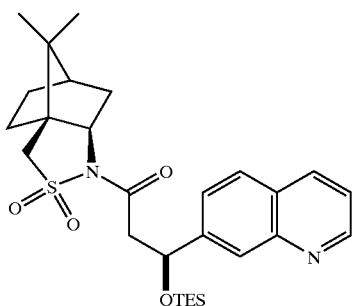

A solution of (2R)-N-[3-hydroxy-3-(6-quinolyl)propionyl]-2,10-camphorsultam (41.4 gm) in 250 mL of CH$_2$Cl$_2$ is cooled on ice and treated with 2,6-lutidine (13 gm) and triethylsilyl trifluoromethanesulfonate (29 gm). After stirring for 12 hours, the mixture is washed with water and dried over MgSO$_4$, filtered, and evaporated to yield the crude product. Purification by silica gel chromatography yields pure (2R)-N-[3-(triethylsilyloxy)-3-(6-quinolyl)propionyl]-2,10-camphorsultam.

(c) (3S)-3-(triethylsilyloxy)-3-(6-quinolyl)propanal

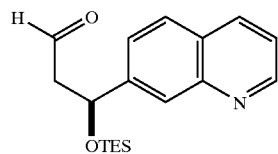

A solution of (2R)-N-[3-(triethylsilyloxy)-3-(6-quinolyl)propionyl]bornane-10,2-sultam (52.8 gm) in 1000 mL of CH$_2$Cl$_2$ is cooled to −78° C, and a 1.0 M solution of diisobutylaluminum hydride in hexane is added dropwise so as to keep the reaction temperature below −65° C. The mixture is stirred for an additional 6 hours at −78° C., then is quenched by addition of sat. aq. NH$_4$Cl and allowed to warm to ambient temperature. The mixture is washed with brine, and the organic phase is dried over MgSO$_4$, filtered, and evaporated. The product is purified by silica gel chromatography.

(d) (5S)-2-iodo-5-(6-quinolyl)-5-(triethylsilyloxy)-2-pentene

A suspension of ethyltriphenylphosphonium iodide (7.9 gm) in 150 mL of tetrahydrofuran is treated with a 2.5 M solution of n-butyllithium (7.17 mL) at ambient temperature. The resulting red solution is transferred via cannula into a vigorously stirred solution of iodine (4.54 gm) in 150 mL of tetrahydrofuran cooled to −78° C. The resulting suspension is stirred for 5 minutes, then gradually warmed to −30° C. A 1.0 M solution of sodium hexamethyldisilazide (17.3 mL) is then added dropwise to form a red solution. A solution of (3S)-3-(triethylsilyloxy)-3-(6-quinolyl)propanal (1.9 gm) in 10 mL of tetrahydrofuran is then added dropwise, and stirring is continued at −30° C. for 30 minutes. The mixture is diluted with ether, filtered through a pad of Celite, and concentrated. The product is purified by flash chromatography on silica gel.

EXAMPLE 3

(5S)-2-iodo-5-(2-methylbenzothiazol-5-yl)-5-(triethylsilyloxy)-2-pentene

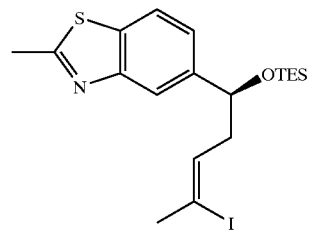

Is prepared according to the method of Example 2, replacing quinoline-6-carboxaldehyde with 2-methylbenzothiazole-5-carboxaldehyde.

EXAMPLE 4

(5S)-2-iodo-6-methyl-7-(2-methylthiazol-4-yl)-5-triethylsilyloxy)-2,6-heptadiene (Fragment A: ArY/R$^9$=(2-methylthiazol-4-yl) propen-2-yl,R$^5$=H,R$^4$=Me)

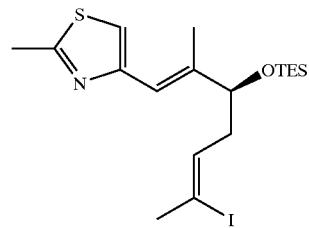

Is prepared according to the method of Example 2, replacing quinoline-6-carboxaldehyde with 2-methyl-3-(2-methylthiazol-4-yl)propenal.

EXAMPLE 5

(6S)-3-iodo-6-(6-quinolyl)-6-(triethylsilyloxy)-3-hexene

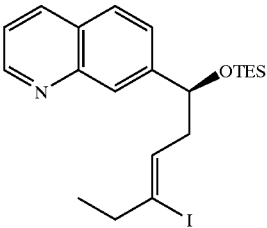

A suspension of propyltriphenylphosphonium iodide (8.2 gm) in 150 mL of tetrahydrofuran is treated with a 2.5 M solution of n-butyllithium (7.17 mL) at ambient temperature. The resulting red solution is transferred via cannula into a vigorously stirred solution of iodine (4.54 gm) in 150 mL of tetrahydrofuran cooled to −78° C. The resulting suspension is stirred for 5 minutes, then gradually warmed to −30° C. A 1.0 M solution of sodium hexamethyldisilazide (17.3 mL) is then added dropwise to form a red solution. A solution of (3S)-3-(triethylsilyloxy)-3-(6-quinolyl)propanal(1.9 gm) in 10 mL of tetrahydrofuran is then added dropwise, and stirring is continued at −30° C. for 30 minutes. The mixture is diluted with ether, filtered through a pad of Celite, and concentrated. The product is purified by flash chromatography on silica gel.

EXAMPLE 6

(5S)-2-iodo-6-methyl-7-(2-(2,2,2-trichloroethoxycarbonyloxy)methylthiazol-4-yl)-5-(triethylsilyloxy)-2,6-heptadiene

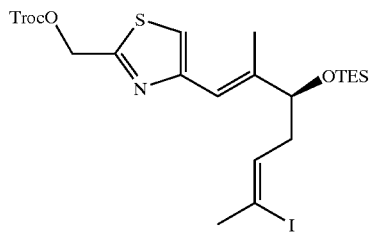

(a) ethyl 2-(2,2,2-trichloroethoxycarbonyloxymethyl)thiazole-4-carboxylate

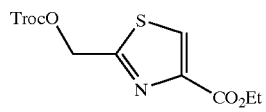

To a solution of ethyl 2-(hydroxymethyl)-thiazole-4-carboxylate 33 (38.4 g) and pyridine (41 mL) in 100 mL of $CH_2Cl_2$ is slowly added 2,2,2-trichloroethyl chloroformate (32 mL, 0.23 mol) at 0° C. After the resulting mixture is stirred for 30 minutes, the reaction is quenched by the addition of 10% aq NaHCO3. The organic layer is separated, and the aqueous layer is extracted with $CH_2Cl_2$. The combined organic extracts are washed with 2 N HCl, 10% aq $NaHCO_3$, and brine, dried ($Na_2SO_4$), and concentrated. The residue is then recrystallized in ethanol (50 mL) to yield a light yellow solid. The mother liquor is concentrated and chromatographed to afford an additional amount of product.

(b) 2-(2,2,2-trichloroethoxycarbonyloxymethyl)thiazole-4-carboxaldehyde

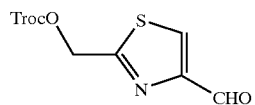

To a solution of ethyl 2-(2,2,2-trichloroethoxycarbonyloxymethyl)thiazole-4-carboxylate (23 g) in $CH_2Cl_2$ (200 mL) is added a solution of diisobutylaluminum hydride (1.0 M in $CH_2Cl_2$, 120 mL) at −78° C. over 30 minutes. The resulting mixture is kept at −78 ° C. for 10 hours. The excess hydride is quenched with acetic acid (5 mL) and the reaction is warmed to ambient temperature, and the mixture is stirred with sat. aq. Rochelle's salt (150 mL) until the suspension clears. The organic layer is washed with 10% aq $NaHCO_3$ and brine, dried ($Na_2SO_4$), filtered, and concentrated. Purification by column chromatography on $SiO_2$ (toluene/ethyl acetate, 6:1) affords the product as a light yellow syrup.

(c) 2-methyl-3-(2-(2,2,2-trichloroethoxycarbonyloxymethyl)thiazol-4-yl)propenal

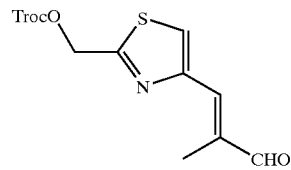

A mixture of 2-(2,2,2-trichloroethoxycarbonyloxymethyl)thiazole-4-carboxaldehyde (21.0 g) and 2-(triphenylphosphoranylidene)propionaldehyde (20.6 g) in 300 mL of benzene is heated at reflux for 3 hours, then cooled to ambient temperature and concentrated. Purification by flash column chromatography on SiO2 (hexanes/ethyl acetate, 4:1) yields the product as a clear oil.

(d) (4S)-4-hydroxy-5-methyl-6-(2-(2,2,2-trichloroethoxycarbonyloxymethyl)-thiazol-4-yl)-1,5-hexadiene

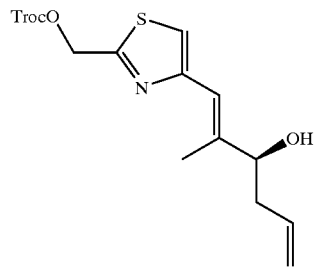

A solution of 2-methyl-3-(2-((2,2,2-trichloroethoxycarbonyloxymethyl)thiazol-4-yl)propenal (9.20 g) in 50 mL of anhydrous ether is cooled to −100° C. A pentane solution of (+)-diisopinocampheylallylborane (1.5 equiv) is added dropwise to the vigorously stirred aldehyde solution. After the addition is complete, the reaction mixture is stirred for 1.5 hours and warmed to −50° C. A solution of 30% aq H2O2 (20 mL) and 10% aq NaHCO3 (50 mL) is added, and the resulting turbid mixture is stirred at 25° C. for 8 hours. The organic layer is separated, and the aqueous layer is extracted with ether. The combined organic layers are washed with satd aq $Na_2S_2O_3$ and brine, dried ($MgSO_4$), filtered, and concentrated. Purification by flash column chromatography on $SiO_2$ (hexanes/ethyl acetate, 10:1) affords the alcohol as a clear oil.

(e) (4S)-4-(triethylsilyloxy)-5-methyl-6-(2-(2,2,2-trichloroethoxycarbonyloxymethyl)-thiazol-4-yl)-1,5-hexadiene

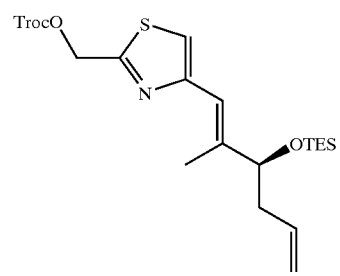

Triethylsilyl trifluromethanesulfonate (15 mL) is added dropwise to a −78° C. solution of (4S)-4-hydroxy-5-methyl-6-(2-(2,2,2-trichloroethoxycarbonyloxymethyl)thiazol-4-yl)-1,5-hexadiene (7.65 g) and 2,6-lutidine (10 mL) in 50 mL of $CH_2Cl_2$. After the addition, the reaction mixture is allowed to warm to ambient temperature and is stirred for 5

39 hours. The reaction mixture is poured into 2 N HCl and extracted with ether. The combined organic layers were washed with 10% aq NaHCO₃ and brine, dried (Na₂SO₄), filtered, and concentrated. Flash chromatography on SiO₂ (hexanes/ethyl acetate, 20:1) provides the product as a colorless oil.

(f) (3S)-3-(triethylsilyloxy)-4-methyl-5-(2-(2,2,2-trichloroethoxycarbonyloxy-methyl)-thiazol-4-yl)-pent-4-enal

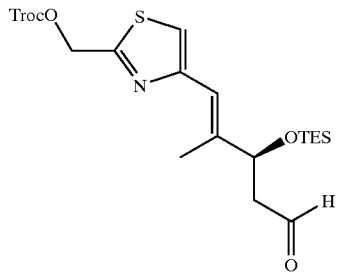

Osmium tetraoxide (1 wt % in THF, 20.3 mL) is added to a mixture of (4S)-4-(triethylsilyloxy)-5-methyl-6-(2-(2,2,2-trichloroethoxycarbonyloxymethyl)-thiazol-4-yl)-1,5-hexadiene (20.6 g), H₂O (21 mL), and N-methylmorpholine N-oxide (50% in THF, 10 mL, 0.048 mol) in tert-butanol (155 mL) at 0° C. After the resulting mixture is stirred for 12 hours, Na₂SO₃ (10 g) and water (5 mL) are added. The resulting solution is stirred at 25° C. for 30 minutes and then extracted with ether. The combined extracts are washed with brine, dried (Na₂SO₄), filtered, and concentrated. Purification by flash chromatography on SiO₂ provides a 1:1 diastereomeric mixture of the diol as a colorless, viscous oil. Lead tetraacetate (19.1 g) is added portionwise over 5 minutes to a suspension of the diol (18.0 g) and Na₂CO₃ (8.67 g) in 500 mL of benzene at 0° C. After stirring for 15 minutes, the mixture is filtered through a SiO₂ pad to afford the aldehyde product. The product is directly subjected to the next reaction.

(g) (5S)-2-iodo-6-methyl-7-(2-(2,2,2-trichloroethoxycarbonyloxy)methylthiazol-4-yl)-5-(triethylsilyloxy)-2,6-heptadiene To a suspension of ethyltriphenylphosphonium iodide (7.90 g) in THF (150 mL) is added n-butyllithium (7.17 mL, 2.5 M in hexane) at ambient temperature. After disappearance of the solid material, the red solution is cannulated into a vigorously stirred solution of iodine (4.54 g) in THF (150 mL) at −78° C. The resulting dark brown suspension is stirred for 5 minutes and allowed to warm gradually to −30° C. A solution of sodium hexamethyldisilazide (17.3 mL, 1.0 M in THF) is added dropwise to afford a dark red solution. A solution of (3S)-3-(triethylsilyloxy)-4-methyl-5-(2-(2,2,2-trichloroethoxy-carbonyloxy-methyl)-thiazol-4-yl))-pent-4-enal (3.10 g) in THF (10 mL) is slowly added, and stirring is continued at −30° C. for 30 minutes. The reaction mixture is diluted with pentane (100 mL), filtered through a pad of Celite, and concentrated. Purification by flash column chromatography on SiO₂ (hexane/ethyl acetate, 15:1) affords the vinyl iodide as a yellow syrup.

40

EXAMPLE 7

(4S,5S)-2-iodo-4,6-dimethyl-7-(2-methylthiazol-4-yl)-5-(triethylsilyloxy)-2,6-heptadiene

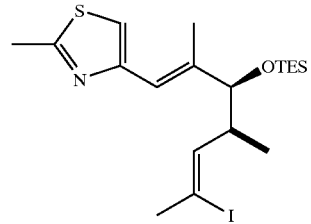

(a) (3S,4S)-4-hydroxy-3,5-dimethyl-6-(2-methylthiazol-4-yl))-1,5-hexadiene

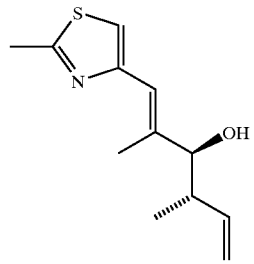

A solution of 2-methyl-3-(2-methylthiazol-4-yl))propenal (4.3 g) in 50 mL of anhydrous ether is cooled to −100° C. A pentane solution of (+)-diisopinocampheyl-trans-crotylborane (1.5 equiv) is added dropwise to the vigorously stirred aldehyde solution. After the addition is complete, the reaction mixture is stirred for 1.5 hours and warmed to −50° C. A solution of 30% aq H2O2 (20 mL) and 10% aq NaHCO3 (50 mL) is added, and the resulting turbid mixture is stirred at 25° C. for 8 hours. The organic layer is separated, and the aqueous layer is extracted with ether. The combined organic layers are washed with satd aq Na₂S₂O₃ and brine, dried (MgSO₄), filtered, and concentrated. Purification by flash column chromatography on SiO₂ (hexanes/ethyl acetate, 10:1) affords the alcohol as a clear oil.

(b) (3S,4S)-4-(triethylsilyloxy)-3,5-dimethyl-6-(2-methylthiazol-4-yl))-1,5-hexadiene

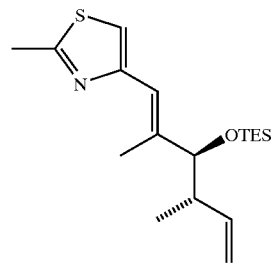

Triethylsilyl trifluromethanesulfonate (15 mL) is added dropwise to a −78° C. solution of (3S,4S)-4-hydroxy-3,5-dimethyl-6-(2-methylthiazol-4-yl)-1,5-hexadiene (4.3 g) and 2,6-lutidine (10 mL) in 50 mL of CH₂Cl₂. After the addition, the reaction mixture is allowed to warm to ambient temperature and is stirred for 5 hours. The reaction mixture is poured into 2 N HCl and extracted with ether. The combined organic layers were washed with 10% aq NaHCO₃ and brine, dried (Na₂SO₄), filtered, and concentrated. Flash chromatography on SiO₂ (hexanes/ethyl acetate, 20:1) provides the product as a colorless oil.

(c) (2R,3S)-3-(triethylsilyloxy)-2,4-dimethyl-5-(2-methylthiazol-4-yl))-pent-4-enal

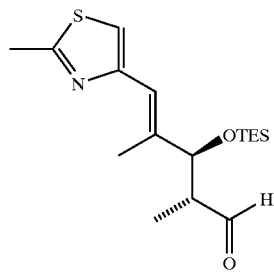

Osmium tetraoxide (1 wt % in THF, 20.3 mL) is added to a mixture of (3S,4S)-4-(triethylsilyloxy)-3,5-dimethyl-6-(2-methylthiazol-4-yl)-1,5-hexadiene (13.5 g), $H_2O$ (21 mL), and N-methylmorpholine N-oxide (50% in THF, 10 mL, 0.048 mol) in tert-butanol (155 mL) at 0° C. After the resulting mixture is stirred for 12 hours, $Na_2SO_3$ (10 g) and water (5 mL) are added. The resulting solution is stirred at 25° C. for 30 minutes and then extracted with ether. The combined extracts are washed with brine, dried ($Na_2SO_4$), filtered, and concentrated. Purification by flash chromatography on $SiO_2$ provides a 1:1 diastereomeric mixture of the diol as a colorless, viscous oil. Lead tetraacetate (19.1 g) is added portionwise over 5 minutes to a suspension of the diol (18.0 g) and $Na_2CO_3$ (8.67 g) in 500 mL of benzene at 0° C. After stirring for 15 minutes, the mixture is filtered through a $SiO_2$ pad to afford the aldehyde product. The product is directly subjected to the next reaction.

(d) (5S)-2-iodo-6-methyl-7-(2-(2,2,2-trichloroethoxycarbonyloxy)methylthiazol-4-yl)-5-(triethylsilyloxy)-2,6-heptadiene To a suspension of ethyltriphenylphosphonium iodide (7.90 g) in THF (150 mL) is added n-butyllithium (7.17 mL, 2.5 M in hexane) at ambient temperature. After disappearance of the solid material, the red solution is cannulated into a vigorously stirred solution of iodine (4.54 g) in THF (150 mL) at −78 ° C. The resulting dark brown suspension is stirred for 5 minutes and allowed to warm gradually to −30° C. A solution of sodium hexamethyldisilazide (17.3 mL, 1.0 M in THF) is added dropwise to afford a dark red solution. A solution of (2R,3S)-3-(triethylsilyloxy)-4-methyl-5-(2-methylthiazol-4-yl)-pent-4-enal (2.0 g) in THF (10 mL) is slowly added, and stirring is continued at −30° C. for 30 minutes. The reaction mixture is diluted with pentane (100 mL), filtered through a pad of Celite, and concentrated. Purification by flash column chromatography on $SiO_2$ (hexane/ethyl acetate, 15:1) affords the vinyl iodide as a yellow syrup.

EXAMPLE 8

(5S)-5-azido-2-iodo-6-methyl-7-(2-methylthiazol-4-yl)-2,6-heptadiene

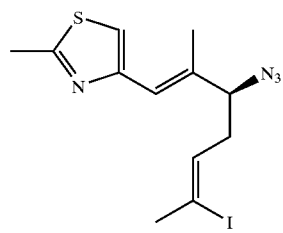

(a) (4R)-4-hydroxy-3,5-dimethyl-6-(2-methylthiazol-4-yl))-1,5-hexadiene

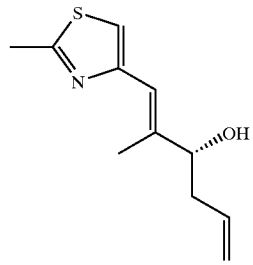

A solution of 2-methyl-3-(2-methylthiazol-4-yl))propenal (4.3 g) in 50 mL of anhydrous ether is cooled to −100° C. A pentane solution of (−)-diisopinocampheylallylborane (1.5 equiv) is added dropwise to the vigorously stirred aldehyde solution. After the addition is complete, the reaction mixture is stirred for 1.5 hours and warmed to −50° C. A solution of 30% aq $H_2O_2$ (20 mL) and 10% aq $NaHCO_3$ (50 mL) is added, and the resulting turbid mixture is stirred at 25° C. for 8 hours. The organic layer is separated, and the aqueous layer is extracted with ether. The combined organic layers are washed with satd aq $Na_2S_2O_3$ and brine, dried ($MgSO_4$), filtered, and concentrated. Purification by flash column chromatography on $SiO_2$ (hexanes/ethyl acetate, 10:1) affords the alcohol as a clear oil.

(b) (4R)-4-(triethylsilyloxy)-5-methyl-6-(2-methylthiazol-4-yl))-1,5-hexadiene

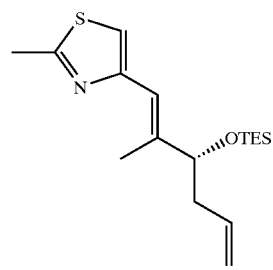

Triethylsilyl trifluromethanesulfonate (15 mL) is added dropwise to a −78° C. solution of (4R)-4-hydroxy-5-methyl-6-(2-methylthiazol-4-yl))-1,5-hexadiene (4.3 g) and 2,6-lutidine (10 mL) in 50 mL of $CH_2Cl_2$. After the addition, the reaction mixture is allowed to warm to ambient temperature and is stirred for 5 hours. The reaction mixture is poured into 2 N HCl and extracted with ether. The combined organic layers were washed with 10% aq $NaHCO_3$ and brine, dried ($Na_2SO_4$), filtered, and concentrated. Flash chromatography on $SiO_2$ (hexanes/ethyl acetate, 20:1) provids the product as a colorless oil.

(c) (3R)-3-(triethylsilyloxy)-4-methyl-5-(2-methylthiazol-4-yl)-pent-4-enal

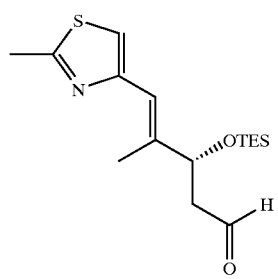

Osmium tetraoxide (1 wt % in THF, 20.3 mL) is added to a mixture of (4R)-4-(triethylsilyloxy)-5-methyl-6-(2-methylthiazol-4-yl)-1,5-hexadiene (13.5 g), H₂O (21 mL), and N-methylmorpholine N-oxide (50% in THF, 10 mL, 0.048 mol) in tert-butanol (155 mL) at 0° C. After the resulting mixture is stirred for 12 hours, Na₂SO₃ (10 g) and water (5 mL) are added. The resulting solution is stirred at 25° C. for 30 minutes and then extracted with ether. The combined extracts are washed with brine, dried (Na₂SO₄), filtered, and concentrated. Purification by flash chromatography on SiO₂ provides a 1:1 diastereomeric mixture of the diol as a colorless, viscous oil. Lead tetraacetate (19.1 g) is added portionwise over 5 minutes to a suspension of the diol (18.0 g) and Na₂CO₃ (8.67 g) in 500 mL of benzene at 0° C. After stirring for 15 minutes, the mixture is filtered through a SiO₂ pad to afford the aldehyde product. The product is directly subjected to the next reaction.

(d) (5R)-2-iodo-6-methyl-7-(2-methylthiazol-4-yl)-5-(triethylsilyloxy)-2,6-heptadiene

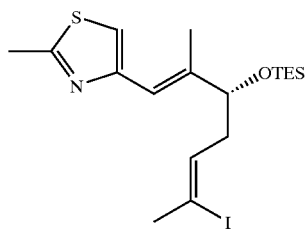

To a suspension of ethyltriphenylphosphonium iodide (7.90 g) in THF (150 mL) is added n-butyllithium (7.17 mL, 2.5 M in hexane) at ambient temperature. After disappearance of the solid material, the red solution is cannulated into a vigorously stirred solution of iodine (4.54 g) in THF (150 mL) at −78° C. The resulting dark brown suspension is stirred for 5 minutes and allowed to warm gradually to −30° C. A solution of sodium hexamethyldisilazide (17.3 mL, 1.0 M in THF) is added dropwise to afford a dark red solution. A solution of (3R)-3-(triethylsilyloxy)-4-methyl-5-(2-methylthiazol-4-yl)-pent-4-enal (2.0 g) in THF (10 mL) is slowly added, and stirring is continued at −30° C. for 30 minutes. The reaction mixture is diluted with pentane (100 mL), filtered through a pad of Celite, and concentrated. Purification by flash column chromatography on SiO₂ (hexane/ethyl acetate, 15:1) affords the vinyl iodide.

(e) (5R)-5-hydroxy-2-iodo-6-methyl-7-(2-methylthiazol-4-yl)-2,6-heptadiene

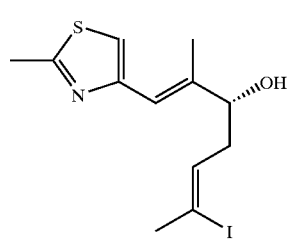

A solution of (5R)-2-iodo-6-methyl-7-(2-methylthiazol-4-yl)-5-(triethylsilyloxy)-2,6-heptadiene (2.28 g) in 50 mL of 3: 1:1 acetic acid/THF/water is stirred at ambient temperature for 8 hoursours, then concentrated. The residue is dissolved in ethyl acetate, washed sequentially with sat. NaHCO₃ and brine, then dried over MgSO₄, filtered, and evaporated. The product is purified by SiO₂ chromatography (30% ethyl acetate/hexanes).

(f) (5S)-5-azido-2-iodo-6-methyl-7-(2-methylthiazol-4-yl)-2,6-heptadiene

A solution of (5R)-5-hydroxy-2-iodo-6-methyl-7-(2-methylthiazol-4-yl)-2,6-heptadiene (1.74 g) in 30 mL of toluene is cooled to 0° C. and treated with diphenylphosphoryl azide (1.65 g) and 1,8-diazabicyclo[5.4.0]undec-7-ene (0.91 g) for 2 hours. The mix is warmed to ambient temperature and diluted with ethyl acetate. The solution is washed sequentially with water, sat. NaHCO₃, and brine, then dried over MgSO₄, filtered, and evaporated. The product is purified by SiO₂ chromatography (7.5% ethyl acetate/hexanes).

EXAMPLE 9

(5S)-5-azido-2-iodo-5-(6-quinolyl)-2-pentene

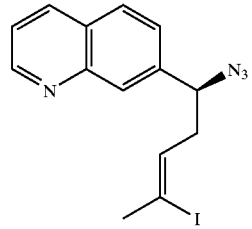

(a) (2S)-N-[(3R)-3-hydroxy-3-(6-quinolyl)propionyl]-2,10-camphorsultam

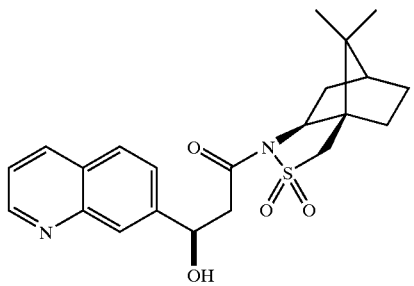

A 1.0 M solution of diethylboron triflate in CH₂Cl₂ (110 mL) is added slowly to a 0° C. solution of 25.7 gm of (2S)-N-acetyl-2,10-camphorsultam in 250 mL of CH₂Cl₂. A solution of diisopropylethylamine (15 mL) in 75 mL of CH₂Cl₂ is then added dropwise over 20 minutes at 0° C., and the mixture is then cooled to −78° C. A solution of quinoline-6-carboxaldehyde (15.7 g) in 100 mL of CH₂Cl₂ is then added at such a rate as to keep the reaction temperature below −70° C. After an additional 2 hours, the mixture is warmed to ambient temperature and quenched by addition of 100 mL of 3:1 tetrahydrofuran/water and 750 mL of sat. aq. NH₄Cl. The mixture is concentrated to a slurry, then diluted with water, adjusted to pH 8, and extracted with ethyl acetate. The extract is washed sequentially with water and brine, then dried over MgSO₄, filtered, and evaporated to yield the crude adduct. Purification by silica gel chromatography yields pure product.

(b) (2S)-N-[(3R)-3-(triethylsilyloxy)-3-(6-quinolyl) propionyl]-2,10-camphorsultam

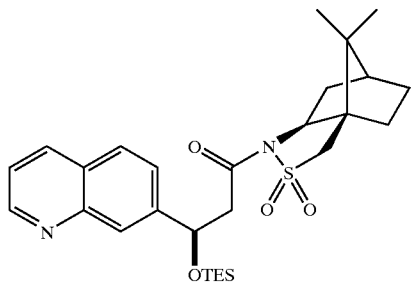

A solution of (2S)-N-[(3R)-3-hydroxy-3-(6-quinolyl) propionyl]-2,10-camphorsultam (41.4 gm) in 250 mL of $CH_2Cl_2$ is cooled on ice and treated with 2,6-lutidine (13 gm) and triethylsilyl trifluoromethanesulfonate (29 gm). After stirring for 12 hours, the mixture is washed with water and dried over $MgSO_4$, filtered, and evaporated to yield the crude product. Purification by silica gel chromatography yields pure product.

(c) (3R)-3-(triethylsilyloxy)-3-(6-quinolyl)propanal

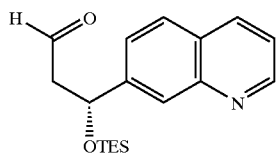

A solution of (2S)-N-[(3R)-3-(triethylsilyloxy)-3-(6-quinolyl)-propionyl]-2,10-camphorsultam (52.8 gm) in 1000 mL of $CH_2Cl_2$ is cooled to −78° C., and a 1.0 M solution of diisobutylaluminum hydride in hexane is added dropwise so as to keep the reaction temperature below 65° C. The mixture is stirred for an additional 6 hours at −78° C., then is quenched by addition of sat. aq. $NH_4Cl$ and allowed to warm to ambient temperature. The mixture is washed with brine, and the organic phase is dried over $MgSO_4$, filtered, and evaporated. The product is purified by silica gel chromatography.

(d) (5R)-2-iodo-5-(6-quinolyl)-5-(triethylsilyloxy)-2-pentene

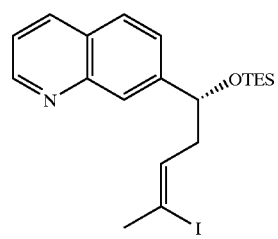

A suspension of ethyltriphenylphosphonium iodide (7.9 gm) in 150 mL of tetrahydrofuran is treated with a 2.5 M solution of n-butyllithium (7.17 mL) at ambient temperature. The resulting red solution is transferred via cannula into a vigorously stirred solution of iodine (4.54 gm) in 150 mL of tetrahydrofuran cooled to −78° C. The resulting suspension is stirred for 5 minutes, then gradually warmed to −30° C. A 1.0 M solution of sodium hexamethyldisilazide (17.3 mL) is then added dropwise to form a red solution. A solution of (3R)-3-(triethylsilyloxy)-3-(6-quinolyl)propanal (1.9 gm) in 10 mL of tetrahydrofuran is then added dropwise, and stirring is continued at −30° C. for 30 minutes. The mixture is diluted with ether, filtered through a pad of Celite, and concentrated. The product is purified by flash chromatography on silica gel.

(e) (5R)-2-iodo-5-(6-quinolyl)-5-hydroxy-2-pentene

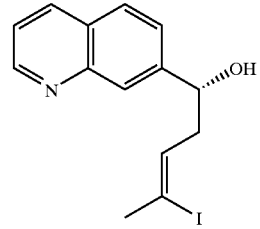

A solution of (5R)-2-iodo-5-(6-quinolyl)-5-(triethylsilyloxy)-2-pentene (2.26 g) in 50 mL of 3:1:1 acetic acid/THF/water is stirred at ambient temperature for 8 hours, then concentrated. The residue is dissolved in ethyl acetate, washed sequentially with sat. $NaHCO_3$ and brine, then dried over $MgSO_4$, filtered, and evaporated. The product is purified by $SiO_2$ chromatography.

(e) (5S)-5-azido-2-iodo-5-(6-quinolyl)-2-pentene

A solution of(5R)-2-iodo-5-(6-quinolyl)-5-hydroxy-2-pentene (1.74 g) in 30 mL of toluene is cooled to 0° C. and treated with diphenylphosphoryl azide (1.65 g) and 1,8-diazabicyclo[5.4.0]undec-7-ene (0.91 g) for 2 hours. The mix is warmed to ambient temperature and diluted with ethyl acetate. The solution is washed sequentially with water, sat. $NaHCO_3$, and brine, then dried over $MgSO_4$, filtered, and evaporated. The product is purified by $SiO_2$ chromatography.

EXAMPLE 10

Tert-butyl (3S,6R,7S,8S)-5-oxo-3-(triethylsilyloxy)-4,4,6,8-tetranethyl-7-(2,2,2-trichloroethoxycarbonyloxy)-10-undecenoate

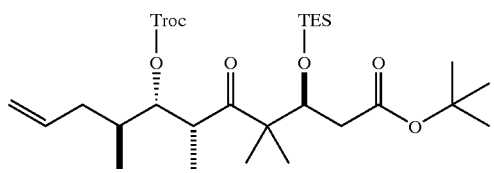

(a) (4R,5S,6S)-1,1-diisopropoxy-5-hydroxy-2,2,4,6-tetramethyl-8-nonen-3-one

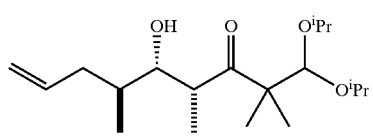

A solution of 1,1-diisopropoxy-2,2,-dimethyl-3-pentanone (3.29 g) in 15 mL of THF is added slowly to a solution of lithium diisopropylamide (15.7 mmol) in 20 mL of THF cooled to −78° C., the mixture is stirred for 30 minutes, warmed to −40° C. and stirred for 30 minutes, then recooled to −78° C. A solution of (2S)-2-methyl-4-pentenal (16.36 mmol) in 2 mL of $CH_2Cl_2$ is added and the mixture is stirred for 1 hour at −78° C. Saturated aq. $NH_4Cl$ is added and the mixture is warmed to ambient temperature and extracted with ethyl acetate. The extract is dried over $Na_2SO_4$, filtered, and evaporated. The residue is purified by silica gel chromatography (2% ethyl acetate/hexanes) to separate the two diastereomeric products.

(b) (4R,5S,6S)-1,1-diisopropoxy-5-(2,2,2-trichloroethoxycarbonyloxy)-2,2,4,6-tetramethyl-8-nonen-3-one

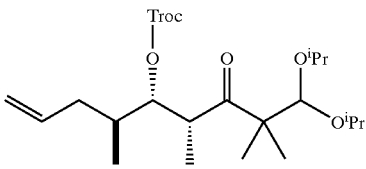

Trichloroethyl chloroformate (2.5 mL) and pyridine (2.95 mL) are added to a solution of (4R,5S,6S)-1,1-diisopropoxy-5-hydroxy-2,2,4,6-tetramethyl-8-nonen-3-one (3.0 g) in 40 mL of $CH_2Cl_2$ at 0° C., and the mixture is stirred for 5 hours before pouring into sat. aq. NaCl and extracting with $CH_2Cl_2$. The extract is dried over $Na_2SO_4$, filtered, and evaporated. The product is purified by chromatography on $SiO_2$ (2% ethyl acetate/hexanes).

(c) (4R,5S,6S)-3-oxo-5-(2,2,2-trichloroethoxycarbonyloxy)-2,2,4,6-tetramethyl-8-nonenal

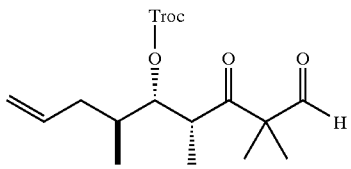

A mixture of (4R,5S,6S)-1,1-diisopropoxy-5-(2,2,2-trichloroethoxycarbonyloxy)-2,2,4,6-tetramethyl-8-nonen-3-one (4.58 g) and p-toluenesulfonic acid monohydrate (0.45 g) in 100 mL of 3:1 THF/water is heated at reflux for 7 hours. The mixture is cooled and poured into sat. aq. $NaHCO_3$, then extracted with ethyl acetate. The extract is dried over $Na_2SO_4$, filtered, and evaporated. The product is purified by chromatography on $SiO_2$ (3% ethyl acetate/hexanes).

(d) tert-butyl (3S,6R,7S,8S)-5-oxo-3-hydroxy-4,4,6,8-tetramethyl-7-(2,2,2-trichloroethoxycarbonyloxy)-10-undecenoate

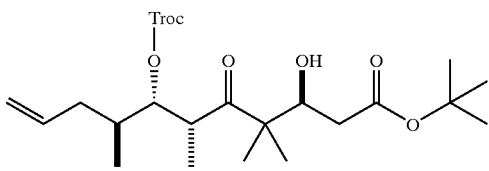

Tert-butyl acetate (0.865 mL) is added to a solution of lithium diisopropylamide (7.52 mmol) in 30 mL of ether at −78° C., and the mixture is stirred for 1 hour. A solution of bis(1,2:5,6-di-O-isopropylidene-α-L-glucofuranos-3-O-yl) cyclopentadienyltitanium chloride (8.34 mmol) in 90 mL of ether is added dropwise over 40 minutes, and the reaction is stirred for an additional 30 minutes at −78° C., warmed to −30° C. and kept for 45 minutes, then recooled to −78° C. A solution of (4R,5S,6S)-3-oxo-5-(2,2,2-trichloroethoxycarbonyloxy)-2,2,4,6-tetramethyl-8-nonenal (2.57 g) in 15 mL of ether is added over 10 minutes and the reaction is continued for 2 hours before addition of 14 mL of 5 M water in THF. The mix is stirred for 1 hour, then filtered through Celite. The filtrate is washed with sat. aq. NaCl, and the brine layer is back extracted with ether. The organic phases are combined, dried with $Na_2SO_4$, filtered, and evaporated. The product is purified by chromatography on $SiO_2$ (7% ethyl acetate/hexanes).

(e) Tert-butyl (3S,6R,7S,8S)-5-oxo-3-(triethylsilyloxy)-4,4,6,8-tetramethyl-7-(2,2,2-trichloroethoxycarbonyloxy)-10-undecenoate A solution of tert-butyl (3S,6R,7S,8S)-5-oxo-3-hydroxy-4,4,6,8-tetramethyl-7-(2,2,2-trichloroethoxycarbonyloxy)-10-undecenoate (1.8 g), imidazole (0.48 g), and triethylsilyl chloride (0.68 g) in 5 mL of dimethylformamide is stirred for 2 hours at ambient temperature, then poured into water and extracted with ether. The extract is washed with sat. aq. NaCl, dried over $MgSO_4$, filtered, and evaporated. The product is purified by chromatography on $SiO_2$ (20:1 toluene/ethyl acetate).

EXAMPLE 11

Tert-butyl (3S,6R,7S,8S)-5-oxo-3-(triethylsilyloxy)-4,4,6,8,10-pentamethyl-7-(2,2,2-trichloroethoxycarbonyloxy)-10-undecenoate

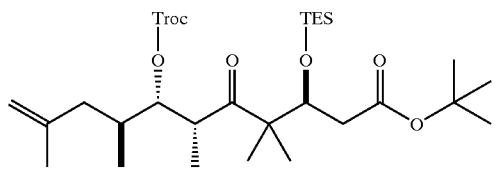

Prepared according to the method of Example 10, substituting (2S)-2,4-dimethyl-4-pentenal in place of (2S)-2-methyl-4-pentenal.

EXAMPLE 12

Tert-butyl (2S,3S,6R,7S,8S)-5-oxo-3-(triethylsilyloxy)-2,4,4,6,8-pentamethyl-7-(2,2,2-trichloroethoxycarbonyloxy)-10-undecenoate

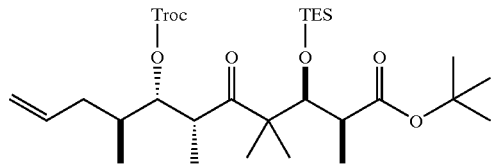

(a) (4S)-3-[(2S,3S,6R,7S,8S)-5-oxo-3-hydroxy-2,4,4,6,8-pentamethyl-7-(2,2,2-trichloroethoxycarbonyloxy)-10-undecenoyl]-4-benzyloxazolidinone

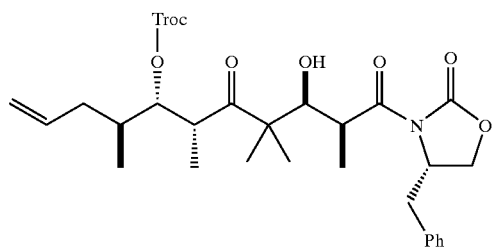

A solution of (4S)-3-propionyl-4-benzyloxazolidinone (91 mmol) in 200 mL of $CH_2Cl_2$ at 0° C. is treated sequentially with dibutylboron triflate (27 mL) and triethylamine (16.7 mL) at such a rate so as to keep the reaction temperature below 3° C. After stirring for 30 minutes, the mixture is cooled to −78° C. and treated with a solution of (4R,5S, 6S)-3-oxo-5-(2,2,2-trichloroethoxycarbonyloxy)-2,2,4,6-tetramethyl-8-nonenal (90 mmol) in 10 mL of CH$_2$Cl$_2$. After 1 hour, the mixture is allowed to warm slowly to 0° C. and stirred an additional 1 hour. The reaction is quenched by addition of 100 mL of pH 7 phosphate buffer and 300 mL of methanol. A mixture of 2:1 methanol/30% aq. H$_2$O$_2$ (300 mL) is then added while maintaining the temperature below 10° C. After stirring for 1 hour, the mixture is concentrated under vacuum to a slurry, which is extracted with ether. The extract is washed sequentially with 5% NaHCO$_3$ and brine, dried over MgSO$_4$, filtered, and evaporated. The product is isolated by silica gel chromatography.

(b) (4S)-3-[(2S,3S,6R,7S,8S)-5-oxo-3-(triethylsilyloxy)-2,4,4,6,8-pentamethyl-7(2,2,2-trichloroethoxycarbonyloxy)-10-undecenoyl]-4-benzyloxazolidinone

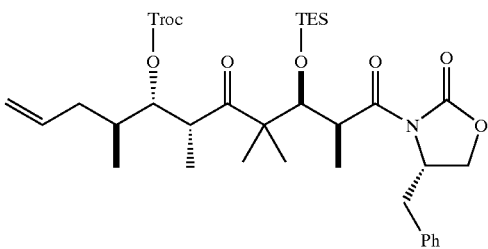

A solution of (4S)-3-[(2S,3S,6R,7S,8S)-5-oxo-3-hydroxy-2,4,4,6,8-perntamethyl-7-(2,2,2-trichloroethoxycarbonyloxy)-10-undecenoyl]-4-benzyloxazolidinone (2.6 g), imidazole (0.48 g), and triethylsilyl chloride (0.68 g) in 5 mL of dimethylformamide is stirred for 2 hours at ambient temperature, then poured into water and extracted with ether. The extract is washed with sat. aq. NaCl, dried over MgSO$_4$, filtered, and evaporated. The product is purified by chromatography on SiO$_2$.

(c) (2S,3S,6R,7S,8S)-5-oxo-3-(triethylsilyloxy)-2,4,4,6,8-pentamethyl-7-(2,2,2-trichloroethoxycarbonyloxy)-10-undecenoic acid

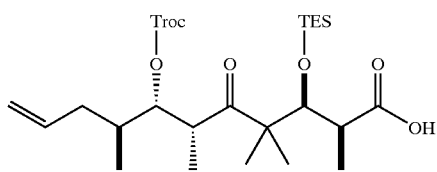

A solution of(4S)-3-[(2S,3S,6R,7S,8S)-5-oxo-3-(triethylsilyloxy)-2,4,4,6,8-pentamethyl-7-(2,2,2-trichloroethoxycarbonyloxy)-10-undecenoyl]-4-benzyloxazolidinone (21.5 g) in 125 mL of 4:1 THF/water is cooled on ice and treated with 10.2 mL of 30% H$_2$O$_2$ followed by a solution of lithium hydroxide (0.96 g) in 50 mL of water. After 1 hour, a solution of sodium sulfite (12.6 g) in 75 mL of water is added, and the mixture is adjusted to pH 3 and concentrated under vacuum. The resulting slurry is extracted with ethyl acetate. The extract is washed with brine, dried over MgSO$_4$, filtered, and evaporated. The product is purified by chromatography on SiO$_2$.

(d) tert-butyl (2S,3S,6R,7S,8S)-5-oxo-3-(triethylsilyloxy)-2,4,4,6,8-pentamethyl-7-(2,2,2-trichloroethoxycarbonyloxy)-10-undecenoate A solution of (2S,3S,6R,7S,8S)-5-oxo-3-(triethylsilyloxy)-2,4,4,6,8-pentamethyl-7-(2,2,2-trichloroethoxycarbonyloxy)-10-undecenoic acid (11.8 g), tert-butanol (4.5 g), and 4-dimethylaminopyridine (0.2 g) in 20 mL of CH$_2$Cl$_2$ is cooled on ice and treated with dicyclohexylcarbodiimide (4.6 g) over a 5-minute period. The mixture is allowed to warm to ambient temperature and is stirred for 3 hours. The slurry is diluted with CH$_2$Cl$_2$ and filtered, and the filtrate is washed sequentially with sat. aq. citric acid, 5% NaHCO$_3$, and brine. The solution is dried over Na$_2$SO$_4$, filtered, and evaporated. The product is purified by chromatography on SiO$_2$.

EXAMPLE 13

Tert-butyl (3S,7R,8S)-5-oxo-3-(triethylsilyloxy)-4,4,8-trimethyl-7-(2,2,2-trichloroethoxycarbonyloxy-10-undecenoate

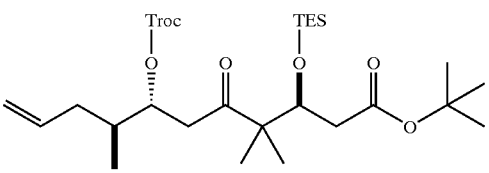

(a) (5R,6S)-1,1-diisopropoxy-5-hydroxy-2,2,6-trimethyl-8-nonen-3-one

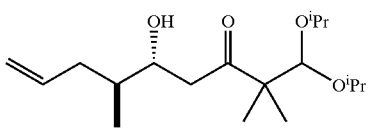

A solution of 1,1-diisopropoxy-2,2,-dimethyl-3-butanone (3.08 g) in 15 mL of ether is added slowly to a solution of lithium diisopropylamide (15.7 mmol) in 20 mL of ether cooled to −78° C., the mixture is stirred for 30 minutes, warmed to −40° C. and stirred for 30 minutes, then recooled to −78° C. A solution of bis(1,2:5,6-di-O-isopropylidene-α-D-glucofuranos-3-O-yl)cyclopentadienyltitanium chloride (17.4 mmol) in 180 mL of ether is added dropwise over 40 minutes, and the reaction is stirred for an additional 30 minutes at −78° C., warmed to −30° C. and kept for 45 minutes, then recooled to −78° C. A solution of (2S)-2-methyl-4-pentenal (16.36 mmol) in 30 mL of ether is added over 10 minutes and the mixture is stirred for 2 hours at −78° C. A 5 M solution of water in THF (28 mL) is added, the mixture is stirred for 1 hour and then filtered through Celite. The filtrate is washed with sat. aq. NaCl, and the brine layer is back extracted with ether. The organic phases are combined, dried with Na$_2$SO$_4$, filtered, and evaporated. The product is purified by chromatography on SiO$_2$.

(b) (5R,6S)-1,1-diisopropoxy-5-(2,2,2-trichloroethoxycarbonyloxy)-2,2,6-trimethyl-8-nonen-3-one

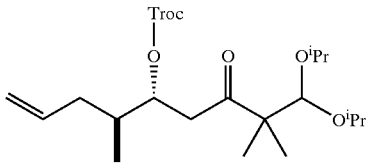

Trichloroethyl chloroformate (2.5 mL) and pyridine (2.95 mL) are added to a solution of (5R,6S)-1,1-diisopropoxy-5-hydroxy-2,2,6-trimethyl-8-nonen-3-one (2.9 g) in 40 mL of CH$_2$Cl$_2$ at 0° C., and the mixture is stirred for 5 hours before pouring into sat. aq. NaCl and extracting with CH$_2$Cl$_2$. The extract is dried over Na$_2$SO$_4$, filtered, and evaporated. The product is purified by chromatography on SiO$_2$.

(c) (5R,6S)-3-oxo-5-(2,2,2-trichloroethoxycarbonyloxy)-2,2,6-trimethyl-8-nonenal

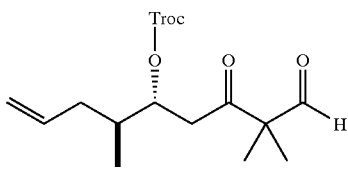

A mixture of (5R,6S)-1,1-diisopropoxy-5-(2,2,2-trichloroethoxycarbonyloxy)-2,2,6-trimethyl-8-nonen-3-one (4.3 g) and p-toluenesulfonic acid monohydrate (0.45 g) in 100 mL of 3:1 THF/water is heated at reflux for 7 hours. The mixture is cooled and poured into sat. aq. NaHCO$_3$, then extracted with ethyl acetate. The extract is dried over Na$_2$SO$_4$, filtered, and evaporated. The product is purified by chromatography on SiO$_2$.

(d) tert-butyl (3S,7R,8S)-5-oxo-3-hydroxy-4,4,8-trimethyl-7-(2,2,2-trichloroethoxy-carbonyloxy)-10-undecenoate

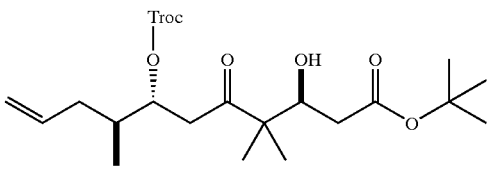

Tert-butyl acetate (0.865 mL) is added to a solution of lithium diisopropylamide (7.52 mmol) in 30 mL of ether at −78° C., and the mixture is stirred for 1 hour. A solution of bis(1,2:5,6-di-O-isopropylidene-α-L-glucofuranos-3-O-yl)cyclopentadienyltitanium chloride (8.34 mmol) in 90 mL of ether is added dropwise over 40 minutes, and the reaction is stirred for an additional 30 minutes at −78° C., warmed to −30° C. and kept for 45 minutes, then recooled to −78° C. A solution of (5R,6S)-3-oxo-5-(2,2,2-trichloroethoxycarbonyl-oxy)-2,2,6-trimethyl-8-nonenal (2.4 g) in 15 mL of ether is added over 10 minutes and the reaction is continued for 2 hours before addition of 14 mL of 5 M water in THF. The mix is stirred for 1 hour, then filtered through Celite. The filtrate is washed with sat. aq. NaCl, and the brine layer is back extracted with ether. The organic phases are combined, dried with Na$_2$SO$_4$, filtered, and evaporated. The product is purified by chromatography on SiO$_2$.

(e) tert-butyl (3S,7R,8S)-5-oxo-3-(triethylsilyloxy)-4,4,8-trimethyl-7-(2,2,2-trichloroethoxy-carbonyloxy)-10-undecenoate A solution of tert-butyl (3S,7R,8S)-5-oxo-3-hydroxy-4,4,8-trimethyl-7-(2,2,2-trichloroethoxycarbonyloxy)-10-undecenoate (1.7 g), imidazole (0.48 g), and triethylsilyl chloride (0.68 g) in 5 mL of dimethylformamide is stirred for 2 hours at ambient temperature, then poured into water and extracted with ether. The extract is washed with sat. aq. NaCl, dried over MgSO$_4$, filtered, and evaporated. The product is purified by chromatography on SiO$_2$.

EXAMPLE 14

Tert-butyl (3S,6R,7S,8S)-5-oxo-3-(triethylsilyloxy)-4,4,6,8-tetramethyl-7-(2,2,2-trichloroethoxycarbonyloxy)-10-undecynoate

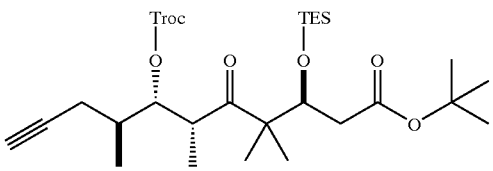

Prepared according to the method of Example 10, substituting (2S)-2-methyl-4-propynal for (2S)-2-methyl-4-propenal.

EXAMPLE 15

Tert-butyl (2S,3S,6R,7S,8S)-5-oxo-3-(triethylsilyloxy)-2,4,4,6,8-pentamethyl-7-(2,2,2-trichloroethoxycarbonyloxy)-10-undecynoate

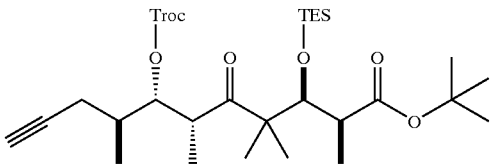

Prepared according to the method of Example 12, substituting (2S)-2-methyl-4-propynal for (2S)-2-methyl-4-propenal.

EXAMPLE 16

Tert-butyl (3S,7S,8S)-5-oxo-3-(triethylsilyloxy)-4,4,8-trimethyl-7-(2,2,2-trichloroethoxycarbonyloxy)-10-undecynoate

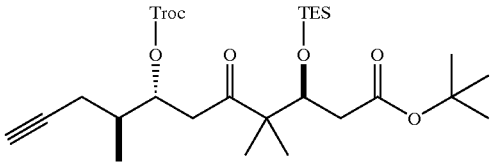

Prepared according to the method of Example 13, substituting (2S)-2-methyl-4-propynal for (2S)-2-methyl-4-propenal.

EXAMPLE 17

21-hydroxy-epothilone D (12,13-Desoxyepothilone F)

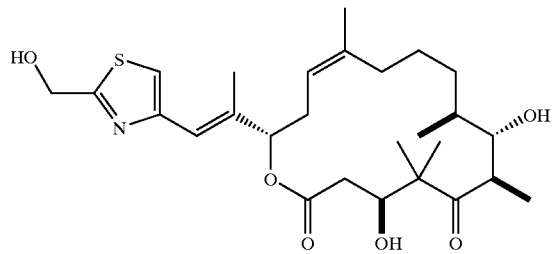

(a) tert-butyl (3S,6R,7S,8S,12Z,15S,16E)-5-oxo-3,15-bis(triethylsilyloxy)-17-(2-(2,2,2-trichloroethoxycarbonyloxymethyl)thiazol-4-yl)-4,4,6,8,12,16-hexamethyl-7-(2,2,2-trichloroethoxycarbonyloxy)-heptadeca-12,16-dienoate

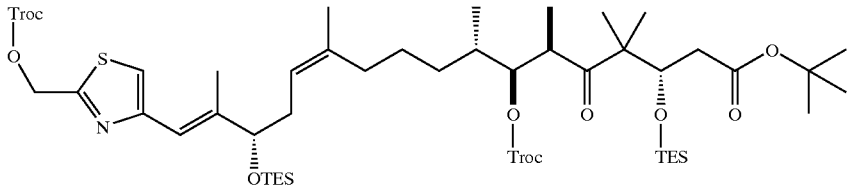

A solution of tert-butyl (3S,6R,7S,8S)-5-oxo-3-(triethylsilyloxy)-4,4,6,8-tetramethyl-7-(2,2,2-trichloroethoxycarbonyloxy)-10-undecenoate (2.12 g) in 4 mL of THF is added to a solution of 9-borabicyclononane dimer (490 mg) in 2 mL of THF, the mixture is stirred for 1 hour at ambient temperature, and then water (0.25 mL) is added to destroy excess 9-BBN. The resulting solution is added to a vigorously stirred mixture of (5S)-2-iodo-6-methyl-7-(2-(2,2,2-trichloroethoxycarbonyl-oxymethyl)thiazol-4-yl)-5-(triethylsilyloxy)-2,6-heptadiene (2.0 g), cesium carbonate (1.49 g), triphenylarsine (0.188 g), and (dppf)PdCl$_2$.CH$_2$Cl$_2$ (0.25 g) in 2 mL of degassed dimethylformamide cooled to 0° C. The reaction is stirred for 15 hours, then poured into 10% NaHSO$_4$ and extracted with ethyl acetate. The organic phase is separated, washed sequentially with 10% NaHCO$_3$ and brine, dried over MgSO$_4$, filtered, and evaporated. The product is purified by flash chromatography on SiO$_2$ (10:1 hexanes/ethyl acetate).

(b) (3S,6R,7S,8S,12Z,15S,16E)-5-oxo-3-(triethylsilyloxy)-15-hydroxy-17-(2-(2,2,2-trichloroethoxycarbonyloxymethyl)thiazol-4-yl)-4,4,6,8,12,16-hexamethyl-7-(2,2,2-trichloroethoxycarbonyloxy)-heptadeca-12,16-dienoic acid

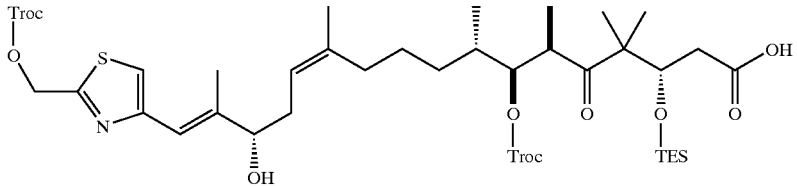

A solution of tert-butyl(3S,6R,7S,8S,12Z,15S,16E)-5-oxo-3,15-bis(triethylsilyloxy)-17-(2-(2,2,2-trichloroethoxycarbonyloxymethyl)thiazol-4-yl)-4,4,6,8,12,16-hexamethyl-7-(2,2,2-trichloroethoxycarbonyloxy)-heptadeca-12,16-dienoate (2.86 g) in 12 mL of CH$_2$Cl$_2$ is treated with 2,6-lutidine (0.86 mL) and triethylsilyl trifluoromethanesulfonate (0.98 g) at 0° C. for 30 minutes, then at ambient temperature for 10 hours. The mixture is diluted with 50 mL of ethyl acetate and poured into 20 mL of 1 N HCl. The organic phase is separated, washed with pH 7 phosphate buffer, dried with Na$_2$SO$_4$, filtered, and concentrated. The residue is dissolved in 5 mL of THF and treated with 0.5 mL of 0.1 N HCl in methanol. The reaction is monitored by thin-layer chromatography, with additional aliquots of methanolic HCl being added to achieve complete reaction. When complete, the reaction is poured into 15 mL of pH 7 phosphate buffer and extracted with ethyl acetate. The extract is washed with brine, dried with Na$_2$SO$_4$, filtered, and evaporated. The product is purified by flash chromatography on SiO$_2$ (1:1 hexanes/ethyl acetate).

(c) 7,21-bis-O-(2,2,2-trichloroethoxycarbonyl)-3-O-(triethylsilyl)-epothilone D

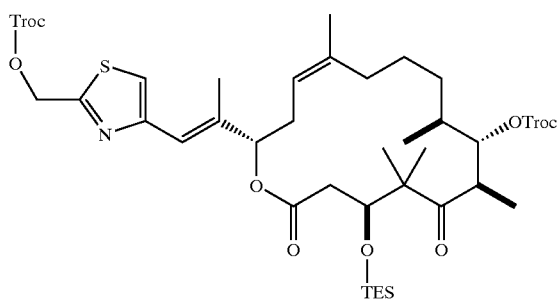

A solution of (3S,6R,7S,8S,12Z,4 5S,16E)-5-oxo-3-(triethylsilyloxy)-15-hydroxy-17-(2-(2,2,2-trichloroethoxycarbonyloxymethyl)thiazol-4-yl)-4,4,6,8,12,16-hexamethyl-7-(2,2,2-trichloroethoxycarbonyloxy)-heptadeca-12,16-dienoic acid (0.426 g) in 9 mL of THF is treated with triethylamine (0.36 mL) and 2,4,6-trichlorobenzoyl chloride (0.528 g). After 15 minutes, 40 mL of toluene is added, and the resulting solution is added via syringe pump over 3 hours to a solution of 4-dimethylaminopyridine (0.525 g) in 400 mL of toluene. After an additional 1 hour, the mixture is filtered through Celite and concentrated. The product is purified by flash chromatography on SiO$_2$ (2:1 hexanes/ethyl acetate).

(d) 21-hydroxy-3-O-(triethylsilyl)-epothilone D

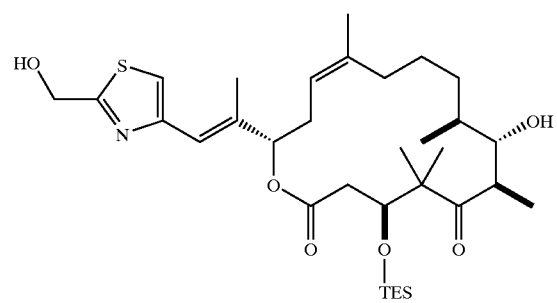

A solution of 7,21-bis-O-(2,2,2-trichloroethoxycarbonyl)-3-O-(triethylsilyl)-epothilone D (0.196 g) in 1 mL of THF is added to a stirred suspension of activated zinc dust (0.261 g) in 2 mL of acetic acid. After stirring for 1.5 hours, the mixture is diluted with ethyl acetate and filtered. The filtrate is washed sequentially with 10% $NaHCO_3$ and brine, dried over $MgSO_4$, filtered, and evaporated. The product is purified by flash chromatography on $SiO_2$ (2:1 hexanes/ethyl acetate).

(e) 21-hydroxy-epothilone D

A solution of 21-hydroxy-3-O-(triethylsilyl)-epothilone D (82 mg) in 2 mL of THF in a polyethylene vessel and treated with 1.5 mL of HF.pyridine for 1 hour at 0° C. and 30 minutes at ambient temperature, then diluted with 30 mL of ethyl acetate and poured into 20 mL of sat. aq. $NaHCO_3$. The organic phase is separated and washed sequentially with 1 N HCl, 10% $NaHCO_3$, and brine, then dried over $MgSO_4$, filtered, and evaporated. The product is purified by flash chromatography on $SiO_2$ (1:2 hexanes/ethyl acetate).

EXAMPLE 18

10,11-dehydroepothilone D

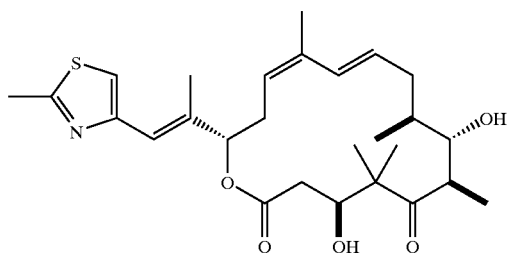

(a) tert-butyl (3S,6R,7S,8S,10E,12Z, 15S,16E)-5-oxo-3,15-bis(triethylsilyloxy)-17-(2-methylthiazol-4-yl)-4,4,6,8,12,16-hexamethyl-7-(2,2,2-trichloroethoxycarbonyloxy)-heptadeca-10,12,16-trienoate (Method A)

Method A: A solution of tert-butyl (3S,6R,7S,8S)-5-oxo-3-(triethylsilyloxy)-4,4,6,8-tetramethyl-7-(2,2,2-trichloroethoxycarbonyloxy)-10-undecenoate (12.2 g) in 4 mL of THF is added to a vigorously stirred mixture of (5S)-2-iodo-6-methyl-7-(2-methylthiazol-4-yl)-5-(triethylsilyloxy)-2,6-heptadiene (1.4 g), cesium carbonate (1.49 g), triphenylarsine (0.188 g), and $(dppf)PdCl_2 \cdot CH_2Cl_2$ (0.25 g) in 2 mL of degassed dimethylformamide cooled to 0° C. The reaction is stirred for 15 hours, then poured into 10% $NaHSO_4$ and extracted with ethyl acetate. The organic phase is separated, washed sequentially with 10% $NaHCO_3$ and brine, dried over $MgSO_4$, filtered, and evaporated. The product is purified by flash chromatography on $SiO_2$ (10:1 hexanes/ethyl acetate).

Method B: A solution of tert-butyl (3S,6R,7S,8S)-5-oxo-3-(triethylsilyloxy)-4,4,6,8-tetramethyl-7-(2,2,2-trichloroethoxycarbonyloxy)-10-undecynoate (2.1 g) in 4 mL of THF is added to a 1.0 M solution of catecholborane in THF (3.3 mL), the mixture is stirred for 2 hour at 60° C. The resulting solution is added to a vigorously stirred mixture of (5S)-2-iodo-6-methyl-7-(2-(2,2,2-trichloroethoxycarbonyl-oxymethyl)thiazol-4-yl)-5-(triethylsilyloxy)-2,6-heptadiene (2.0 g), cesium carbonate (1.49 g), triphenylarsine (0.188 g), and $(dppf)PdCl_2 \cdot CH_2Cl_2$ (0.25 g) in 2 mL of degassed dimethylformamide cooled to 0° C. The reaction is stirred for 15 hours, then poured into 10% $NaHSO_4$ and extracted with ethyl acetate. The organic phase is separated, washed sequentially with 10% $NaHCO_3$ and brine, dried over $MgSO_4$, filtered, and evaporated. The product is purified by flash chromatography on $SiO_2$ (10:1 hexanes/ethyl acetate).

(b) (3S,6R,7S,8S,10E,12Z,15S,16E)-5-oxo-3-(triethylsilyloxy)-15-hydroxy-17(2-methylthiazol-4-yl)-4,4,6,8,12,16-hexamethyl-7-(2,2,2-trichloroethoxycarbonyloxy)-heptadeca-10,12,16-trienoic acid

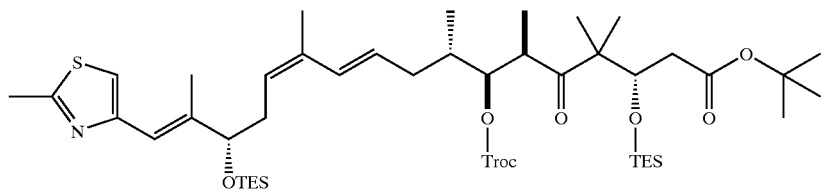

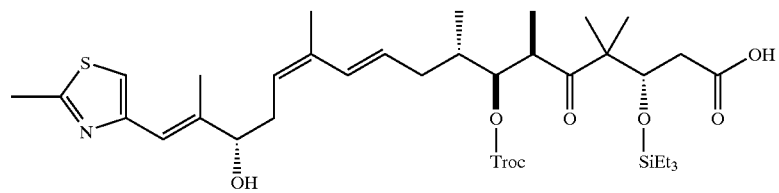

A solution of tert-butyl (3S,6R,7S,8S,10E,12Z,15S,16E)-5-oxo-3,15-bis(triethylsilyloxy)-17-(2-methylthiazol-4-yl)-4,4,6,8,12,16-hexamethyl-7-(2,2,2-trichloroethoxycarbonyloxy)-heptadeca-10,12,16-trienoate (2.38 g) in 12 mL of CH$_2$Cl$_2$ is treated with 2,6-lutidine (0.86 mL) and triethylsilyl trifluoromethanesulfonate (0.98 g) at 0° C. for 30 minutes, then at ambient temperature for 10 hours. The mixture is diluted with 50 mL of ethyl acetate and poured into 20 mL of 1 N HCl. The organic phase is separated, washed with pH 7 phosphate buffer, dried with Na$_2$SO$_4$, filtered, and concentrated. The residue is dissolved in 5 mL of THF and treated with 0.5 mL of 0.1 N HCl in methanol. The reaction is monitored by thin-layer chromatography, with additional aliquots of methanolic HCl being added to achieve complete reaction. When complete, the reaction is poured into 15 mL of pH 7 phosphate buffer and extracted with ethyl acetate. The extract is washed with brine, dried with Na$_2$SO$_4$, filtered, and evaporated. The product is purified by flash chromatography on SiO$_2$ (1:1 hexanes/ethyl acetate).

(c) 7-O-(2,2,2-trichloroethoxycarbonyl)-3-O-(triethylsilyl)-10,11-dehydroepothilone D

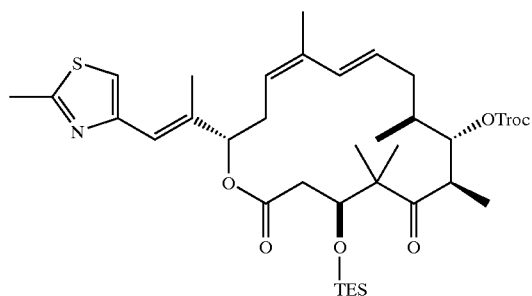

A solution of (3S,6R,7S,8S,10E,12Z,15S,16E)-5-oxo-3-(triethylsilyloxy)-15-hydroxy-17-(2-methylthiazol-4-yl)-4,4,6,8,12,16-hexamethyl-7-(2,2,2-trichloroethoxycarbonyloxy)-heptadeca-10,12,16-trienoic acid (0.4 g) in 9 mL of THF is treated with triethylamine (0.36 mL) and 2,4,6-trichlorobenzoyl chloride (0.528 g). After 15 minutes, 40 mL of toluene is added, and the resulting solution is added via syringe pump over 3 hours to a solution of 4-dimethylaminopyridine (0.525 g) in 400 mL of toluene. After an additional 1 hour, the mixture is filtered through Celite and concentrated. The product is purified by flash chromatography on SiO$_2$ (2:1 hexanes/ethyl acetate).

(d) 3-O-(triethylsilyl)-10,11-dehydroepothilone D

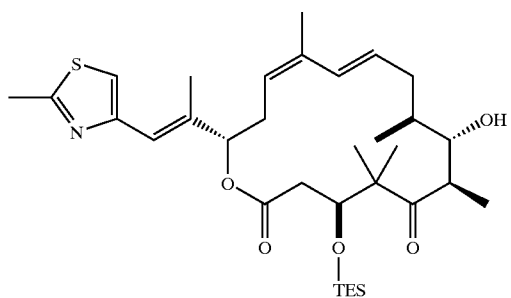

A solution of 7-O-(2,2,2-trichloroethoxycarbonyl)-3-O-(triethylsilyl)-10,11-dehydroepothilone D (0.18 g) in 1 mL of THF is added to a stirred suspension of activated zinc dust (0.261 g) in 2 mL of acetic acid. After stirring for 1.5 hours, the mixture is diluted with ethyl acetate and filtered. The filtrate is washed sequentially with 10% NaHCO$_3$ and brine, dried over MgSO$_4$, filtered, and evaporated. The product is purified by flash chromatography on SiO$_2$ (2:1 hexanes/ethyl acetate).

(e) 10,11-dehydroepothilone D

A solution of 3-O-(triethylsilyl)-10,11-dehydroepothilone D (80 mg) in 2 mL of THF in a polyethylene vessel and treated with 1.5 mL of HF.pyridine for 1 hour at 0° C. and 30 minutes at ambient temperature, then diluted with 30 mL of ethyl acetate and poured into 20 mL of sat. aq. NaHCO$_3$. The organic phase is separated and washed sequentially with 1 N HCl, 10% NaHCO$_3$, and brine, then dried over MgSO$_4$, filtered, and evaporated. The product is purified by flash chromatography on SiO$_2$ (1:2 hexanes/ethyl acetate).

EXAMPLE 19

21-hydroxy-10,11-dehydro-epothilone D

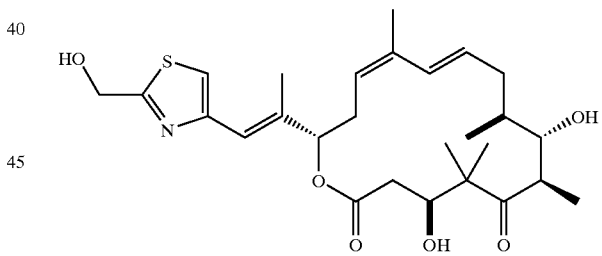

(a) tert-butyl (3S,6R,7S,8S,10E,12Z,15S,16E)-5-oxo-3,15-bis(triethylsilyloxy)-17-(2-(2,2,2-trichloroethoxycarbonyloxymethyl)thiazol-4-yl)-4,4,6,8,12,16-hexamethyl-7-(2,2,2-trichloroethoxycarbonyloxy)-heptadeca-10,12,16-trienoate

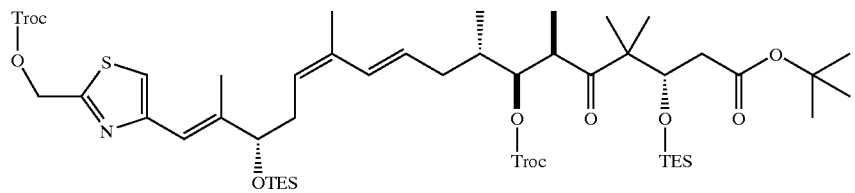

Method A: A solution of tert-butyl (3S,6R,7S,8S)-5-oxo-3-(triethylsilyloxy)-4,4,6,8-tetramethyl-7-(2,2,2-trichloroethoxycarbonyloxy)-10-undecenoate (2.12 g) in 4 mL of THF is added to a vigorously stirred mixture of (5S)-2-iodo-6-methyl-7-(2-(2,2,2-trichloroethoxycarbonyl-oxymethyl)thiazol-4-yl)-5-(triethylsilyloxy)-2,6-heptadiene (2.0 g), cesium carbonate (1.49 g), triphenylarsine (0.188 g), and (dppf)PdCl$_2$.CH$_2$Cl$_2$ (0.25 g) in 2 mL of degassed dimethylformamide cooled to 0° C. The reaction is stirred for 15 hours, then poured into 10% NaHSO$_4$ and extracted with ethyl acetate. The organic phase is separated, washed sequentially with 10% NaHCO$_3$ and brine, dried over MgSO$_4$, filtered, and evaporated. The product is purified by flash chromatography on SiO$_2$ (10:1 hexanes/ethyl acetate).

Method B: A solution of tert-butyl (3S,6R,7S,8S)-5-oxo-3-(triethylsilyloxy)-4,4,6,8-tetramethyl-7-(2,2,2-trichloroethoxycarbonyloxy)-10-undecynoate (2.1 g) in 4 mL of THF is added to a 1.0 M solution of catecholborane in THF (3.3 mL), the mixture is stirred for 2 hour at 60° C. The resulting solution is added to a vigorously stirred mixture of (5S)-2-iodo-6-methyl-7-(2-(2,2,2-trichloroethoxycarbonyl-oxymethyl)thiazol-4-yl)-5-(triethylsilyloxy)-2,6-heptadiene (2.0 g), triphenylarsine (0.188 g), and (dppf)PdCl$_2$.CH$_2$Cl$_2$ (0.25 g) in 2 mL of degassed dimethylformamide cooled to 0° C. The reaction is stirred for 15 hours, then poured into 10% NaHSO$_4$ and extracted with ethyl acetate. The organic phase is separated, washed sequentially with 10% NaHCO$_3$ and brine, dried over MgSO$_4$, filtered, and evaporated. The product is purified by flash chromatography on SiO$_2$ (10:1 hexanes/ethyl acetate).

(b) (3S,6R,7S,8S,10E,12Z,15S,16E)-5-oxo-3-(triethylsilyloxy)-15-hydroxy-17-(2-(2,2,2-trichloroethoxycarbonyloxymethyl)thiazol-4-yl)-4,4,6,8,12,16-hexamethyl-7-(2,2,2-trichloroethoxycarbonyloxy)-heptadeca-10,12,16-trienoic acid

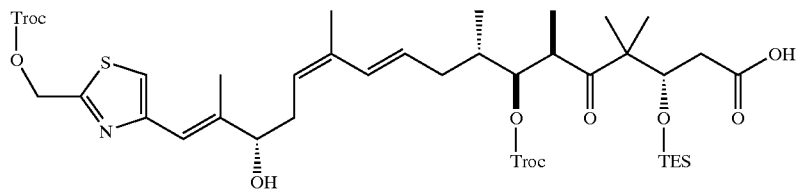

A solution of tert-butyl (3S,6R,7S,8S,10E,12Z,15S,16E)-5-oxo-3,15-bis(triethylsilyloxy)-17-(2-(2,2,2-trichloroethoxycarbonyloxymethyl)thiazol-4-yl)-4,4,6,8,12,16-hexamethyl-7-(2,2,2-trichloroethoxycarbonyloxy)-heptadeca-10,12,16-trienoate (2.8 g) in 12 mL of CH$_2$Cl$_2$ is treated with 2,6-lutidine (0.86 mL) and triethylsilyl trifluoromethanesulfonate (0.98 g) at 0° C. for 30 minutes, then at ambient temperature for 10 hours. The mixture is diluted with 50 mL of ethyl acetate and poured into 20 mL of 1 N HCl. The organic phase is separated, washed with pH 7 phosphate buffer, dried with Na$_2$SO$_4$, filtered, and concentrated. The residue is dissolved in 5 mL of THF and treated with 0.5 mL of 0.1 N HCl in methanol. The reaction is monitored by thin-layer chromatography, with additional aliquots of methanolic HCl being added to achieve complete reaction. When complete, the reaction is poured into 15 mL of pH 7 phosphate buffer and extracted with ethyl acetate. The extract is washed with brine, dried with Na$_2$SO$_4$, filtered, and evaporated. The product is purified by flash chromatography on SiO$_2$ (1:1 hexanes/ethyl acetate).

(c) 7,21-bis-O-(2,2,2-trichloroethoxycarbonyl)-3-O-(triethylsilyl)-10,11-dehydro-epothilone D

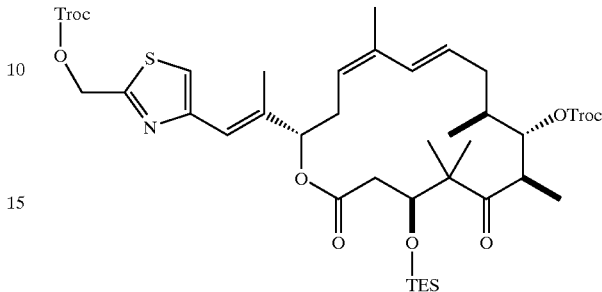

A solution of (3S,6R,7S,8S,10E,12Z,15S,16E)-5-oxo-3-(triethylsilyloxy)-15-hydroxy-17-(2-(2,2,2-trichloroethoxycarbonyloxymethyl)thiazol-4-yl)-4,4,6,8,12,16-hexamethyl-7-(2,2,2-trichloroethoxycarbonyloxy)-heptadeca-10,12,16-trienoic acid (0.42 g) in 9 mL of THF is treated with triethylamine (0.36 mL) and 2,4,6-trichlorobenzoyl chloride (0.528 g). After 15 minutes, 40 mL of toluene is added, and the resulting solution is added via syringe pump over 3 hours to a solution of 4-dimethylaminopyridine (0.525 g) in 400 mL of toluene. After an additional 1 hour, the mixture is filtered through Celite and concentrated. The product is purified by flash chromatography on SiO$_2$ (2:1 hexanes/ethyl acetate).

(d) 21-hydroxy-3-O-(triethylsilyl)-10,11-dehydro-epothilone D

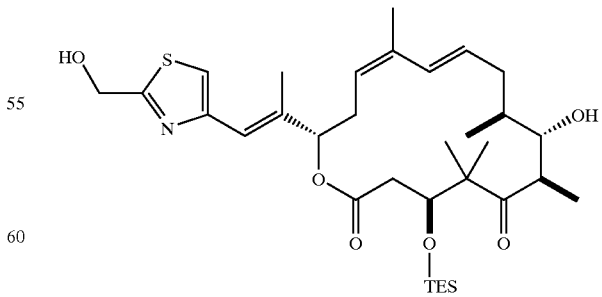

A solution of 7,21-bis-O-(2,2,2-trichloroethoxycarbonyl)-3-O-(triethylsilyl)-10,11-dehydro-epothilone D (0.19 g) in 1 mL of THF is added to a stirred suspension of activated zinc dust (0.261 g) in 2 mL of acetic acid. After stirring for 1.5 hours, the mixture is diluted with ethyl acetate and filtered. The filtrate is washed sequentially with 10% NaHCO$_3$ and brine, dried over MgSO$_4$, filtered, and evaporated. The product is purified by flash chromatography on SiO$_2$ (2:1 hexanes/ethyl acetate).

(e) 21-hydroxy-10,11-dehydro-epothilone D

A solution of 21-hydroxy-3-O-(triethylsilyl)-10,11-dehydro-epothilone D (80 mg) in 2 mL of THF in a polyethylene vessel and treated with 1.5 mL of HF.pyridine for 1 hour at 0° C. and 30 minutes at ambient temperature, then diluted with 30 mL of ethyl acetate and poured into 20 mL of sat. aq. NaHCO$_3$. The organic phase is separated and washed sequentially with 1 N HCl, 10% NaHCO$_3$, and brine, then dried over MgSO$_4$, filtered, and evaporated. The product is purified by flash chromatography on SiO$_2$ (1:2 hexanes/ethyl acetate).

EXAMPLE 20

21-fluoro-10,11-dehydroepothilone D

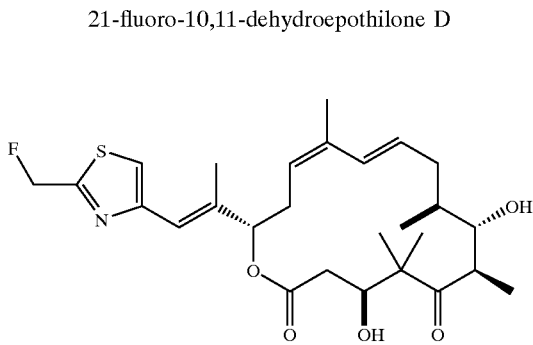

(a) 21-(p-toluenesulfonyloxy)-10,11-dehydroepothilone D

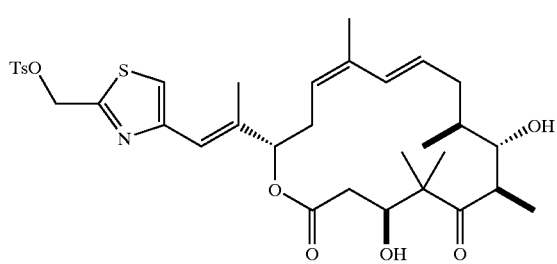

A solution of 21-hydroxy-10,11-dehydro-epothilone D (40 mg) in 2 mL of CH$_2$Cl$_2$ is treated with pyridine (1 mL), 4-dimethylaminopyridine (1 mg), and p-toluenesulfonyl chloride (24 mg) at 0° C. for 30 minutes. The reaction is diluted with ethyl acetate and washed sequentially with 1 N HCl, sat. NaHCO$_3$, and brine, then dried over MgSO$_4$, filtered, and evaporated. The product is purified by SiO$_2$ chromatography (40% ethyl acetate/hexanes).

(b) 21-fluoro-10,11-dehydroepothilone D

A solution of 21-(p-toluenesulfonyloxy)-10,11-dehydroepothilone D (66 mg) in 5 mL of acetonitrile is treated with tetrabutylammonium (triphenylsilyl)difluorosilicate (216 mg) at reflux for 10 hours. The mixture is cooled and evaporated, and the residue is chromatographed on SiO$_2$ (40% ethyl acetate/hexanes) to provide the product.

EXAMPLE 21

(4S,7R,8S,9S,11E,12Z,15S)-4,8-dihydroxy-2,6-dioxo-5,5,7,9,13-pentamethyl-15-(6-quinolyl)-1-oxacyclodeca-11,13-diene

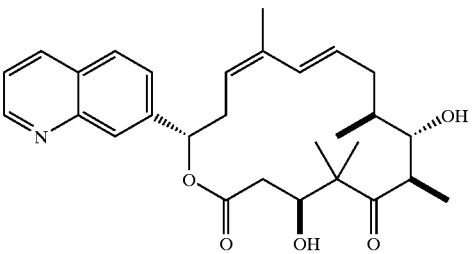

Is prepared according to the method of Example 18 replacing (6S)-2-iodo-5-(6-quinolyl)-5-(triethylsilyloxy)-2-pentene for (5S)-2-iodo-6-methyl-7-(2-methylthiazol-4-yl)-5-(triethylsilyloxy)-2,6-heptadiene.

EXAMPLE 22

12,13-methylene-10,11-dehydroepothilone D

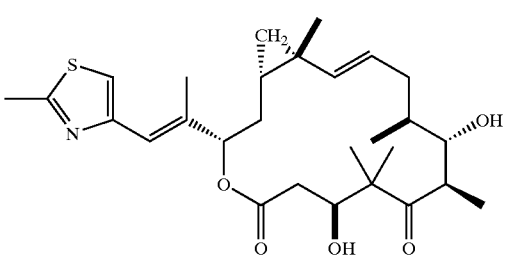

(a) 3,7-bis-O-(tert-butyldimethylsilyl)-10,11-anhydroepothilone D

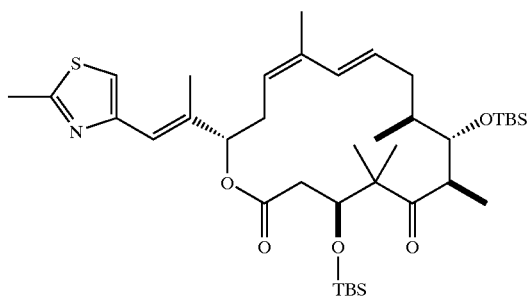

(c) 12,13-methylene-3,7-bis-O-(tert-butyldimethylsilyl)-10,11-dehydroepothilone D

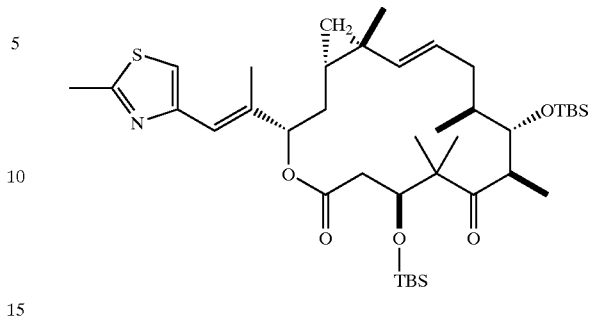

A solution of 10,11-dehydroepothilone D (530 mg) and 2,6-lutidine (0.61 mL) in 30 mL of $CH_2Cl_2$ at 0° C. is treated with tert-butyldimethylsilyl triflate (0.9 mL) for 1 hour, then queched by pouring into sat. $NaHCO_3$ and extracted with $CH_2Cl_2$. The extract is dried over $Na_2SO_4$, filtered, and concentrated. The product is purified by $SiO_2$ chromatography (10% ethyl acetate/hexanes).

(b) 12,13-(dibromomethylene)-3,7-bis-O-(tert-butyldimethylsilyl)-10,11-dehydroepothilone D

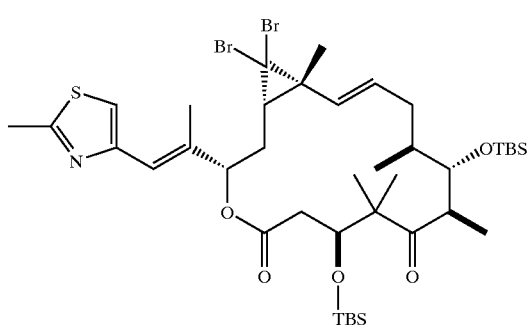

Benzyltriethylammonium chloride (7 mg), ethanol (20 uL), and 50% aq. NaOH are added sequentially to a solution of 3,7-bis-O-(tert-butyldimethylsilyl)-10,11-dehydroepothilone D (230 mg) in 2.7 mL of $CHBr_3$, and the mixture is stirred vigorously at 45° C. for 18 hours. The reaction is cooled to ambient temperature, poured into sat. $NH_4Cl$, and extracted with $CH_2Cl_2$. The extract is dried over $Na_2SO_4$, filtered, and concentrated. The product is purified by $SiO_2$ chromatography (5% ethyl acetate/hexanes).

A solution of 12,13-(dibromomethylene)-3,7-bis-O-(tert-butyldimethylsilyl)-10,11-dehydroepothilone D (30 mg) in 0.5 mL of hexane is treated with tributyltin hydride (80 uL) and azobisisobutyronitrile (1 mg) at reflux for 9 hours. The mixture is cooled, concentrated, and chromatographed on $SiO_2$ to yield the product.

(d) 12,13-methylene-10,11-dehydroepothilone D

A solution of 12,13-methylene-3,7-bis-O-(tert-butyldimethylsilyl)-10,11-dehydroepothilone D (73 mg) in 1 mL of THF is treated with 0.5 mL of a 1 M solution of tetrabutylammonium fluoride in THF for 1 hour. The mixture is diluted with ethyl acetate, washed sequentially with water and brine, then dried over $Na_2SO_4$, filtered, and evaporated. The product is purified by $SiO_2$ chromatography.

EXAMPLE 23

(4S,7R,8S,9S,11E,12Z,15S)-4,8-dihydroxy-2,6-dioxo-5,5,7,9,13-pentamethyl-15-(1-(2-methylthiazol-4-yl)propen-2-yl)-1-azacyclohexadeca-11,13-diene

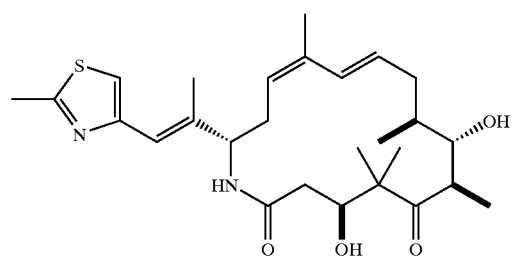

(a) tert-butyl (3S,6R,7S,8S,10E,12Z, 15S,16E)-15-azido-5-oxo-3-(triethylsilyloxy)-17-(2-methylthiazol-4-yl)-4,4,6,8,12,1 6-hexamethyl-7-(2,2,2-trichloroethoxycarbonyloxy)-heptadeca-10,12,16-trienoate (Method A)

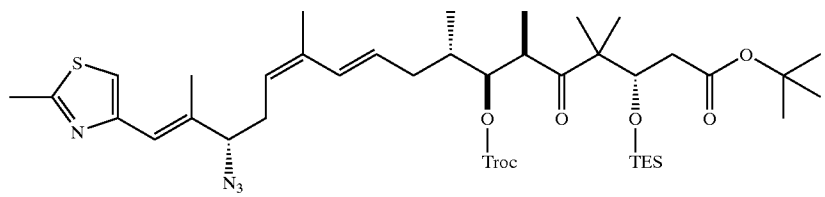

Method A: A solution of tert-butyl (3S,6R,7S,8S)-5-oxo-3-(triethylsilyloxy)-4,4,6,8-tetramethyl-7-(2,2,2-trichloroethoxycarbonyloxy)-10-undecenoate (2.12 g) in 4 mL of THF is added to a vigorously stirred mixture of (5S)-5-azido-2-iodo-6-methyl-7-(2-methylthiazol-4-yl)-2,6-heptadiene (1.1 g), cesium carbonate (1.49 g), triphenylarsine (0.188 g), and (dppf)PdCl$_2$.CH$_2$Cl$_2$ (0.25 g) in 2 mL of degassed dimethylformamide cooled to 0° C. The reaction is stirred for 15 hours, then poured into 10% NaHSO$_4$ and extracted with ethyl acetate. The organic phase is separated, washed sequentially with 10% NaHCO$_3$ and brine, dried over MgSO$_4$, filtered, and evaporated. The product is purified by flash chromatography on SiO$_2$ (10:1 hexanes/ethyl acetate).

Method B: A solution of tert-butyl (3S,6R,7S,8S)-5-oxo-3-(triethylsilyloxy)-4,4,6,8-tetramethyl-7-(2,2,2-trichloroethoxycarbonyloxy)-10-undecynoate (2.1 g) in 4 mL of THF is added to a 1.0 M solution of catecholborane in THF (3.3 mL), the mixture is stirred for 2 hour at 60° C. The resulting solution is added to a vigorously stirred mixture of (5S)-5-azido-2-iodo-6-methyl-7-(2-methylthiazol-4-yl)-2,6-heptadiene (1.1 g), cesium carbonate (1.49 g), triphenylarsine (0.188 g), and (dppf)PdCl$_2$.CH$_2$Cl$_2$ (0.25 g) in 2 mL of degassed dimethylformamide cooled to 0° C. The reaction is stirred for 15 hours, then poured into 10% NaHSO$_4$ and extracted with ethyl acetate. The organic phase is separated, washed sequentially with 10% NaHCO$_3$ and brine, dried over MgSO$_4$, filtered, and evaporated. The product is purified by flash chromatography on SiO$_2$.

(b) tert-butyl (3S,6R,7S,8S,10E,12Z,15S,16E)-15-(tert-butoxycarbonylamino)-5-oxo-3-(triethylsilyloxy)-17-(2-methylthiazol-4-yl)-4,4,6,8,12,16-hexamethyl-7-(2,2,2-trichloroethoxycarbonyloxy)-heptadeca-10,12,16-trienoate

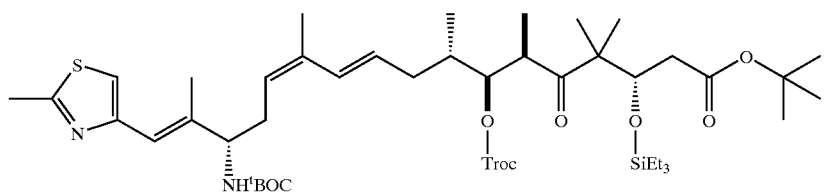

A solution of tert-butyl (3S,6R,7S,8S,10E,12Z,15S,16E)-15-azido-5-oxo-3-(triethylsilyloxy)-17-(2-methylthiazol-4-yl)-4,4,6,8,12,16-hexamethyl-7-(2,2,2-trichloroethoxycarbonyloxy)-heptadeca-10,12,16-trienoate (4.1 g) in 100 mL of THF is treated with triphenylphosphine (2.81 g) at 40° C. for 19 hours, then treated with 2 mL of water and heated at 65° C. for 4 hours. Silica gel (70 g) is added and the mixture is concentrated under vacuum. Silica gel chromatography (1.5% methanol in CHCl$_3$+0.5% Et$_3$N) yields the intermediate amine. The amine (3.3 g) is dissolved in 100 mL of acetonitrile and treated with tert-butyl pyrocarbonate (1.37 g) and triethylamine (0.91 g) for 16 hours at ambient temperature. The solution is diluted with ethyl acetate and washed sequentially with 1 N HCl, sat. NaHCO$_3$, and brine, then dried over MgSO$_4$, filtered, and evaporated. SiO$_2$ chromatography provides the product.

(c) (3S,6R,7S,8S,10E,12Z,15S,16E)-1 5-amino-3-hydroxy-5-oxo-3-17-(2-methylthiazol-4-yl)-4,4,6,8,12,16-hexamethyl-7-(2,2,2-trichloroethoxycarbonyloxy)-heptadeca-10,12,16-trienoic acid

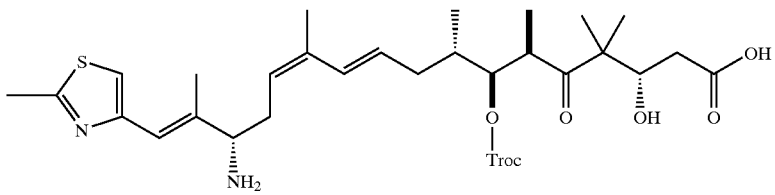

A solution of tert-butyl (3S,6R,7S,8S,10E,12Z,15S,16E)-15-(tert-butoxycarbonylamino)-5-oxo-3-(triethylsilyloxy)-17-(2-methylthiazol-4-yl)-4,4,6,8,12,16-hexamethyl-7-(2,2,2-trichloroethoxycarbonyloxy)-heptadeca-10,12,16-trienoate (0.8 g) in 20 mL of CH$_2$Cl$_2$ is treated with trifluoroacetic acid (10 mL) at ambient temperature for 2 hours, then is concentrated. The crude product is used without purification.

(d) (4S,7R,8S,9S,11E,12Z,15S)-4-hydroxy-2,6-dioxo-5,5,7,9,13-pentamethyl-15-(1-(2-methylthiazol-4-yl)propen-2-yl)-8-(2,2,2-trichloroethoxycarbonyloxy)-1-azacyclohexadeca-11,13-diene

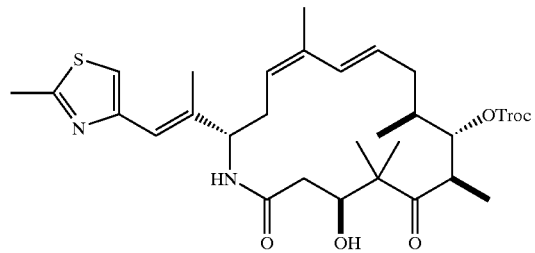

The crude product from step (c) above is dissolved in 10 mL of dimethylformamide and then diluted with 500 mL of CH$_2$Cl$_2$. This is treated with 1-hydroxy-7-azabenzotriazole (0.36 g), diisopropylethylamine (1.02 g), and O-(7-azabenzotriazol-1-yl)-N,N,N',N'-tetramethyluronium hexafluorophosphate (1.03 g) for 16 hours at ambient temperature. The mixture is washed with water, then dried over MgSO$_4$, filtered, and evaporated. The residue is dissolved in 30 mL of acetic acid/THF/water (3:1:1) for 30 minutes, then evaporated, neutralized with NaHCO₃, and extracted with ethyl acetate. The extract is dried over MgSO₄, filtered, and evaporated. The product is isolated by SiO₂ chromatography.

(e) (4S,7R,8S,9S,11E,12Z,15S)-4,8-dihydroxy-2,6-dioxo-5,5,7,9,13-pentamethyl-15-(1-(2-methylthiazol-4-yl)propen-2-yl)-1-azacyclohexadeca-11,13-diene A solution of (4S,7R,8S,9S,11E,12Z,15S)-4-hydroxy-2,6-dioxo-5,5,7,9,13-pentamethyl-15-(1-(2-methylthiazol-4-yl)propen-2-yl)-8-(2,2,2-trichloroethoxycarbonyloxy)-1-azacyclohexadeca-11,13-diene (0.18 g) in 1 mL of THF is added to a stirred suspension of activated zinc dust (0.261 g) in 2 mL of acetic acid. After stirring for 1.5 h, the mixture is diluted with ethyl acetate and filtered. The filtrate is washed sequentially with 10% NaHCO₃ and brine, dried over MgSO₄, filtered, and evaporated. The product is purified by flash chromatography on SiO₂.

EXAMPLE 24

(4S,7R,8S,9S,11E,12Z,15S)-4,8-dihydroxy-2,6-dioxo-5,5,7,9,13-pentamethyl-15-(1-(2-methylthiazol-4-yl)propen-2-yl)-1-azacyclohexadeca-11,13-diene

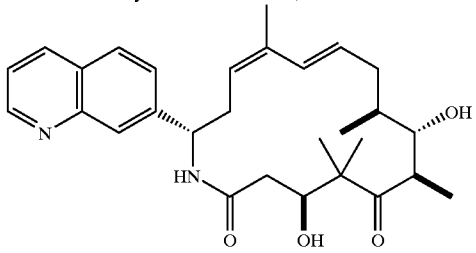

Is prepared according to the method of Example 23, substituting (5S)-5-azido-2-iodo-5-(6-quinolyl)-2-pentene in place of (5S)-5-azido-2-iodo-6-methyl-7-(2-methylthiazol-4-yl)-2,6-heptadiene.

EXAMPLE 25

(4S,7R,8S,9S,11E,12Z,15S)-4,8-dihydroxy-2,6-dioxo-1,5,5,7,9,13-hexamethyl-15-(1-(2-methylthiazol-4-yl)propen-2-yl)-1-azacyclohexadeca-11,13-diene

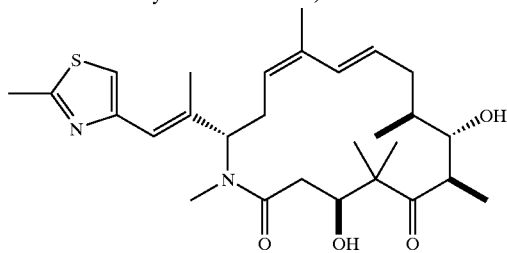

(a) (3S,6R,7S,8S,10E,12Z,15S,16E)-1 5-(methylamino)-3-hydroxy-5-oxo-3-17-(2-methylthiazol-4-yl)-4,4,6,8,12,16-hexamethyl-7-(2,2,2-trichloroethoxycarbonyloxy)-heptadeca-10,12,16-trienoic acid

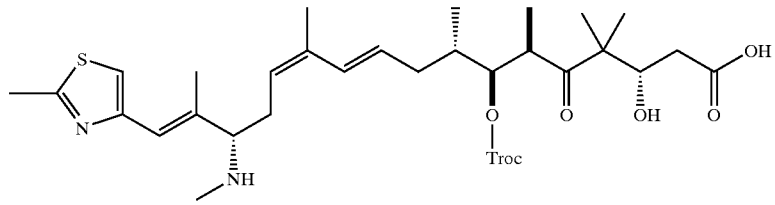

A solution of tert-butyl (3S,6R,7S,8S,10E,12Z,15S,16E)-15-amino-5-oxo-3-(triethylsilyloxy)-17-(2-methylthiazol-4-yl)-4,4,6,8,12,16-hexamethyl-7-(2,2,2-trichloroethoxycarbonyloxy)-heptadeca-10,12,16-trienoate (0.68 g) in 5 mL of methanol is treated with acetaldehyde (50 mg), acetic acid (60 mg), and sodium cyanoborohydride (200 mg) for 12 hours at ambient temperature. The mixture is evaporated to dryness. The crude product is used without purification.

(b) (4S,7R,8S,9S,11E,12Z,15S)-4-hydroxy-2,6-dioxo-1,5,5,7,9,13-hexamethyl-15 -(1-(2-methylthiazol-4-yl)propen-2-yl)-8-(2,2,2-trichloroethoxycarbonyloxy)-1-azacyclohexadeca-11,13-diene

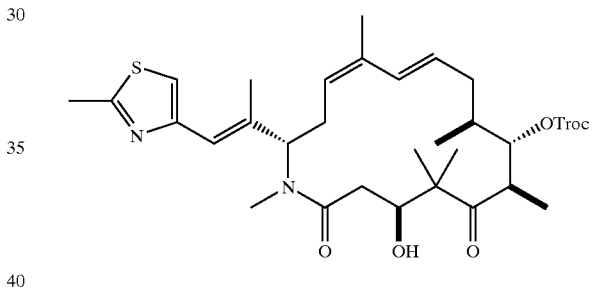

The crude product from step (a) above is dissolved in 10 mL of dimethylformamide and then diluted with 500 mL of CH₂Cl₂. This is treated with 1-hydroxy-7-azabenzotriazole (0.36 g), diisopropylethylamine (1.02 g), and O-(7-azabenzotriazol-1-yl)-N,N,N',N'-tetramethyluronium hexafluorophosphate (1.03 g) for 16 hours at ambient temperature. The mixture is washed with water, then dried over MgSO₄, filtered, and evaporated. The residue is dissolved in 30 mL of acetic acid/THF/water (3:1:1) for 30 minutes, then evaporated, neutralized with NaHCO₃, and extracted with ethyl acetate. The extract is dried over MgSO₄, filtered, and evaporated. The product is isolated by SiO₂ chromatography.

(c) (4S,7R,8S,9S,11E,12Z,15S)-4,8-dihydroxy-2,6-dioxo-1,5,5,7,9,13-hexamethyl-15-(1-(2-methylthiazol-4-yl)propen-2-yl)-1-azacyclohexadeca-11,13-diene A solution of(4S,7R,8S,9S,11E,12Z,15S)-4-hydroxy-2,6-dioxo-1,5,5,7,9,13-hexamethyl-15-(1-(2-methylthiazol-4-yl)propen-2-yl)-8-(2,2,2-trichloroethoxycarbonyloxy)-1-azacyclohexadeca-11,13-diene (0.18 g) in 1 mL of THF is added to a stirred suspension of activated zinc dust (0.261 g) in 2 mL of acetic acid. After stirring for 1.5 hours, the mixture is diluted with ethyl acetate and filtered. The filtrate is washed sequentially with 10% NaHCO₃ and brine, dried over MgSO₄, filtered, and evaporated. The product is purified by flash chromatography on SiO₂.

EXAMPLE 26

Microbial Transformation of C-20 Methyl to C-20 Hydroxymethyl

This example describes the microbial transformation of C-20 methyl to C-20 hydroxymethyl of 10,11-dehydroepothilone D. A frozen vial (approximately 2 ml) of *Amycolata autotrophica* ATCC 35203 or Actinomyces sp. strain PTA-XXX as described by PCT Publication No. WO 00/39276 is used to inoculate 1 500 ml flask containing 100 mL of medium. The vegetative medium consists of 10 g of dextrose, 10 g of malt extract, 10 g of yeast extract, and 1 g of peptone in liter of deionized water. The vegetative culture is incubated for three days at 28° C. on a rotary shaker operating at 250 rpm. One mL of the resulting culture is added to each of sixty-two 500 mL flasks containing the transformation medium which as the same composition as the vegetative medium. The cultures are incubated at 28° C. and 250 rpm for 24 hours. 10,11-dehydroepothilone D is dissolved in 155 ml of ethanol and the solution is distributed to the sixty-two flasks. The flasks are then returned to the shaker and incubated for an additional 43 hours at 28° C. and 250 rpm. The reaction culture is then processed to recover 21-hydroxy-10,11-dehydroepothilone D (which also may be referred to as 10,11-dehydro-12,13-desoxy epothilone F).

EXAMPLE 27

Epoxidation Using EpoK

This example describes the enzymatic epoxidation of 10,11-dehydroepothilone D using EpoK to convert 10,11-dehydroepothilone D into 10,11-dehydroepothilone B. Briefly, the epoK gene product was expressed in *E. coli* as a fusion protein with a polyhistidine tag (his tag) and purified as described by PCT publication, WO 00/31247 which is incorporated herein by reference. The reaction consists of 50 mM Tris (pH7.5), 21 $\mu$M spinach ferredoxin, 0.132 units of spinach ferredoxin: NADP$^+$ oxidoreductase, 0.8 units of glucose-6-phosphate dehydrogenase, 1.4 mM NADP, and 7.1 mM glucose-6-phosphate, 100 $\mu$M or 200 $\mu$M 10,11-dehydroepothilone D, and 1.7 $\mu$M amino terminal histidine tagged EpoK or 1.6 $\mu$M carboxy terminal histidine tagged EpoK in a 100 $\mu$L volume. The reactions are incubated at 30° C. for 67 minutes and stopped by heating at 90° C. for 2 minutes. The insoluble material is removed by centrifugation, and 50 $\mu$L of the supernatant containing the desired product is analyzed by LC/MS.

EXAMPLE 28

Liposomal Composition

This example describes liposomal compositions containing 10,11-dehydroepothilone D. A mixture of lipids and 10,11-dehydroepothilone D are dissolved in ethanol and the solution is dried as a thin film by rotation under reduced pressure. The resultant lipid film is hydrated by addition of the aqueous phase and the particle size of the epothilone-derivative containing liposomes is adjusted to the desired range. Preferably, the mean particle diameter is less than 10 microns, preferably from about 0.5 to about 4 microns. The particle size may be reduced to the desired level, for example, by using mills (e.g., air-jet mill, ball mill, or vibrator mill), microprecipitation, spray-drying, lyophillization, high-pressure homogenization, recrystrytallization from supercritical media, or by extruding an aqueous suspension of the liposomes through a series of membranes (e.g., polycarbonate membranes) having a selected uniform pore size. In one embodiment, the liposomal composition comprises: an inventive compound (1.00 mg); phosphatidylcholine (16.25 mg); cholesterol (3.75 mg); polyethyleneglycol derivatized distearyl phosphatidylethanolamine (5.00 mg); lactose (80.00 mg); citric acid (4.20 mg); tartaric acid (6.00 mg); NaOH (5.44 mg); water (up to 1 mL). In another embodiment, the liposomal composition comprises: an inventive compound (1.00 mg); phosphatidylcholine (19.80 mg); cholesterol (3.75 mg); distearyl phosphatidylcholine (1.45 mg); lactose (80.00 mg); citric acid (4.20 mg); tartaric acid (6.00 mg); NaOH (5.44 mg); water (up to 1 mL). In yet another embodiment, the liposomal composition comprises: an inventive compound (1.00 mg); 1-palmitoyl-2-oleyl-sn-glycero-3-phosphocholine (17.50 mg); 1-palmitoyl-2-oleyl-sn-glycero-3-phosphoglycerol, Na (7.50 mg); lactose (80.mg); citric acid (4.20 mg); tartaric acid (6.00 mg); NaOH (5.44 mg); water (up to 1 mL). Liposomal compositions containing other compounds of the present invention are prepared using conditions similar to those described above.

EXAMPLE 29

This example describes the preparation of a poly-glutamic acid-21-hydroxy-10,11-dehydroepothilone D conjugate. Poly(1-glutamic acid) ("PG") sodium salt (MW 34 K, Sigma, 0.35 g) is dissolved in water. The pH of the queous solution is adjusted to 2 using 0.2 M HCl. The precipitate is collected, dialyzed against distilled water, and lyophilized to yile 0.29 g of PG. To a solution of PG (75 mg, repeating unit FW 170, 0.44 mmol) in dry DMF (1.5 mL) is added 20 mg of 21-hydroxy-10,11-dehydroepothilone D, 15 mg of dicyclohexylcarbodiimide ("DCC") and a trace amount of dimethylaminopyridine. The reaction is allowed to proceed at room temperature for four hours or until completed as indicated by thin layer chromatography. The reaction mixture is poured into chloroform and the resulting precipitate is collected and dried in a vacuum to yield approximately 65 mg of PG-21-hydroxy-10,11-dehydroepothilone D conjugate. Changing the weight ratio of inventive compound to PG in the starting materials results in polymeric conjugates of various concentrations of 21-hydroxyl-10,11-dehydroepothilone D. Conjugates of other compounds of the present invention are prepared using conditions similar to those described above.

EXAMPLE 30

Intravenous Formulaion

This example describes an intravenous formuation of 10,11-dehydroepothilone D. The formulation contains 10 mg/mL of 10,11-dehydroepothilone D in a vehicle containing 30% propylene glycol, 20% Creomophor EL, and 50% ethanol. The vehicle is prepared by measuring ethanol (591.8 g) to a beaker containing a stir bar; adding Creomophor EL (315.0 g) to the solution and mixing for ten minutes; and then adding propylene glycol (466.2 g) to the solution and mixing for another ten minutes. 10,11-dehydroepothilone D (1 g) is added to a 1 L volumetric flask containing 400–600 mL of the vehicle and mixed for five minutes. After 10,11-dehydroepothilone D is in solution, the volume is brought to 1 L; allowed to mix for another ten minutes; and filtered through a 0.22 $\mu$m Millipore Millipak filter. The resulting solution is used to aseptically fill sterile 5 mL vials using a metered peristaltic pump to a targeted fill volume of 5.15 mL/vial. The filled vials are immediately stoppered and crimped.

The vial containing 10 mg/mL of 10,11-dehydroepothilone D is diluted in normal saline or 5% dextrose solution for administration to patients and administered in non-PVC, non-DEHP bags and administration sets. The product is infused over a one to six hour period to deliver the desired dose.

In one embodiment, the formulation is diluted twenty fold in sterile saline prior to intravenous infusion. The final infusion concentration is 0.5 mg/mL of the inventive compound, 1.5% propylene glycol, 1% Chremophor EL, and 2.5% ethanol which is infused over a one to six hour period to deliver the desired dose.

Intravenous formulations containing other compounds of the present invention may be prepared and used in a similar manner.

EXAMPLE 31

Pretreatment for Cremophorg Toxicity

This example describes a pretreatement regiment for for Cremophorg toxicity. Formulations of 10,11-dehydroepothilone D or another compound of the invention that includes Cremophor® may cause toxicity in patients. Pretreatment with steroids can be used to prevent anaphylaxis. Any suitable corticosterioid or combination of corticosteroid with $H_1$ antagonists and/or $H_2$ antagonists may be used. In one embodiment, a subject is premedicated with an oral dose of 50 mg of diphenylhydramine and 300 mg of cimetidine one hour prior to treatment with the inventive compound in a Cremophor® containing formulation. In another embodiment, the subject is premedicated with an intravenous administration of 20 mg of dexamethasone at least one half hour prior to treatment with the inventive compound in a Cremophor® containing formulation. In another embodiment, the subject is premedicated with an intravenous administration of 50 mg of diphenylhydramine, 300 mg of cimetidine and 20 mg of dexamethasone at least one half hour prior to treatment with the inventive compound in a Cremophor® containing formulation. In yet another embodiment, the weight of the subject is taken into account and the subject is pretreated with an administration of diphenylhydramine (5 mg/kg, i.v.); cimetidine (5 mg/kg, i.v).; and dexamethasone (1 mg/kg, i.m.) at least one half hour prior to the treatment with the inventive compound in a Cremophor® containing formulation.

All scientific and patent publications referenced herein are hereby incorporated by reference. The invention having now been described by way of written description and example, those of skill in the art will recognize that the invention can be practiced in a variety of embodiments, that the foregoing description and example is for purposes of illustration and not limitation of the following claims.

What is claimed is:

1. A purified compound of the formula

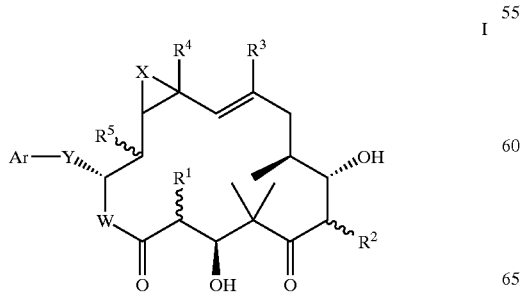

I wherein:
$R^1$, $R^2$, $R^3$, and $R^5$ are each independently hydrogen, $C_1–C_{10}$ alkyl, $C_2–C_{10}$ alkenyl, $C_2–C_{10}$ alkynyl, aryl or alkylaryl;

$R^4$ is hydrogen, halogen $C_1–C_{10}$ alkyl, $C_1–C_{10}$ hydroxyalkyl, $C_1–C_{10}$ haloalkyl, aryl, —C(=O)$R^6$, —C(=O)O$R^6$, —N$R^6R^7$ where $R^6$ and $R^7$ are each independently hydrogen, $C_1–C_{10}$ aliphatic, aryl or alkylaryl;

W is N$R^8$ where $R^8$ is hydrogen, $C_1–C_{10}$ alkyl, $C_2–C_{10}$ alkenyl, $C_2–C_{10}$ alkynyl, aryl or alkylaryl;

X is O, $CH_2$ or a carbon-carbon bond;

Y is absent or a $C_1–C_{10}$ alkyl, $C_2–C_{10}$ alkenyl, or $C_2–C_{10}$ alkynyl; and Ar is aryl.

2. The compound as in claim 1 wherein
$R^1$, $R^2$, $R^3$, and $R^5$ are each independently hydrogen or $C_1–C_5$ alkyl;
$R^4$ is hydrogen, $C_1–C_5$ alkyl, $C_1–C_5$ hydroxyalkyl, $C_1–C_5$ haloalkyl, —C(=O)$R^6$, —C(=O)O$R^6$, —N$R^6R^7$ where $R^6$ and $R^7$ are each independently hydrogen or $C_1–C_5$ alkyl;
W is N$R^8$ where $R^8$ is hydrogen or $C_1–C_5$ alkyl;
X is O, $CH_2$ or a carbon-carbon bond;
Y is absent or $C_2–C_5$ alkenyl; and
Ar is a heteroaryl.

3. The compound as in claim 1 wherein
$R^1$, $R^2$, $R^3$, and $R^5$ are each independently hydrogen, methyl or ethyl;
$R^4$ is hydrogen, methyl, ethyl, hydroxymethyl, hydroxyethyl, fluoromethyl or fluoroethyl;
W is NH;
X is O, $CH_2$ or a carbon-carbon bond;
Y is absent or $C_2–C_5$ alkenyl; and
Ar is an aryl selected from the group consisting of phenyl, pyridyl, pyridazinyl, pyrimidinyl, pyrazinyl, furyl, thienyl, pyrrolyl, imidazolyl, pyrazolyl, thiazolyl, oxazolyl, quinolyl, isoquinolyl, quinoxalyl, indolyl, benzothiazolyl, benzoxazolyl, benzoimidazolyl, and benzopyrazolyl.

4. The compound as in claim 1 wherein
$R^1$, $R^2$, $R^3$, and $R^5$ are each independently hydrogen or methyl;
$R^4$ is hydrogen, methyl, ethyl, or fluoromethyl;
W is NH;
X is O, $CH_2$ or a carbon-carbon bond;
Y is absent or $C_2–C_3$ alkenyl; and
Ar is an aryl selected from the group consisting of thiazolyl, oxazolyl, quinolyl, isoquinolyl, quinoxalyl, indolyl, benzothiazolyl, benzoxazolyl, benzoimidazolyl, and benzopyrazolyl.

5. A purified compound of the formula

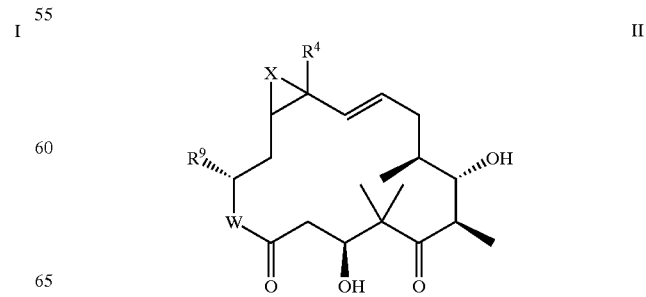

II wherein:

W is $NR^8$ where $R^8$ is hydrogen or $C_1$–$C_5$ alkyl;

X is O, $CH_2$ or a carbon-carbon bond;

$R^4$ is hydrogen, $C_1$–$C_5$ alkyl, $C_1$–$C_5$ hydroxyalkyl, $C_1$–$C_5$ haloalkyl, —C(=O)$R^6$, —C(=O)O$R^6$, —N$R^6R^7$ where $R^6$ and $R^7$ are each independently hydrogen or $C_1$–$C_5$ alkyl; and, $R^9$ is aryl or $R^{11}$CH=C($R^{10}$)— wherein $R^{11}$ is aryl and $R^{10}$ is hydrogen, halide, $C_1$–$C_5$ alkyl, $C_1$–$C_5$ hydroxylalkyl, or $C_1$–$C_5$ haloalkyl, provided that 10,11-dehydroepothilone C is excluded.

6. The compound as in claim 5 wherein:

W is NH; and,

X is $CH_2$ or a carbon-carbon bond;

$R^4$ is hydrogen, methyl, ethyl, hydroxymethyl, hydroxyethyl, fluoromethyl or fluoroethyl; and, $R^9$ is a bicyclic heteroaryl or $R^{11}$CH=C($R^{10}$)— wherein $R^{11}$ is 2-methyl-1,3-thiazolinyl, 2-methyl-13, oxazolinyl, 2-hydroxymethyl-1,3-thiazolinyl, or 2-hydroxymethyl-1,3-oxazolinyl and $R^{10}$ is hydrogen or methyl.

7. The compound as in claim 5 wherein

W is NH; and

X is $CH_2$ or a carbon-carbon bond;

$R^4$ is hydrogen, methyl, ethyl, hydroxymethyl, hydroxyethyl, fluoromethyl, or fluoroethyl; and, $R^9$ is selected from the group consisting of

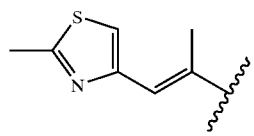
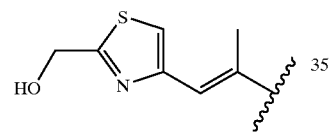
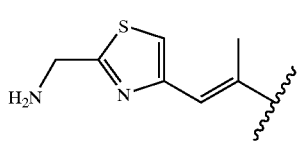
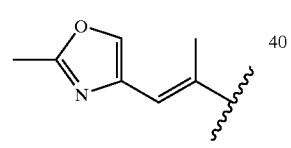
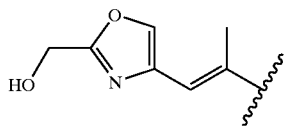
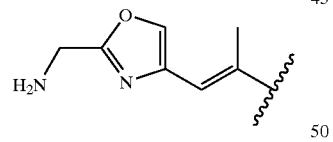
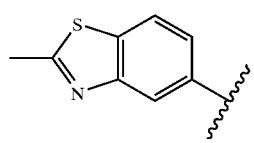
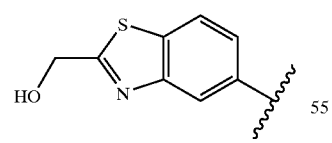
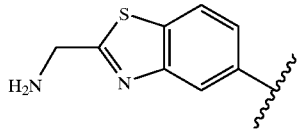
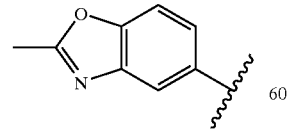
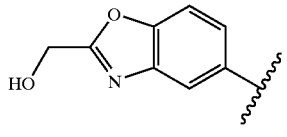
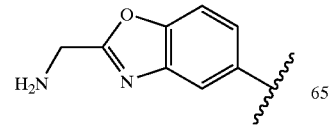

-continued

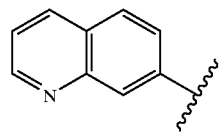
and
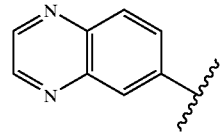
.

8. A purified compound selected from the group consisting of

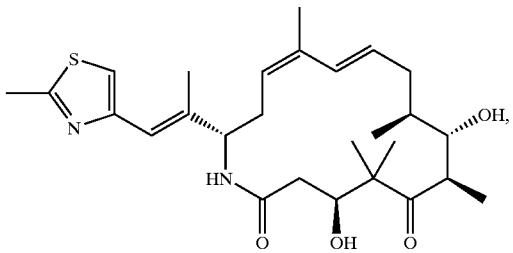

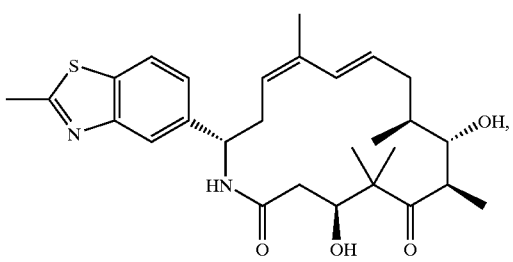

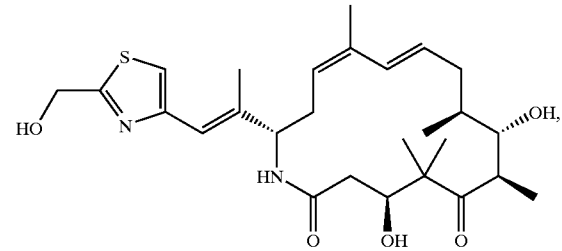

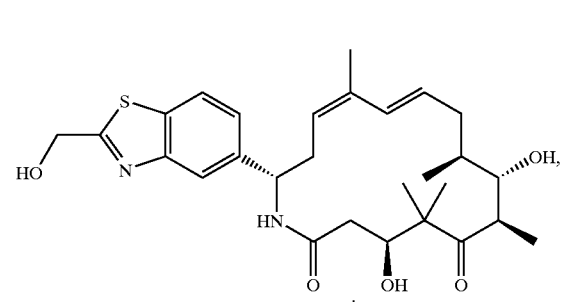

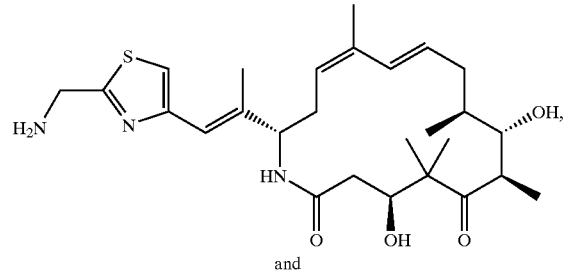

and

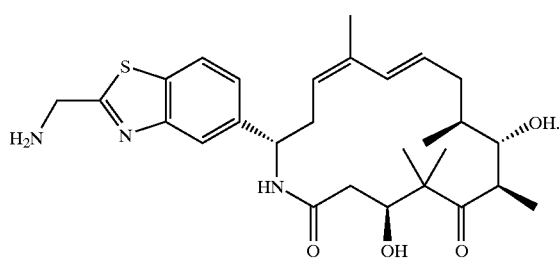

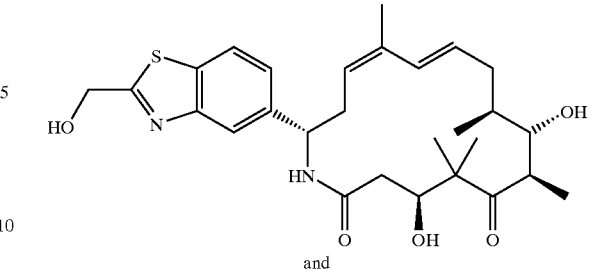

and

9. A method of treating a subject suffering from a condition characterized by cellular hyperproliferation comprising administering to said subject a therapeutically effective amount of a compound of claim 1.

10. A method of treating a subject suffering from a condition characterized by cellular hyperproliferation comprising administering to said subject a therapeutically effective amount of a compound of claim 4.

11. The method of claim 9 wherein the compound is selected from the group consisting of

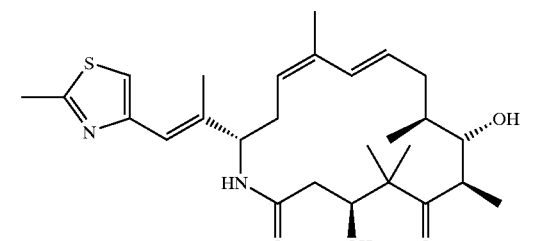

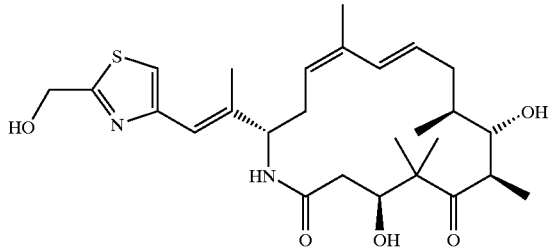

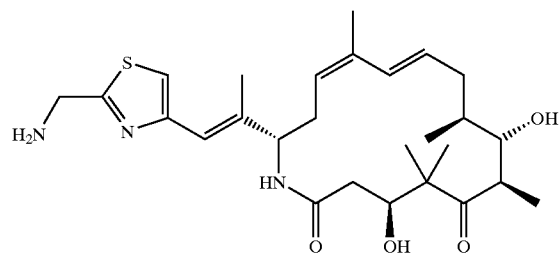

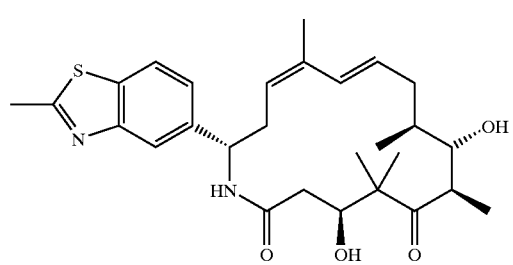

12. The method as in claim 9 wherein the condition is cancer.

13. The method as in claim 12 wherein the condition is a cancer of the head or neck.

14. The method as in claim 12 wherein the condition is a cancer of the liver or biliary tree.

15. The method as in claim 12 wherein the condition is an intestinal cancer.

16. The method as in claim 12 wherein the condition is ovarian cancer.

17. The method as in claim 12 wherein the condition is lung cancer.

18. The method as in claim 12 wherein the condition is a sarcoma.

19. The method as in claim 12 wherein the condition is a neoplasm of the central nervous system.

20. The method as in claim 12 wherein the condition is a lymphoma.

21. The method as in claim 9 wherein the condition is psoriasis.

22. The method as in claim 9 wherein the condition is rheumatoid arthritis.

23. The method as in claim 9 wherein the condition is multiple sclerosis.

24. The method as in claim 9 wherein the condition is atherosclerosis.

25. The compound of claim 8 having the formula

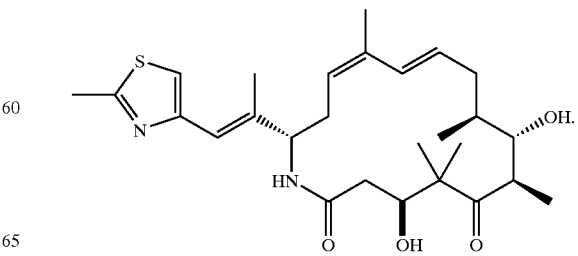

26. The compound of claim 8 having the formula
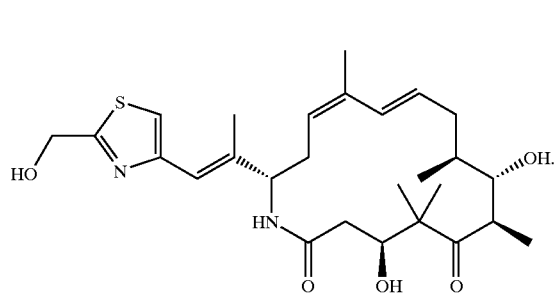
27. The compound of claim 8 having the formula
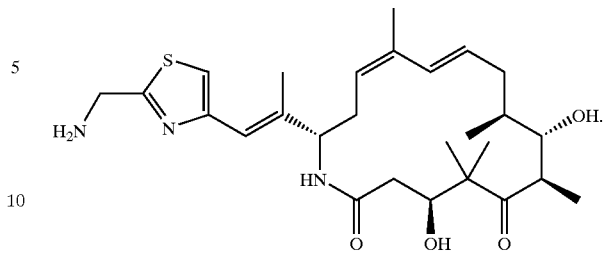
* * * * *